US006379965B1

(12) United States Patent
Boutin

(10) Patent No.: US 6,379,965 B1
(45) Date of Patent: *Apr. 30, 2002

(54) MULTIFUNCTIONAL COMPLEXES FOR GENE TRANSFER INTO CELLS COMPRISING A NUCLEIC ACID BOUND TO A POLYAMINE AND HAVING AN ENDOSOME DISRUPTION AGENT

(75) Inventor: Raymond H. Boutin, Thornton, PA (US)

(73) Assignee: American Home Products Corporation, Madison, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/425,597

(22) Filed: Oct. 22, 1999

Related U.S. Application Data

(60) Division of application No. 08/809,397, filed as application No. PCT/US95/12502 on Sep. 28, 1995, now Pat. No. 6,127,170, which is a continuation-in-part of application No. 08/314,060, filed on Sep. 28, 1994, now Pat. No. 5,837,533.

(51) Int. Cl.$^7$ ............................................... C12N 15/63
(52) U.S. Cl. ........................................ 435/455; 536/23.1
(58) Field of Search ........................ 514/44; 435/320.1, 435/455; 424/450; 536/23.1

(56) References Cited

U.S. PATENT DOCUMENTS

| | | | |
|---|---|---|---|
| 5,108,921 A | 4/1992 | Low et al. | 435/240.1 |
| 5,166,320 A | 11/1992 | Wu et al. | 530/395 |
| 5,171,678 A | 12/1992 | Behr et al. | 435/172.3 |
| 5,283,185 A | 2/1994 | Epand et al. | 435/172.3 |
| 5,614,503 A | 3/1997 | Chaudhary et al. | 514/44 |
| 5,650,096 A | 7/1997 | Harris et al. | 252/357 |
| 5,719,131 A | 2/1998 | Harris et al. | 514/44 |
| 5,747,471 A | 5/1998 | Siegel et al. | 514/44 |
| 5,767,099 A | 6/1998 | Harris et al. | 514/44 |
| 5,783,565 A | 7/1998 | Siegel et al. | 514/44 |
| 5,837,533 A | * 11/1998 | Boutin | 435/320.1 |
| 5,840,710 A | 11/1998 | Lee et al. | 514/44 |
| 5,910,487 A | 6/1999 | Yew et al. | 514/44 |
| 5,912,239 A | 6/1999 | Siegel et al. | 514/182 |
| 5,925,628 A | 7/1999 | Lee et al. | 514/169 |
| 5,935,936 A | 8/1999 | Fasbender et al. | 514/44 |
| 5,942,634 A | 8/1999 | Siegel et al. | 552/524 |
| 5,948,767 A | 9/1999 | Scheule et al. | 514/44 |
| 5,981,273 A | 11/1999 | Curiel et al. | 435/320.1 |

FOREIGN PATENT DOCUMENTS

| | | |
|---|---|---|
| WO | WO 86/00930 | 2/1986 |
| WO | WO 90/11092 | 10/1990 |
| WO | WO 90/12095 | 10/1990 |
| WO | WO 90/12096 | 10/1990 |
| WO | WO 91/16024 | 10/1991 |
| WO | WO 92/06180 | 4/1992 |
| WO | WO 93/19768 | 10/1993 |
| WO | WO 93/24640 | 12/1993 |

OTHER PUBLICATIONS

Crystal (1995) Science 270, 404–410.*
Blau et al (Nov. 2, 1995) New England J. Med., 1204–1207.*
Verma et al (1997) Nature 389, 239–242.*
Ross et al (1996) Human Gene Therapy 7, 1781–1790.*
Ledley et al (1995) Human Gene Therapy 6, 1129–1144.*
Connelly, C. et al., "Polyamines Eliminate an Extreme Size Bias against Transformation of Large Yeast Artificial Chromosome DNA", *Genomics,* 1991, 10, 10–16.
Jones, J. and Risser, "Cell Fusion Induced by the Murine Leukemia Virus Envelope Glycoprotein", *J. of Virology,* 1993, 67(1), 67–74.
Kono, K. et al., "Fusion Activity of an Amphiphilic Polypeptide Having Acidic Amino Acid Residues: Generation of Fusion Activity by α–Helix Formation and Charge Neutralization", *Biochimica et Biophysica Acta* 1993, 1164, 81–90.
Lear, J. and DeGrado, "Membrane Binding and Conformational Properties of Peptides Representing the $NH_2$ Terminus of Influenza HA–2", *The J. of Biol. Chem.,* 1987, 262(14), 6500–6505.
Midoux, P. et al., "Specific Gene Transfer Mediated by Lactosylated Poly–L–Lysine into Hepatoma Cells", *Nucleic Acids Res.,* 1993, 21(4), 871–878.
Nieva, J. et al., "Interaction of the HIV–1 Fusion Peptide with Phospholipid Vesicles: Different Structural Requirements for Fusion and Leakage", *Biochemistry,* 1994, 33, 3201–3209.
Schlegel, R. and Wade, "A Synthetic Peptide Corresponding to the $NH_2$ Terminus of Vesicular Stomatitis Virus Glycoprotein is a pH–Dependent Hemolysin", *J. Biol. Chem.,* 1984, 259(8), 4691–4694.
Soukchareun, S. et al., "Preparation and Characterization of Antisense Oligonucleotide–Peptide Hybrids Containing Viral Fusion Peptides", *Bioconjugate Chem.,* 1995, 6, 43–53.
White, J., "Membrane Fusion", *Science,* 1992, 258, 917–924.
Yeagle, P. et al., "Effects of the "Fusion Peptide" From Measles Virus on the Structure of N–Methyl Dioleoylphosphatidylethanolamine Membranes and their Fusion with Sendai Virus", *Biochimica et Biophysica Acta,* 1991, 1065, 49–53.

(List continued on next page.)

Primary Examiner—Deborah Crouch
(74) Attorney, Agent, or Firm—Howson and Howson

(57) ABSTRACT

A method of delivering a multifunctional molecular complex for the transfer of a nucleic acid composition to a target cell is provided. The complex is comprised of a) said nucleic acid composition and b) a transfer moiety comprising 1) one or more cationic polyamines bound to said nucleic acid composition, 2) one or more endosome membrane disrupting components attached to at least one nitrogen of the polyamine and 3) one or more receptor specific binding components.

10 Claims, No Drawings

OTHER PUBLICATIONS

Atanasiu et al., "Virologie—Production de tumneurs chez le Hamster par inoculation d'acide desoxyribonucleique extrait de cultures de tissues infectees par le virus du polyome", *Academie des Sciences (Paris)*, 1962, 254, 4228–4230.

Barthel et al., "Laboratory Methods: Gene Transfer Optimization with Liposperimine–Coated DNA", *DNA and Cell Biol.*, 1993, 12, 553–560.

Behr et al., "Efficient Gene Transfer Into Mammalian Primary Endocrine Cells with Lipopolyamine–Caoted DNA", *Proc. Natl. Acad. Sci. USA*, 1989, 86, 6982–6986.

Bennett et al., "Cationic Lipids Enhance Cellular Uptake and Activity of Phosphorothioate Antisense Oligonucleotides", *Mol. Pharm.*, 1992, 41, 1023–1033.

Bodmer and Dean, "Carrier Potential of Glycoproteins", *Meth. Enzymol.*, 1985, 112, 298–306.

Bonfils et al., "Drug Targeting: Synthesis and Endocytosis of Oligonucleotide–Neoglycoprotein Conjugates", *Bioconj. Chem.*, 1992, 3, 277–284.

Bonfils et al., "Uptake by Macrophages of a Biotinylated Oligo–α–Deoxythymidylate by Using Mannosylated Streptavidin", *Nucl. Acids Res.*, 1992, 20, 4621–4629.

Chaudhary et al., "A Rapid Method of Cloning Functional Variable–Region Antibody Genes in *Escherichia coli* as Single–Chain Immunotoxins", *Proc. Natl. Acad. Sci. USA*, 1990, 87, 1066–1070.

Chu et al., "Efficiency of Cytoplasmic Delivery by pH–Sensitive Liposomes to Cells in Culture", Pharm. Res., 1990, 7, 824–854.

Citro et al., "Inhibition of Leukemia Cell Proliferation by Receptor–Mediated Uptake of c–myb Antisense Oligodeoxynucleotides", *Proc. Natl. Acad. Sci. USA*, 1992, 89, 7031–7035.

Cotten et al., "High–efficiency Receptor–Mediated Delivery of Small and Large (48 Kilobase Gene Constructs Using the Endosome–Disruption Activity of Defective or Chemically Inactivated Adenovirus Particles", *Proc. Natl. Acad. Sci. USA*, 1992, 89, 6094–6098.

Curiel et al., "Adenovirus Enhancement of Transferrin–Polylysine–Mediated Gene Delivery", *Proc. Nat. Acad. Sci. USA*, 1991, 88, 8850–8854.

Edgington, "Ribozymes: Stop Making Sense", Biotechnology, 1992, 10, 256–262.

Elofsson et al., "Solid–Phase Synthesis and Conformational Studies of Glycosylated Derivatives of Helper–T–Cell Immunogenic Peptides from Hen–Egg Lysozyme", *Carb. Res.*, 1993, 246, 89–103.

Felgner and Ringold, "Cationic Liposome–Mediated Transfection", *Nature*, 1989, 337, 387–388.

Felgner et al., "Enhanced Gene Delivery and Mechanism Studies with a Novel Series of Cationic Lipid Formulations", *J. Biol. Chem.*, 1994, 269, 2550–2561.

Gao et al., "Direct In Vivo Gene Transfer to Airway Epithelium Employing Adenovirus–Polylysine–DNA Complexes", *Human Gene Therapy*, 1993, 4, 17–24.

Haensler and Szoka, Jr., "Polyamidoamine Cascade Polymers Mediate Efficient Transfection of Cells in Culture", *Bioconj. Chem.*, 1993, 4, 372–379.

Haensler and Szoka, Jr. "Synthesis and Characterization of a Trigalactosylated Bisacridine Compound to Target DNA to Hepatocytes", *Bioconjugate Chem.*, 1993, 4, 85–93.

Howell et al., "Limited T–cell Receptor β–Chain Heterogeneity Among Interleukin 2 Receptor–Positive Synovial T Cells Suggests a Role for Superantigen in Rheumatoid Arthritis", *Proc. Natl. Acad. Sci. USA*, 1991, 88, 10921–10925.

Huckett et al., "Evidence for Targeted Gene Transfer by Receptor–Mediated Endocytosis", *Biochem. Pharmacol.*, 1990, 40, 253–263.

Israel et al., "Biological Activity of Polyoma Viral DNA in Mice and Hamsters", *J. Virol.*, 1979, 29, 990–96.

Juliano and Mayhew, "Interaction of Polynucleotides with Cultured Mammalian Cells", *Exp. Cell Res.*, 1972, 73, 3–12.

Kabanov et al., "Efficient Transformation of Mammalian Cells Using DNA Interpolyelectrolyte Complexes with Carbon Chain Polycations", *Bioconj. Chem.*, 1993, 4, 448–454.

Kawaguchi et al., "Differential Uptake of D–Galactosyl– and D–Glucosyl–neoglycoproteins by Isolated Rat Hepatocytes", *J. Biol. Chem.*, 1981, 256, 2230–2234.

Leamon and Low, "Delivery of Macromolecules into Living Cells: A Method that Exploits Folate Receptor Endocytosis", *Proc. Natl. Acad. Sci. USA*, 1991, 88, 5572–5576.

Lee et al., "Binding of Synthetic Oligosaccharides to the Hepatic Gal/GalNAc Lectin", *J. Biol. Chem.*, 1983, 258, 199–202.

Lee et al., "Synthesis of Some Cluster Glycosides Suitable for Attachment to Proteins as Solid Matrices", Carbohydrate Research, 1978, 67, 509–514.

Legendre and Szoka, Jr., "Cyclic Amphipathic Peptide–DNA Complexes Mediate High–Efficiency Transfection of Adherent Mammalian Cells", *Proc. Natl. Acad. Sci. USA*, 1993, 893–897.

Legendre and Szoka, Jr., "Delivery of Plasmid DNA into Mammalian Cell Lines Using pH–Sensitive Liposomes: Comparison with Cationic Liposomes", *Pharm. Res.*, 1992, 9, 1253–1242.

Lodish, "Recognition of Complex Oligosaccharides by the Multi–Subunit Asialoglycoprotein Receptor", TIBS, 1991, 16, 374–377.

Loeffler and Behr, "Gene Transfer into Primary and Established Mammalian Cell Lines with Lipopolyamine–Coated DNA", *Meth. Enzymol.*, 1993, 217, 599–618.

Mack et al, "Cationic Lipid Enhances In Vitro Receptor–Mediated Transfection", *Am. J. Med. Sci.*, 1994, 307, 138–143.

Mayhew and Juliano, "Interaction of Polynucleotides with Cultured Mammalian Cells", *Exp. Cell. Res.*, 1973, 77, 409–414.

Nagarajan and B.Ganem, "Chemistry of Naturally Occurring Polyamines. 9. Synthesis of Spermidine and Spermine Photoaffinity Labeling Reagents", *J. Org. Chem.*, 1985, 50, 5735–5737.

Oksenberg et al., "Limited Heterogeneity of Rearranged T–Cell Receptor Vα Transcripts in Brains of Multiple Sclerosis Patients", *Nature*, 1990, 345, 344–346.

Paliard et al., "Evidence for the Effects of a Superantigen in Rheumatoid Arthritis", *Science*, 1991, 253, 325–329.

Paolella et al., "Nuclease Resistant Ribozymes with High Catalytic Activity", *EMBO*, 1992, 1913–1919.

Perales et al., "Gene Transfer In Vivo: Sustained Expression and Regulation of Genes Introduced into the Liver by Receptor–Targeted Uptake", *Proc. Natl. Acad. Sci. USA*, 1994, 91, 4086–4090.

Plank et al., "Gene Transfer into Hepatocytes Using Asialoglycoprotein Receptor Mediated Endocytosis of DNA Complexed with an Artificial Tetra–Antennary Galactose Ligand", Bioconj. Chem., 1992, 3, 533–539.

Rose et al., "A New Cationic Liposome Reagent Mediating Nearly Quantitative Transfection of Animal Cells", BioTechniques, 1991, 10, 520–525.

Smith et al., "Liposomes as Agents of DNA Transfer", Biochim. Biophys. Acta, 1993, 1154, 327–340.

Subbarao et al., "pH–Dependent Bilayer Destabilization by an Amphipathic Peptide", J. Biol. Chem., 1987, 26, 2964–2972.

Trubetskoy et al., "Use of N–Terminal Modified Poly(L–lysine)–Antibody Conjugate as a Carrier for Targeted Gene Delivery in Mouse Lung Endothelial Cells", Bioconj. Chem., 1992, 3, 323–327.

Wagner et al., "Coupling of Adenovirus to Transferrin-polylysine/DNA Complexes Greatly Enhances Receptor–Mediated Gene Delivery and Expression of Transfected Genes", Proc. Natl. Acad. Sci. USA, 1992, 89, 6099–6103.

Wagner et al., "Influenza Virus Hemagglutinin HA–2 N–Terminal Fusogenic Peptides Augment Gene Transfer by Transferrin–Polylysine–DNA Complexes: Toward a Synthetic Virus–like Gene–Transfer Vehicle", Proc. Nat. Acad. Sci. USA, 1992, 89, 7934–7938.

Wagner et al., "Transferrin–polycation conjugates as Carriers for DNA Uptake into Cells", Proc. Natl. Acad. Sci. USA, 1990, 87, 3410–3414.

White et al., "Membrane Fusion Proteins of Enveloped Animal Viruses", Quarterly Reviews of Biophysics, 1983, 16, 151–195.

Will et al., "Cloned HBV DNA Causes Hepatitis in Chimpanzees", Nature, 1992, 299, 740–42.

Williams, W.V. et al., "Restricted Heterogeneity of T Cell Receptor Transcripts in Rheumatoid Synovium", J. Clin. Invest., 1992, 90, 326–333.

Wilson et al., "A Novel Mechanism for Achieving Transene Persistence in Vivo After Somatic Gene Transfer Into Hepatocytes", J. Biol. Chem., 1992, 267, 11483–11489.

Wood and Wetzel, "A Novel Method for the Incorporation of Glycoprotein–Derived Oligosaccharides into Neoglycopeptides", Bioconj. Chem., 1992, 3, 391–396.

Wu and Wu, "Evidence for Targeted Gene Delivery to Hep G2 Hepatoma Cells in Vitro", Biochem., 1988, 27, 887–892.

Wu and Wu, "Receptor–Mediated Gene Delivery and Expression in Vivo", J. Biol. Chem., 1988, 263, 14621–14624.

Wucherpfennig et al., "Shared Human T Cell Receptor Vβ Usage to Immunodominant Regions of Myeline Basic Protein", Science, 1990, 248, 1016–1019.

Yoshimura et al., "Adenovirus–mediated Augmentation of Cell Transfection with Unmodified Plasmid Vectors", J. Biol. Chem., 1993, 268, 2300–2303.

Zenke et al., "Receptor–Mediated Endocytosis of Transferrin–polycation Conjugates: An Efficient Way to Introduce DNA Into Hematopoietic Cells", Proc. Natl. Acad. Sci. USA, 1990, 87, 3655–3659.

Zhou and Huang, "DNA Transfection Mediated by Cationic Liposomes Containing Lipopolylysine: Characterization and Mechanism of Action", Biochim. Biophys. Acta, 1994, 1189, 195–203.

Remington's Pharmaceutical Sciences, A. Osol.

Sambrook et al., Molecular Cloning: A Laboratory Manual, Cold Spring Harbor, 1989.

P. Atanasiu et al., Academie des Sciences (Paris) 254, 4228–30 (1962).

M.A. Israel et al., J. Virol. 29, 990–96 (1979).

H. Will et al. Nature 299, 740–42 (1982).

J. L. Bodmer and R. T. Dean, Meth. Enzymol., 112,298–306 (1985).

H.F. Lodish, TIBS, 16, 374–77 (1991).

J.C. Perales et al Proc. Nat. Acad. Sci. USA, 91:4086–4090 (1994).

H. Basu et al, "Effects of Variation in the Structure of Spermine on the Association with DNA and the Induction of DNA Conformational Changes", Biochem. J., 269:329–334 (1990).

J–P. Behr, "Gene Transfer with Synthetic Cationic Amphiphiles: Prospects for Gene Therapy", Bioconjugate Chem., 5(5):382–3898 (1994).

H. Blau et al, "Molecular Medicine: Gene Therapy—A Novel Form of Drug Delivery", New Engl. J. Med., 333(18):1204–1207 (Nov. 2, 1995).

H. Gershon et al, "Mode of Formation and Structural Features of Dna—Cationic Liposome Complexes Used for Transfection", Biochemistry, 32(28):7143–7151 (1993).

R. Leventis et al, "Interactions of Mammalian Cells with Lipid Dispersions Containing Novel Metabolizable Cationic Amphiphiles", Biochimica et Biophysics Acta, 1023:124–132 (1990).

R. Malone et al, "Cationic Liposome–Mediated RNA Transfections", Proc. Natl. Acad. Sci. USA, 86:6077–6081 (Aug., 1989).

R. Mulligan, "The Basic Science of Gene Therapy", Science, 260:926–932 (May 14, 1993).

S. Orkin et al, "Report and Recommendations of the Panel to Assess the NIH Investment in Research on Gene Therapy", NIH Review Panel on Gene Therapy (Dec. 7, 1995).

P. Pinnaduwage et al, "A Positively Charged Liposome Used for the Efficient Delivery of DNA to Mouse L–Cells, an Alternative to Lipofectin", Biophysical J., 55:341a (1989), Abstract No. Tu–Pos232.

G. Plum et al, "Condensation of DNA by Trivalent Cations. 2. Effects of Cation Structure", Biopolymers, 30:631–643 (1990).

N. Schmid et al., "Location of Spermine and Othr Polyamines on DNA as Revealed by Photoaffinity Cleavage with Polyaminobenzenediazonium Salts", Biochemistry, 30(17):4357–4361 (1991).

L. Stamatatos et al., "Interactions of Cationic Lipid Vesicles with Negatively Charged Phospholipid Vesicles and Biological Membranes", Biochemistry, 27(11):3917–3925 (1988).

J. Zabner et al, "Cellular and Molecular Barriers to Gene Transfer by a Cationic Lipid", J. Biol. Chem., 270(32):18997–19007 (Aug. 11, 1995).

P. W. Berman, "Efficacy of Recombinant Glycoprotein D Subunit Vaccines on the Development of Primary, Recurrent, and Latent Genital Infections with Herpes Simplex Virus Type 2 in Guinea Pigs", J. Infect. Dis., 157(5):897–902 (May 1988).

* cited by examiner

SEQUENCE LISTING

<160> NUMBER OF SEQ ID NOS: 32

<210> SEQ ID NO 1
<211> LENGTH: 25
<212> TYPE: PRT
<213> ORGANISM: Vesicular stomatitis virus

<400> SEQUENCE: 1

Lys Phe Thr Ile Val Phe Pro His Asn Gln Lys Gly Asn Trp Lys Asn
 1               5                  10                  15

Val Pro Ser Asn Tyr His Tyr Cys Pro
            20                  25

<210> SEQ ID NO 2
<211> LENGTH: 32
<212> TYPE: PRT
<213> ORGANISM: Human immunodeficiency virus type 1

<400> SEQUENCE: 2

Ala Val Gly Ile Gly Ala Leu Phe Leu Gly Phe Leu Gly Ala Ala Gly
 1               5                  10                  15

Ser Thr Met Gly Ala Ala Ser Met Thr Leu Thr Val Gln Ala Arg Gln
            20                  25                  30

<210> SEQ ID NO 3
<211> LENGTH: 35
<212> TYPE: PRT
<213> ORGANISM: Murine leukemia virus

```
<400> SEQUENCE: 3

Glu Pro Val Ser Leu Thr Leu Ala Leu Leu Leu Gly Gly Leu Thr Met
 1               5                  10                  15

Gly Gly Ile Ala Ala Gly Val Gly Thr Gly Thr Thr Ala Leu Val Ala
                20                  25                  30

Thr Gln Gln
         35

<210> SEQ ID NO 4
<211> LENGTH: 23
<212> TYPE: PRT
<213> ORGANISM: Human immunodeficiency virus type 1

<400> SEQUENCE: 4

Ala Val Gly Ile Gly Ala Leu Phe Leu Gly Phe Leu Gly Ala Ala Gly
 1               5                  10                  15

Ser Thr Met Gly Ala Arg Ser
                20

<210> SEQ ID NO 5
<211> LENGTH: 17
<212> TYPE: PRT
<213> ORGANISM: Human immunodeficiency virus type 1

<400> SEQUENCE: 5

Ala Val Gly Ala Ile Gly Ala Leu Phe Leu Gly Phe Leu Gly Ala Ala
 1               5                  10                  15

Gly

<210> SEQ ID NO 6
<211> LENGTH: 22
<212> TYPE: PRT
<213> ORGANISM: Influenza virus

<400> SEQUENCE: 6

Gly Leu Phe Glu Ala Ile Ala Glu Phe Ile Glu Gly Gly Trp Glu Gly
 1               5                  10                  15

Leu Ile Glu Gly Cys Ala
                20

<210> SEQ ID NO 7
<211> LENGTH: 25
<212> TYPE: PRT
<213> ORGANISM: Influenza virus

<400> SEQUENCE: 7

Gly Leu Phe Gly Ala Ile Ala Gly Phe Ile Glu Asn Gly Trp Glu Gly
 1               5                  10                  15

Met Ile Asp Gly Trp Tyr Gly Phe Arg
                20                  25

<210> SEQ ID NO 8
<211> LENGTH: 23
<212> TYPE: PRT
<213> ORGANISM: Human immunodeficiency virus type 1

<400> SEQUENCE: 8

Ala Val Gly Ile Gly Ala Leu Phe Leu Gly Phe Leu Gly Ala Ala Gly
 1               5                  10                  15

Ser Thr Met Gly Ala Ala Ser
```

```
<210> SEQ ID NO 9
<211> LENGTH: 27
<212> TYPE: PRT
<213> ORGANISM: SV5 virus

<400> SEQUENCE: 9

Phe Ala Gly Val Val Ile Gly Leu Ala Ala Leu Gly Val Ala Thr Ala
 1               5                  10                  15
Ala Asn Val Thr Ala Ala Val Ala Leu Val Lys
            20                  25

<210> SEQ ID NO 10
<211> LENGTH: 19
<212> TYPE: PRT
<213> ORGANISM: SFV virus

<400> SEQUENCE: 10

Lys Val Tyr Thr Gly Val Tyr Pro Phe Met Trp Gly Gly Ala Tyr Cys
 1               5                  10                  15
Phe Cys Asp

<210> SEQ ID NO 11
<211> LENGTH: 23
<212> TYPE: PRT
<213> ORGANISM: PH-30 virus

<400> SEQUENCE: 11

Lys Leu Ile Cys Thr Gly Ile Ser Ser Ile Pro Pro Ile Arg Ala Leu
 1               5                  10                  15
Phe Ala Ala Ile Asn Ile Pro
            20

<210> SEQ ID NO 12
<211> LENGTH: 22
<212> TYPE: PRT
<213> ORGANISM: Sendai virus

<400> SEQUENCE: 12

Phe Phe Gly Ala Val Ile Gly Thr Ile Ala Leu Gly Val Ala Thr Ala
 1               5                  10                  15
Thr Ala Ala Gln Ile Thr
            20

<210> SEQ ID NO 13
<211> LENGTH: 22
<212> TYPE: PRT
<213> ORGANISM: SV5 virus

<400> SEQUENCE: 13

Phe Ala Gly Val Val Ile Gly Leu Ala Ala Leu Gly Val Ala Thr Ala
 1               5                  10                  15
Thr Ala Ala Gln Val Thr
            20

<210> SEQ ID NO 14
<211> LENGTH: 22
<212> TYPE: PRT
<213> ORGANISM: NDV virus

<400> SEQUENCE: 14
```

```
Phe Ile Gly Ala Ile Ile Gly Gly Val Ala Leu Gly Val Ala Thr Ala
 1               5                  10                  15

Thr Ala Ala Gln Ile Thr
            20

<210> SEQ ID NO 15
<211> LENGTH: 28
<212> TYPE: PRT
<213> ORGANISM: Influenza virus

<400> SEQUENCE: 15

Gly Leu Phe Gly Ala Ile Ala Gly Phe Ile Glu Asn Gly Trp Glu Gly
 1               5                  10                  15

Met Ile Asp Gly Trp Tyr Gly Phe Arg His Gln Asn
            20                  25

<210> SEQ ID NO 16
<211> LENGTH: 28
<212> TYPE: PRT
<213> ORGANISM: Influenza virus

<400> SEQUENCE: 16

Gly Leu Phe Gly Ala Ile Ala Gly Phe Ile Glu Asn Gly Trp Glu Gly
 1               5                  10                  15

Leu Val Asp Gly Trp Tyr Gly Phe Arg His Gln Asn
            20                  25

<210> SEQ ID NO 17
<211> LENGTH: 28
<212> TYPE: PRT
<213> ORGANISM: Influenza virus

<400> SEQUENCE: 17

Gly Phe Phe Gly Ala Ile Ala Gly Phe Leu Glu Gly Gly Trp Glu Gly
 1               5                  10                  15

Met Ile Ala Gly Trp His Gly Tyr Thr Ser His Gly
            20                  25

<210> SEQ ID NO 18
<211> LENGTH: 30
<212> TYPE: PRT
<213> ORGANISM: MMTV virus

<400> SEQUENCE: 18

Phe Val Ala Ala Ile Ile Leu Gly Ile Ser Ala Leu Ile Ala Ile Ile
 1               5                  10                  15

Thr Ser Phe Ala Val Ala Thr Thr Ala Leu Val Lys Glu Met
            20                  25                  30

<210> SEQ ID NO 19
<211> LENGTH: 53
<212> TYPE: PRT
<213> ORGANISM: MoMLV virus

<400> SEQUENCE: 19

Glu Pro Val Ser Leu Thr Leu Ala Leu Leu Leu Gly Gly Leu Thr Met
 1               5                  10                  15

Gly Gly Ile Ala Ala Gly Ile Gly Thr Gly Thr Thr Ala Leu Met Ala
            20                  25                  30

Thr Gln Gln Phe Gln Gln Leu Gln Ala Ala Val Gln Asp Asp Leu Arg
            35                  40                  45
```

Glu Val Glu Lys Ser
    50

<210> SEQ ID NO 20
<211> LENGTH: 53
<212> TYPE: PRT
<213> ORGANISM: F-MuLV virus

<400> SEQUENCE: : 20

Glu Pro Val Ser Leu Thr Leu Ala Leu Leu Leu Gly Gly Leu Thr Met
1               5                    10                15

Gly Gly Ile Ala Ala Gly Val Gly Thr Gly Thr Thr Ala Leu Val Ala
                    20                    25                    30

Thr Gln Gln Phe Gln Gln Leu His Ala Ala Val Gln Asp Asp Leu Lys
           35                    40                    45

Glu Val Glu Lys Ser
    50

<210> SEQ ID NO 21
<211> LENGTH: 53
<212> TYPE: PRT
<213> ORGANISM: AKV virus

<400> SEQUENCE: 21

Glu Pro Val Ser Leu Thr Leu Ala Leu Leu Leu Gly Gly Leu Thr Met
1               5                    10                15

Gly Gly Ile Ala Ala Gly Val Gly Thr Gly Thr Thr Ala Leu Val Ala
                    20                    25                    30

Thr Gln Gln Phe Gln Gln Leu Gln Ala Ala Met His Asp Asp Leu Lys
           35                    40                    45

Glu Val Glu Lys Ser
    50

<210> SEQ ID NO 22
<211> LENGTH: 27
<212> TYPE: PRT
<213> ORGANISM: SFV virus

<400> SEQUENCE: 22

Asp Tyr Gln Cys Lys Val Tyr Thr Gly Val Tyr Pro Phe Met Trp Gly
1               5                    10                15

Gly Ala Tyr Cys Phe Cys Asp Ser Glu Asn Thr
                    20                    25

<210> SEQ ID NO 23
<211> LENGTH: 27
<212> TYPE: PRT
<213> ORGANISM: Sindbis virus

<400> SEQUENCE: 23

Asp Tyr Thr Cys Lys Val Phe Gly Gly Val Tyr Pro Phe Met Trp Gly
1               5                    10                15

Gly Ala Gln Cys Phe Cys Asp Ser Glu Asn Ser
                    20                    25

<210> SEQ ID NO 24
<211> LENGTH: 19
<212> TYPE: PRT
<213> ORGANISM: Measles virus

<400> SEQUENCE: 24

Phe Ala Gly Val Val Leu Ala Gly Ala Ala Leu Gly Val Ala Ala Ala
 1               5                  10                  15

Ala Gln Ile

<210> SEQ ID NO 25
<211> LENGTH: 19
<212> TYPE: PRT
<213> ORGANISM: Measles virus

<400> SEQUENCE: 25

Phe Ala Gly Val Val Leu Ala Gly Ala Ala Leu Gly Val Ala Thr Ala
 1               5                  10                  15

Ala Gln Ile

<210> SEQ ID NO 26
<211> LENGTH: 23
<212> TYPE: PRT
<213> ORGANISM: Influenza virus

<400> SEQUENCE: 26

Gly Leu Phe Gly Ala Ile Ala Gly Phe Ile Glu Asn Gly Trp Glu Gly
 1               5                  10                  15

Met Ile Asp Gly Gly Gly Cys
            20

<210> SEQ ID NO 27
<211> LENGTH: 20
<212> TYPE: PRT
<213> ORGANISM: Influenza virus

<400> SEQUENCE: 27

Gly Leu Phe Gly Ala Ile Ala Gly Phe Ile Glu Asn Gly Trp Glu Gly
 1               5                  10                  15

Met Ile Asp Gly
            20

<210> SEQ ID NO 28
<211> LENGTH: 20
<212> TYPE: PRT
<213> ORGANISM: Influenza virus

<400> SEQUENCE: 28

Gly Ile Phe Gly Ala Ile Ala Gly Phe Ile Glu Asn Gly Trp Glu Gly
 1               5                  10                  15

Met Ile Asp Gly
            20

<210> SEQ ID NO 29
<211> LENGTH: 20
<212> TYPE: PRT
<213> ORGANISM: Influenza virus

<400> SEQUENCE: 29

Gly Leu Phe Gly Ala Ile Ala Gly Phe Ile Glu Gly Gly Trp Thr Gly
 1               5                  10                  15

Met Ile Asp Gly
            20

<210> SEQ ID NO 30
<211> LENGTH: 20
<212> TYPE: PRT
<213> ORGANISM: Influenza virus

```
<400> SEQUENCE: 30

Gly Leu Phe Gly Ala Ile Ala Gly Phe Ile Glu Gly Gly Trp Glu Gly
1               5                   10                  15

Met Val Asp Gly
            20

<210> SEQ ID NO 31
<211> LENGTH: 20
<212> TYPE: PRT
<213> ORGANISM: Influenza virus

<400> SEQUENCE: 31

Gly Leu Phe Gly Ala Ile Ala Gly Phe Ile Glu Gly Gly Trp Glu Gly
1               5                   10                  15

Leu Val Asp Gly
            20

<210> SEQ ID NO 32
<211> LENGTH: 20
<212> TYPE: PRT
<213> ORGANISM: Influenza virus

<400> SEQUENCE: 32

Gly Phe Phe Gly Ala Ile Ala Gly Phe Leu Glu Gly Gly Trp Glu Gly
1               5                   10                  15

Met Ile Ala Gly
            20
```

MULTIFUNCTIONAL COMPLEXES FOR GENE TRANSFER INTO CELLS COMPRISING A NUCLEIC ACID BOUND TO A POLYAMINE AND HAVING AN ENDOSOME DISRUPTION AGENT

This is a divisional of U.S. patent application Ser. No. 08/809,397, filed Mar. 21, 1997, now U.S. Pat. No. 6,127,170, issued Oct. 3, 2000, which is a 35 USC §371 of PCT/US95/12502, filed Sep. 28, 1995, which is a CIP of U.S. patent application Ser. No. 08/314,060, filed Sep. 28, 1994, now U.S. Pat. No. 5,837,533, issued Nov. 17, 1998.

BACKGROUND OF THE INVENTION

1. Field of the Invention

The present invention is in the field of methods for the transfer of genetic information, e.g., foreign DNA, into target cells, especially eukaryotic cells. In particular, the present invention relates to nonviral gene carriers comprising multifunctional molecular conjugates which include, inter alia, lipopolyamines of a particular configuration, a component which promotes endosome disruption, and a receptor specific binding component. The present application is related to U.S. Ser. No. 08/314,060 filed Sep. 28, 1994 and entitled "Multifunctional molecular complexes for gene transfer to cells" which is incorporated herein by reference.

Heretofore, viral vectors of various types have been successfully utilized for the insertion of selected foreign genetic information into a target cell, and in the case of eukaryotic cells, for incorporation of that genetic information into the genome of the cell. These viral vector systems have relied upon the molecular machinery of the virus, evolved over time to surmount the significant problems facing a virus in attempting to invade, i.e., infect a cell. Despite the efficiency of such viral vectors, however, there has been continued concern regarding the safety of using viruses, particularly from the standpoint of undesired side effects. Thus, there has been an ongoing effort to develop non-viral gene delivery systems that are as efficient as viral vectors, but with an improved safety profile.

Nonviral vectors or carriers, of the type with which the present invention is concerned, will thus have to overcome the same obstacles as a viral vector. The problems faced by such carriers include persistence in the biophase of the organism for a sufficient time to reach the target cell; recognition of the target cell and means for mediating transport of the genetic material through the cell membrane and into the cytoplasm of the cell; avoidance of degradation within the cell by the reticuloendothelial system; and transport to and through the nuclear membrane into the nucleus of the cell where transcription of the genetic material can take place.

It is to overcoming the problems described above that the present invention is addressed; and since the problems are several and different, the present invention comprises a multifunctional complex, i.e., a molecular conjugate of various ligands intended to surmount specific obstacles.

The ultimate usefulness of gene transfer techniques is of enormous potential benefit in a number of areas. The transfer of genetic material into cells is the basis of a number of processes now widely accepted in the areas of molecular biology, gene therapy and genetic immunization. Transfer of the genetic information encoded in DNA to cells where it expresses identified individual proteins, has permitted investigation of the function of such proteins on a cellular level, and of the underlying cell physiology. Genetic material has also been transferred into cells to introduce proteins that are absent due to an inherent genetic flaw in the cell that expresses an inactive protein or else prevents expression of the protein altogether. The transfer of genetic material into cells can be used to prevent the expression of proteins in those cells through the well-known antisense effect of complementary DNA or RNA strands.

Exogenous, i.e., foreign genetic material can permit cells to synthesize significant amounts of proteins that are not available by other means in practical economic terms. These proteins of interest can be grown in a variety of host cells such as yeast, bacterial or mammalian cells. Genetic material can also be used to provide protective immune responses in vivo by injection of DNA that encodes immunogenic proteins, i.e., ones that can stimulate the desired immune response. The in vivo introduction of exogenous genetic material into cells also has potential utility in applications for the alleviation, treatment or prevention of metabolic, tumoral or infectious disorders by the same mechanisms enumerated above.

2. Description of the Prior Art

It is possible to transfer genetic material into target cells without the use of vectors or carriers. For example, genetic material can be introduced systemically through an intravenous or intraperitoneal injection for in vivo applications, or can be introduced to the site of action by direct injection into that area. For example, it has long been recognized that DNA, by itself, injected into various tissues, will enter cells and produce a protein that will elicit an immune response. See, e.g., P. Atanasiu et al., Academie des Sciences (Paris) 254, 4228–30 (1962); M. A. Israel et al., J. Virol. 29, 990–96 (1979); H. Will et al., Nature, 299, 740–42 (1982); H. Robinson, World Patent Application WO 86/00930, published Feb. 13, 1986; P. L. Felgner, J. A. Wolff, G. H. Rhodes, R. W. Malone and D. A. Carson, World Patent Application WO 90/11092, published Oct. 4, 1990; and R. J. Debs and N. Zhu, World Patent Application WO 93/24640 published Dec. 9, 1993. However, DNA by itself is hydrophilic, and the hydrophobic character of the cellular membrane poses a significant barrier to the transfer of DNA across it. Accordingly, it has become preferred in the art to use facilitators that enhance the transfer of DNA into cells on direct injection.

Another approach in the art to delivery of genetic material to target cells is one that takes advantage of natural receptor-mediated endocytosis pathways that exist in such cells. Several cellular receptors have been identified heretofore as desirable agents by means of which it is possible to achieve the specific targeting of drugs, and especially macromolecules and molecular conjugates serving as carriers of genetic material of the type with which the present invention is concerned. These cellular receptors allow for specific targeting by virtue of being localized to a particular tissue or by having an enhanced avidity for, or activity in a particular tissue. See, e.g., J. L. Bodmer and R. T. Dean, Meth. Enzymol., 112, 298–306 (1985). This affords the advantages of lower doses or significantly fewer undesirable side effects.

One of the better known examples of a cell and tissue selective receptor is the asialoglycoprotein receptor present in hepatocytes. The asialoglycoprotein receptor is an extracellular receptor with a high affinity for galactose, especially tri-antennary oligosaccharides, i.e., those with three somewhat extended chains or spacer arms having terminal galactose residues; see, e.g., H. F. Lodish, TIBS, 16, 374–77 (1991). This high affinity receptor is localized to hepatocytes and is not present in Kupffer cells; allowing for a high degree of selectivity in delivery to the liver.

It has also been proposed in the art of receptor-mediated gene transfer that in order for the process to be efficient in vivo, the assembly of the DNA complex should result in condensation of the DNA to a size suitable for uptake via an endocytic pathway. See, e.g., J. C. Perales, T. Ferkol, H. Beegen, O. D. Ratnoff, and R. W. Hanson, *Proc. Nat. Acad. Sci. USA*, 91, 4086–4090 (1994).

An alternative method of providing cell-selective binding is to attach an entity with an ability to bind to the cell type of interest; commonly used in this respect are antibodies which can bind to specific proteins present in the cellular membranes or outer regions of the target cells. Alternative receptors have also been recognized as useful in facilitating the transport of macromolecules, such as biotin land folate receptors; see P. S. Low, M. A. Horn and P. F. Heinstein, World Patent Application Wo 90/12095, published Oct. 18, 1990; P. S. Low, M. A. Horn and P. F. Heinstein, World Patent; Application WO 90/12096, published Oct. 18, 1990; P. S. Low, M. A. Horn and P. F. Heinstein, U.S. Pat. No. 5,108,921, Apr. 28, 1992; C. P. Leamon and P. S. Low, Proc. Nat. Acad. Sci. USA, 88, 5572–5576 (1991); transferrin receptors; insulin receptors; and mannose receptors (see further below). The enumerated receptors are merely representative, and other examples will readily come to the mind of the artisan.

The conjugation of different functionalities on the same molecule has also been utilized in the art. For example, in 1988 G. Y. Wu and C. M. Wu, J. Biol. Chem., 263, 14621–14624 (1988) described a method for cellular receptor mediated delivery of DNA to hepatocytes. This method was further described in G. Y. Wu and C. H. Wu, Biochem., 27, 887–892 (1988); G. Y. Wu and C. H. Wu, U.S. Pat. No. 5,166,320, Nov. 24, 1992; and G. Y. Wu and C. H. Wu, World Patent Application WO 92/06180, published Apr. 16, 1992. The method consists of attaching a glycoprotein, asialoorosomucoid, to poly-lysine to provide a hepatocyte selective DNA carrier. The function of the poly-lysine is to bind to the DNA through ionic interactions between the positively charged (cationic) ε amino groups of the lysines and the negatively charged (anionic) phosphate groups of the DNA. Orosomucoid is a glycoprotein which is normally present in human serum. Removal of the terminal sialic acid (N-acetyl neuraminic acid) from the branched oligosaccharides exposes terminal galactose oligosaccharides, for which hepatocyte receptors have a high affinity, as already described.

After binding to the asialoglycoprotein receptor on hepatocytes, the protein is taken into the cell by endocytosis into a pre-lysosomal endosome. The DNA, ionically bound to the poly-lysine-asialoorosomucoid carrier, is also taken into the endosome. Additional work using this delivery system,. e.g., that done by J. M. Wilson, M. Grossman, J. A. Cabrera, C. H. Wu and G. Y. Wu, J. Biol. Chem, 267, 11483–11489 (1992), has found that partial hepatectomy improves the persistence of the expression of the DNA delivered into the hepatocytes. The transfer of the DNA into cells by this mechanism is also significantly enhanced by the addition of cationic lipids; see, e.g., K. D. Mack, R. Walzem and J. B. Zeldis, Am. J. Med. Sci., 307, 138–143 (1994).

The use of a specific asialoglycoprotein is not required to achieve binding to the asialoglycoprotein receptor; this binding can also be accomplished with high affinity by the use of small, synthetic molecules having a similar configuration. The carbohydrate portion can be removed from an appropriate glycoprotein and be conjugated to other macromolecules; see, e.g., S. J. Wood and R. Wetzel, Bioconj. Chem., 3, 391–396 (1992). By this procedure the cellular receptor binding portion of the glycoprotein is removed, and the specific portion required for selective cellular binding can be transferred to another molecule.

There is a ample literature on the preparation of synthetic glycosides which can be attached to macromolecules and confer on them the ability to bind to the corresponding galactose specific receptor. The importance of branched glycosides was recognized early; see Y. C. Lee, Carb. Res., 67, 509–514 (1978). Further work delineated that sugar density [K.Kawaguchi, M.Kuhlenschmidt, S.Roseman and Y. C. Lee, J. Biol. Chem., 256,2230–2234 (1981)] and spacial relationships [Y. C. Lee, R. R. Townsend, M. R. Hardy, J. Lonngren, J. Arnarp, M. Haraldsson and H. Lonn, J. Biol. Chem., 258, 199–202 (1983)] are important determinants of binding potency. Reductive amination of a peptide with a branched tri-lysine amino terminus gives a ligand ending with four galactosyl residues that can be readily coupled to poly-lysine or other macromolecules; see C. Plank, K. Zatlouhal, M. Cotten, K. Mechtler and E. Wagner, Bioconj. Chem., 3,533–539(1992); and has been used to prepare DNA constructs.

Thiopropionate and thiohexanoate glycosidic derivatives of galactose have been prepared and linked to L-lysyl-L-lysine to form a synthetic tri-antennary galactose derivative. A bisacridine spermidine derivative containing this synthetic tri-antennary galactose has been used to target DNA to hepatocytes; see F. C. Szoka, Jr and J. Haensler, World Pat Application WO 93/19768, published Oct. 14, 1993; and J. Haensler and F. C. Szoka, Jr., Bioconj. Chem., 4, 85–93 (1993).

Other means of providing cellular receptor based facilitation of gene transfer into cells using poly-lysine as a carrier have been described in the art. Antibodies specific for cell surface thrombomodulin have been used with poly-lysine as a delivery system for DNA in vitro and in vivo; see V. S. Trubetskoy, V. P. Torchilin, S. J. Kennel and L. Huang, Biocon;. Chem., 3, 323–327 (1992). The transferrin receptor has also been used to target DNA to erythroblasts, K562 macrophages and ML-60 leukemic cells; see E. Wagner, M. Zenke, M. Cotten, H. Beug and M. L. Birnstiel, Proc. Nat. Acad. Sci. USA, 87, 3410–3414 (1990); M. Zenke, P. Steinlein, E. Wagner, M. Cotten, H. Beug and M. L. Birnstiel, Proc. Nat. Acad. Sci. USA, 87, 3655–3659 (1990); and G. Citro, D. Perrotti, C. Cucco, I. D'Agnano, A. Sacchi, G. Zupi and B. Calabretta, Proc. Nat. Acad. Sci. USA, 89, 7031–7035 (1990). These studies used both small oliogodeoxynucleotides as well as large plasmids.

The ability of poly-lysine to facilitate DNA entry into cells is significantly enhanced if the poly-lysine is chemically modified with hydrophobic appendages; see X. Zhou and L. Huang, Biochim. Biophys. Acta, 1189, 195–203 (1994); complexed with cationic lipids; see K. D. Mack, R. Walzem and J. B. Zeldis, Am. J. Med. Sci., 307, 138–143 (1994) or associated with viruses. Many viruses infect specific cells by receptor mediated binding and insertion of the viral DNA/RNA into the cell; and thus this action of the virus is similar to the facilitated..entry of DNA described above.

Replication-incompetent adenovirus has been used to enhance the entry of transferrin-poly-lysine complexed DNA into cells; see D. T. Curiel, S. Agarwal, E. Wagner and M. Cotten, Proc. Nat. Acad. Sci. USA, 88, 8850–8854 (1991); E. Wagner, K. Zatloukal, M. Cotten, H. Kirlappos, K. Mechtler, D. T. Curiel and M. L. Birnstiel, Proc. Nat. Acad. Sci. USA, 89, 6099–6103 (1992); M. Cotten, E. Wagner, K. Zatloukal, S. Phillips, D. T. Curiel and M. L. Birnstiel, Proc. Nat. Acad. Sci. USA, 89, 6094–6098 (1992); and L. Gao, E. Wagner, M. Cotten, S. Agarwal, C. Harris, M. Romer, L. Miller, P.-C. Hu and D. Curiel, Hum. Gene Ther., 4, 17–24 (1993). The adenovirus enhances the entry of the poly-lysine-transferrin-DNA complex when covalently attached to the poly-lysine and when attached through an antibody binding site. There does not need to be a direct attachment of the adenovirus to the poly-lysine-transferrin-DNA complex, and it can facilitate the entry of the complex when present as a simple mixture. The poly-lysine transferrin-DNA complex provides receptor specific binding to the cells and is internalized into endosomes along with the DNA. Once inside the endosomes, the adenovirus facilitates entry of the DNA/transferrin-poly-lysine complex into the cell by disruption of the endosomal compartment with subsequent release of the DNA into the cytoplasm. Replication-incompetent adenovirus has also been used to enhance the entry of uncomplexed DNA plasmids into cells without the benefit of the cell receptor selectivity conferred by the poly-lysine-transferrin complex; see K. Yoshimura, M. A. Rosenfeld, P. Seth and R. G. Crystal, J. Biol. Chem., 268, 2300–2303 (1993).

Synthetic peptides such as the N-terminus region of the influenza hemagglutinin protein are known to destabilize membranes and are known as fusogenic peptides. Conjugates containing the influenza fusogenic peptide coupled to poly-lysine together with a peptide having a branched tri-lysine amino terminus ligand ending with four galactosyl residues have been prepared as facilitators of DNA entry into hepatocytes; see C. Plank, K. Zatlouhal, M. Cotten, K. Mechtler and E. Wagner, Bioconj. Chem., 3,533 –539 (1992). These conjugates combine the asialoglycoprotein receptor mediated binding conferred by the tetra-galactose peptide, the endosomal disrupting abilities of the influenza fusogenic peptide, and the DNA binding of the poly-lysine. These conjugates deliver DNA into the cell by a combination of receptor mediated uptake and internalization into endosomes. This internalization is followed by disruption of the endosomes by the influenza fusogenic peptide to release the DNA into the cytoplasm. In a similar fashion, the influenza fusogenic peptide can be attached to poly-lysine and mixed with the transferrin-poly-lysine complex to provide a similar DNA carrier selective for cells carrying the transferrin receptor; see E. Wagner, C. Plank, K. Zatloukal, M. Cotten and M. L. Birnstiel, Proc. Nat. Acad. Sca. USA, 89, 7934–7938 (1992). Synthetically designed peptides can also be used; for example the "GALA" peptides [N. K. Subbarao, R. A. Parente, F. C. Szoka, Jr, L. Nadasdi and K. Pongracz, J. Biol. Chem., 26, 2964–2972 (1987)] have been coupled to DNA carriers and an enhanced facilitated entry into cells was observed [J. Haensler and F. C. Szoka, Jr., Bioconj. Chem., 4, 372–379 (1993)]. The cationic amphipathic peptide gramicidin S can facilitate entry of DNA into cells [J.-Y. Legendre and F. C. Szoka, Jr., Proc. Nat. Acad. Sci. USA, 90, 893–897 (1993)], but also requires a phospholipid to achieve significant transfer of DNA.

Poly-lysine is not unique in providing a polycationic framework for the entry of DNA into cells. DEAE-dextran has also been shown to be effective in promoting RNA and DNA entry into cells; see R. Juliano and E. Mayhew, Exp. Cell. Res. 73, 3–12 (1972); and E. Mayhew and R. Juliano, Exp. Cell. Res. 77, 409–414 (1973). More recently, a dendritic cascade co-polymer of ethylenediamine and methyl acrylate has been shown to be useful in providing a carrier of DNA which facilitates entry into cells; see J. Haensler and F. C. Szoka, Jr., Bioconj. Chem., 4, 372–379 (1993). An alkylated polyvinylpyridine polymer has also been used to facilitate DNA entry into cells; see A. V. Kabanov, I. V. Astafieva, I. V. Maksimova, E. M. Lukanidin, G. P. Georgiev and V. A. Kabanov, Bioconj. Chem., 4, 448–454 (1993).

Positively charged liposomes have also been widely used as carriers of DNA which facilitate entry into cells; see, e.g., F. C. Szoka, Jr. and J. Haensler, World Pat Application WO 93/19768, published Oct. 14, 1993; R. J. Debs and N. Zhu, World Patent Application WO 93/24640, published Dec. 9, 1993; P. L. Felgner, R. Kumar, C. Basava, R. C. Border and J.-Y. Hwang-Felgner, World Patent Application WO 91/16024, published Oct. 31, 1991; P. L. Felgner and G. M. Ringold, Nature, 337, 387–388 (1989); J. K. Rose, L. Buonocore and M. A. Whitt, BioTechniques, 10, 520–525 (1991); C. F. Bennett, M. Y. Chiang, H. Chan, J. E. E. Schoemaker and C. K. Mirabelli, Mol. Pharm. 41, 1023–1033 (1992); J. H. Felgner, R. Kumar, C. N. Sridhar, C. J. Wheeler, Y. J. Tsai, R. Border, P. Ramsey, M. Martin and P. L. Felgner, J. Biol. Chem., 269, 2550–2561 (1994); J. G. Smith, R. L. Walzem and J. B. German, Biochim. Biophys. Acta, 1154, 327–340 (1993). These carrier compositions have also included pH sensitive liposomes; see C.-J. Chu, J. Dijkstra, M.-Z. Lai, K. Hong and F. C. Szoka, Jr., Pharm. Res., 7, 824–854 (1990); J.-Y. Legendre and F. C. Szoka, Jr., Pharm. Res., 9, 1253–1242 (1992).

A poly-cationic lipid has been prepared by coupling dioctadecylamidoglycine and dipalmitoyl phosphatidylethanolamine to a 5-carboxyspermine; see J.-P. Behr, B. Demeniex, J.-P. Loeffler and J. Perez-Mutul, Proc. Nat. Acad. Sci. USA, 86, 6982–6986 (1989); F. Barthel, J.-S. Remy, J.-P. Loeffler and J. P. Behr, DNA and Cell Biol., 12, 553–560 (1993); J.-P. Loeffler and J.-P. Behr, Meth. Enzymol., 217, 599–618 (1993); J.-P. Behr and J.-P. Loeffler, U.S. Pat. No. 5,171,678, Dec. 15, 1992. These lipophilic-spermines are very active in transferring DNA through cellular membranes.

Combinations of lipids have been used to facilitate the transfer of nucleic acids into cells. For example, in U.S. Pat. No. 5,283,185 there is disclosed such a method which utilizes a mixed lipid dispersion of a cationic lipid with a co-lipid in a suitable solvent. The lipid has a structure which includes a lipophilic group derived from cholesterol, a linker bond, a linear alkyl spacer arm, and a cationic amino group; and the co-lipid is phosphatidylcholine or phosphatidylethanolamine.

Macrophages have receptors for both mannose and mannose-6-phosphate which can bind to and internalize molecules displaying these sugars. The molecules are internalized by endocytosis into a pre-lysosomal endosome. This internalization has been used to enhance entry of oligonucleotides into macrophages using bovine serum albumin modified with mannose-6-phosphate and linked to an oligodeoxynucleotide by a disulfide bridge to a modified 3' end; see E. Bonfils, C. Depierreux, P. Midoux, N. T. Thuong, M. Monsigny and A. C. Roche, Nucl. Acids Res. 20, 4621–4629 (1992). Similarly, oligodeoxynucleotides modified at the 3' end with biotin were combined with mannose-modified streptavidin, and were also found to have facilitated entry into macrophages; see E. Bonfils, C. Mendes, A. C. Roche, M. Monsigny and P. Midoux, Bioconj. Chem., 3, 277–284 (1992).

Various peptides and proteins, many of which are naturally occurring, have been shown to have receptors on cell surfaces, that once they are attached thereto, allow them to become internalized by endocytosis. Materials bound to these receptors are delivered to endosomal compartments inside the cell. Examples include insulin, vasopressin, low density lipoprotein, epidermal growth factor and others. This internalization has also been used to facilitate entry of DNA into cells; e.g., insulin has been conjugated to polylysine to provide facilitated DNA entry into cells possessing an insulin receptor; see B. Huckett, M. Ariatti and A. O. Hawtrey, Biochem. Pharmacol., 40, 253–263 (1990).

SUMMARY OF THE INVENTION

The present invention relates to a multifunctional molecular complex for the transfer of a nucleic acid composition to a target cell comprising in any functional combination: 1) said nucleic acid composition; 2) one or more cationic polyamine components bound to said nucleic acid composition, each comprising from three to twelve nitrogen atoms; 3) one or more endosome membrane disruption promoting components attached to at least one nitrogen atom of at least one of said polyamine components, through an alkyl, carboxamide, carbamate, thiocarbamate, or carbamoyl bridging group, comprising a) at least one lipophilic long chain alkyl group, b) a fusogenic peptide comprising spike glycoproteins of enveloped animal viruses, or c) cholic acid or cholesteryl or derivatives; and optionally 4) one or more receptor specific binding components which are ligands for natural receptors of said target cell, attached through an alkyl, carboxamide, carbamate, thiocarbamate, or carbamoyl bridging group to either a) a further nitrogen atom of at least one of said polyamine components to which said one or more endosome membrane disruption promoting components is attached, or b) a nitrogen atom of at least one further polyamine component which does not have attached thereto any endosome membrane disruption promoting component. The present invention further relates to a self-assembling delivery system for the transfer of a nucleic acid composition to a target cell comprising the following separate components capable of being brought together and chemically joined into a molecular complex by simple mixing: A) said nucleic acid composition to be transferred; and B) a delivery vehicle, referred to herein as the "transfer moiety", comprising a) one or more cationic polyamine components which will bind, i.e., which are capable of being bound to said nucleic acid composition, each comprising from three to twelve nitrogen atoms; b) one or more endosome membrane disruption promoting components attached to at least one nitrogen atom of at least one of said polyamine components, through an alkyl, carboxamide, carbamate, thiocarbamate, or carbamoyl bridging group, comprising i) at least one lipophilic long chain alkyl group, ii) a fusogenic peptide comprising spike glycoproteins of enveloped animal viruses, or iii) cholic acid or cholesteryl or derivatives; and optionally 4) one or more receptor specific binding components which are ligands for natural receptors of said target cell, attached through an alkyl, carboxamide, carbamate, thiocarbamate, or carbamoyl bridging group to either a) a further nitrogen atom of at least one of said polyamine components to which said one or more endosome membrane disruption promoting components is attached, or b) a nitrogen atom of at least one further polyamine component which does not have attached thereto any endosome membrane disruption promoting component.

The present invention also includes the transfer moiety, described in detail immediately above, as a separate composition of matter.

The present invention also relates to a method for the transfer of a nucleic acid composition to target cells on an in vitro basis. The method comprises the step of contacting said target cells with a multifunctional molecular complex which includes said nucleic acid composition, as detailed further above, thereby transferring to said cells, a nucleic acid molecule that comprises a nucleotide sequence that either encodes a desired peptide or protein, or serves as a template for functional nucleic acid molecules. The desired protein or functional nucleic acid molecule may be any product of industrial, commercial or scientific interest, e.g., therapeutic agents including vaccines; foodstuffs and nutritional supplements; compounds of agricultural significance such as herbicides and plant growth regulants, insecticides, miticides, rodenticides, and fungicides; compounds useful in animal health such as parasiticides including nematocides; and so forth. The target cells are typically cultures of host cells comprising microorganism cells such as bacteria and yeast, but may also include plant and mammalian cells. The cell cultures are maintained in accordance with fermentation techniques well known in the art, which maximize production of the desired protein or functional nucleic acid molecule, and the fermentation products are harvested and purified by known methods.

The present invention further relates to a method for the transfer of a nucleic acid composition to the cells of an individual. The method comprises the step of contacting cells of said individual with a multifunctional molecular complex which includes said nucleic acid composition, as detailed further above, thereby administering to the cells, a nucleic acid molecule that comprises a nucleotide sequence that either encodes a desired peptide or protein, or serves as a template for functional nucleic acid molecules. The nucleic acid molecule is administered free from retroviral particles. The desired protein may either be a protein which functions within the individual or serves to initiate an immune response. The nucleic acid molecule may be administered to the cells of said individual on either an in vivo or ex vivo basis, i.e., the contact with the cells of the individual may take place within the body of the individual in accordance with the procedures which are most typically employed, or the contact with the cells of the individual may take place outside the body of the individual by withdrawing cells which it is desired to treat from the body of the individual by various suitable means, followed by contacting of said cells with said nucleic acid molecule, followed in turn by return of said cells to the body of said individual.

The present invention also concerns a method of immunizing an individual against a pathogen. The method comprises the step of contacting cells of said individual with a multifunctional molecular complex which includes a nucleic acid composition, as detailed further above, thereby administering to the cells, a nucleic acid molecule that comprises a nucleotide sequence that encodes a peptide which comprises at least an epitope identical to, or substantially similar to an epitope displayed on said pathogen as antigen, and said nucleotide sequence is operatively linked to regulatory sequences. The nucleic acid molecule is capable of being expressed in the cells of the individual.

The present invention relates to methods of immunizing an individual against a hyperproliferative disease or an autoimmune disease. The methods comprise the step of contacting cells of said individual with a multifunctional molecular complex which includes a nucleic acid composition, as detailed further above, thereby administering to cells of the individual, a nucleic acid molecule that comprises a nucleotide sequence that encodes a peptide that comprises at least an epitope identical to or substantially similar to an epitope displayed on a hyperproliferative disease-associated protein or an autoimmune disease-associated protein, respectively, and is operatively linked to regulatory sequences. The nucleic acid molecule being capable of being expressed in the cells.

The present invention also relates to methods of treating an individual suffering from an autoimmune disease comprising the steps of contacting cells of said individual with a multifunctional molecular complex which includes a nucleic acid composition, as detailed further above, thereby administering to cells of said individual, a nucleic acid molecule that comprises a nucleotide sequence which restores the activity of an absent, defective or inhibited gene, or which encodes a protein that produces a therapeutic effect in the individual, and is operatively linked to regulatory sequences; the nucleic acid molecule being capable of being expressed in said calls.

The present invention still further relates to pharmaceutical compositions which comprise a multifunctional molecular complex which includes a nucleic acid composition, as detailed further above, including pharmaceutically acceptable salt and ester forms of said molecular complex, together with a pharmaceutically acceptable carrier. In this regard, the present invention also relates to pharmaceutical kits which comprise a container comprising a nucleic acid composition, and a container comprising a transfer moiety. Optionally, there is included in such kits excipients, carriers, preservatives and vehicles such as solvents.

DETAILED DESCRIPTION OF THE INVENTION

In accordance with one embodiment of the present invention there is provided a multifunctional molecular complex for the transfer of a nucleic acid composition to a target cell, which provides for a high level of transfection and expression of the nucleic acid molecules in the target, i.e., host cell. This multifunctional molecular complex comprises essentially the combination of two key elements, (I) the nucleic acid composition which it is desired to transfer to the target cell, and (II) the transfer moiety, which complexes with the nucleic acid molecule, and comprises several components whose function is i) to locate the desired target cell within the body of an individual by means of a receptor specific binding component responsive to a specific receptor on the membrane surface of said target cell; ii) to overcome the incompatibility arising from the hydrophilic nature of the nucleic acid molecule and the lipophilic nature of the cell membrane so that the former can pass through the latter; and iii) to prevent degradation of the nucleic acid molecule in a lysosome of said target cell, by disrupting the pre-lysosome, endosome formation stage, which is accomplished by means of an endosome membrane disrupting component which permits the multifunctional molecular complex to escape from an endosome formed as a result of the target cell's process of endocytosis or pinocytosis, whereby the multifunctional molecular complex enters the target cell and is incorporated into said endosome.

The components of the transfer moiety are as follows: A) a cationic polyamine component bound to said nucleic acid composition, comprising from three to twelve nitrogen atoms; B) an endosome membrane disruption promoting component comprising at least one lipophilic long chain alkyl group attached to a nitrogen atom of said polyamine, or a shorter alkyl bridging group having a terminal carboxyl, amino, hydroxyl or sulfhydryl group to which there is attached a fusogenic peptide, or cholic acid or cholesteryl or derivative; and optionally C) one or more receptor specific binding components which are ligands for natural receptors of said target cell, attached to a shorter alkyl bridging group attached to a further nitrogen atom of said polyamine, through said terminal group thereof.

The transfer moiety may be represented as one or more independently selected cationic polyamine components of the formula (1):

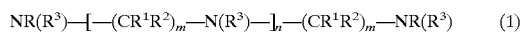

$$NR(R^3)-[-(CR^1R^2)_m-N(R^3)-]_n-(CR^1R^2)_m-NR(R^3) \quad (1)$$

wherein:

R, $R^1$ and $R^2$ are each independently selected from the group consisting of hydrogen and $C_{1-6}$ alkyl;

m in each occurrence is independently selected from the integers 2 through 5 inclusive; and is preferably 3 or 4;

n is selected from the integers 1 through 10 inclusive; and is preferably 1 to 6;

$R^3$ is independently selected from the group consisting of hydrogen; $C_{1-6}$ alkyl; and one or more endosome membrane disruption promoting components independently selected from the group consisting of:

a) —B—$(CR^1R^2)_j$—$C(R)_3$, where R, $R^1$ and $R^2$ are each independently defined as above; j is an integer from 6 to 24 inclusive, preferably 8 to 18, more preferably 8 to 12 inclusive; and B is optionally absent, or is a bridging group of the formula:
  i) —$(CR^1R^2)_k$—C(=O)—Z—;
  ii) —$(CR^1R^2)_k$—N(R)—C(=O)—Z—;
  iii) —$(CR^1R^2)_k$—N(R)—{—C(=O)—$CH_2$—O—[—$(CH_2)_2$—O—]$_l$—$(CH_2)_k$—N(R)}$_p$—C(=O)—Z—; or
  iv) —$(CR^1R^2)_k$—C(=O)—{—N(R)—[—$(CH_2)_2$—O—]$_l$—$CH_2$—C(=O)}$_p$—Z—;
  where k is, independently, an integer from 1 to 6 inclusive, preferably 3 to 5, 1 l is an integer from 0 to 30 inclusive, preferably 4 to 9, and p is an integer from 1 to 3 inclusive, preferably 1; R, $R^1$ and $R^2$ are each independently defined as above; and Z is O, S, N(R), or is absent, i.e., a single bond;

b) —B—$(R^4)$R, where R, $R^1$ and $R^2$ are each independently defined as above; B cannot be absent and is a bridging group independently selected from groups i) through iv) above, and additionally from the group of the formula:
  v) —$(CR^1R^2)_{j'}$—X—, where j' is an integer from 1 to 8 inclusive, preferably 2 to 6 inclusive, and more preferably 5;

R, $R^1$ and $R^2$ are each independently defined as above;

X is O, S, N(R), or absent; and $R^4$ is independently selected from the group consisting of:
  i) fusogenic peptides comprising spike glycoproteins of enveloped animal viruses;

ii) cholic acid derivatives of the formula (2):

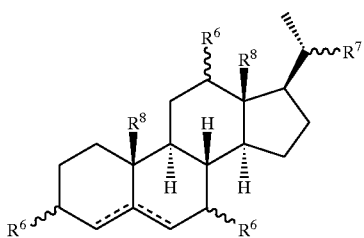

(2)

where:
⁓⁓⁓represents a bond of unspecified stereochemistry;
--- represents a single or double bond, i.e., a saturated or unsaturated portion of the ring system, provided that they cannot both be unsaturated at the same time, i.e., the ring system must be either Δ4 or Δ5;
$R^6$ is —H, —OH, —$CO_2$H, —C(=O)$NH_2$, —OC(=O)$NH_2$, —$NH_2$, or —O($CH_2CH_2O$)$_{n'}$H, where n' is an integer from 1 to 6 inclusive;
$R^7$ is a radical that forms the point of attachment of the cholic acid derivative, comprising —$C_{1-6}$alkyl- or —$C_{1-6}$alkylcarbonyl-; and
$R^8$ is $C_{1-6}$alkyl, especially $CH_3$; including the preferred cholic acid derivatives 3α, 7α, 12α-trihydroxy-5β-cholan-24-oic ester or amide; and iii) cholesteryl derivatives of the formula (3):

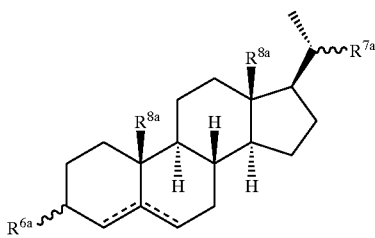

(3)

where:
⁓⁓⁓represents a bond of unspecified stereochemistry;
--- represents a single or double bond, i.e., a saturated or unsaturated portion of the ring system, provided that they cannot both be unsaturated at the same time, i.e., the ring system must be either Δ4 or Δ5;
$R^{6a}$ is a radical that forms the point of attachment of the cholesteryl derivative, comprising —$C_{1-6}$alkyl-, —OC(=O)—, or —$OCH_2$C(=O)—;
$R^{7a}$ is $C_{1-6}$alkyl, especially $(CH_2)_3CH(CH_3)_2$; and
$R^{8a}$ is $C_{1-6}$alkyl, especially $CH_3$; including the preferred cholesteryl derivatives cholest-5-en-3'-β-carbonate, -β-carbamate, or -β-methylenecarboxamide;

PROVIDED THAT $R^3$ is one or more endosome membrane disruption promoting components attached to at least one nitrogen atom of at least one of said cationic polyamine components; and OPTIONALLY, $R^3$ may be one or more groups defined below, attached either to a further nitrogen atom of at least one of said cationic polyamine components to which said one or more endosome membrane disruption promoting components is attached, or to a nitrogen atom of at least one further polyamine component which does not have attached thereto any endosome membrane disruption promoting component:

c) —B—($R^5$)R, where B cannot be absent, and is a bridging group independently selected from groups i) through v) inclusive; R is independently defined as above; and $R^5$ is a receptor specific binding component independently selected from the group consisting of:
   i) D-biotin;
   ii) β-3'-propionyl galactosyl-β1-4-thioglucoside;
   iii) $N^2,N^6$-bis(β3'-propionyl galactosyl-β1-4-thioglucoside)lysine;
   iv) $N^2,N^6$-bis(β-3'-propionyl galactosyl-β1-4-thioglucoside)lysyl-$N^6$-(β-3'-propionyl galactosyl-β1-4-thioglucoside)lysine;
   5-methyltetrahydrofolate;
   vi) folic acid;
   vii) folinic acid;
   viii) α-3'-propionyl thiomannoside; and
   ix) α-3'-propionyl thiomannoside-6-phosphate.

The Nucleic Acid Composition

The two basic components of the multifunctional molecular complex of the present invention are the nucleic acid composition and the transfer moiety. By "nucleic acid composition" is meant any one or more of the group of compounds in which one or more molecules of phosphoric acid are combined with carbohydrate, i.e., pentose or hexose, molecules, which are in turn combined with bases derived from purine, e.g., adenine, and from pyrimidine, e.g., thymine. Particular naturally occurring nucleic acid molecules include genomic deoxyribonucleic acid (DNA) and genomic ribonucleic acid (RNA), as well as the several different forms of the latter, e.g., messenger RNA (mRNA), transfer RNA (tRNA), and ribosomal RNA (rRNA). Also included are the different DNA's which are complementary (cDNA) to the different RNA's. Synthesized DNA or a hybrid thereof with naturally occurring DNA, is contemplated.

The nucleic acid compositions used in the present invention may be either single-stranded or double-stranded, may be linear or circular, e.g., a plasmid, and are either oligo- or polynucleotides. They may comprise as few as 15 bases or base pairs, or may include as many as 20 thousand bases or base pairs (20 kb). Since the transfer moiety is employed on a pro rata basis when added to the nucleic acid composition, practical considerations of physical transport will largely govern the upper limit on the size of nucleic acid compositions which can be utilized.

In addition to these naturally occurring materials, the nucleic acid compositions used in the present invention can also include synthetic compositions, i.e., nucleic acid analogs. These have been found to be particularly useful in antisense methodology, which is the complementary hybridization of relatively short oligonucleotides to single-stranded RNA or single-stranded DNA, such that the normal, essential functions of these intracellular nucleic acids are disrupted. See, e.g., Cohen, *Oligonucleotides: Antisense Inhibitors of Gene Expression*, CRC Press, Inc., Boca Raton, Fla. (1989).

The size, nature and specific sequence of the nucleic acid composition to be transferred to the target cell can be optimized for the particular application for which it is intended, and such optimization is well within the skill of the artisan in this field. However, the nature of the target cells within the individual into which it is desired to transfer a nucleic acid composition, may have a significant bearing on the choice of the particular multifunctional molecular complex of the present invention. For example, where it is desired to transfer nucleic acid molecules to target cells by injecting them intramuscularly to evoke an immune response, it will be found that this transfer can be effected by use of a multifunctional molecular complex of the present invention, as defined above, comprising a cationic polyamine to which is attached, as the endosome membrane disruption promoting component, a lipophilic long chain alkyl group as defined above. Where the target cells are hepatocytes, for example, transfer of the desired nucleic acid composition is readily effected by use of the multifunctional molecular complex of the present invention wherein there is attached to the cationic polyamine a receptor specific binding component which will permit discrimination among body cells, comprising, e.g., $N^2,N^6$-bis($\beta$-3'-propionyl galactosyl-$\beta$1-4-thioglucoside)lysine, or $N^2,N^6$-bis($\beta$-3'-propionyl galactosyl-$\beta$1-4-thioglucoside)lysyl-$N^6$-($\beta$-3'propionyl galactosyl-$\beta$1-4-thioglucoside)lysine.

The nucleic acid composition to be transferred to a target cell in accordance with the present invention must have an appropriate open reading frame and promoter to express a protein, as well as any other regulatory sequences which may be appropriate to expression. Nucleic acid compositions to be delivered by means of the methods of the present invention can be designed and constructed so as to be appropriate for the particular application desired, all of which is well within the ordinary skill of the artisan in this field.

The nucleic acid molecules which are delivered to cells using the multifunctional molecular complex and methods of the present invention may serve as: 1) genetic templates for proteins that function as prophylactic and/or therapeutic immunizing agents; 2) replacement copies of defective, missing or non-functioning genes; 3) genetic templates for therapeutic proteins; 4) genetic templates for antisense molecules and as antisense molecules per se; or 5) genetic templates for ribozymes.

In the case of nucleic acid molecules which encode proteins, the nucleic acid molecules preferably comprise the necessary regulatory sequences for transcription and translation in the target cells of the individual animal to which they are delivered.

In the case of nucleic acid molecules which serve as templates for antisense molecules and ribozymes, such nucleic acid molecules are preferably linked to regulatory elements necessary for production of sufficient copies of the antisense and ribozyme molecules encoded thereby respectively. The nucleic acid molecules are free from retroviral particles and are preferably provided as DNA in the form of plasmids.

The Transfer Moiety

The core, or backbone of the transfer moiety is the cationic polyamine, containing between 3 and 12 amines. There may be more than one of these cationic polyamine components, whose function is to overcome the incompatibility arising from the hydrophilic nature of the nucleic acid molecule and the lipophilic nature of the cell membrane, although this by itself will not permit the former to pass through the latter. The cationic groups of the polyamine bind to the anionic groups of the nucleic acid through ionic bonding, thus neutralizing those charges and also serving as a point of attachment for the complex. One µg of DNA contains 3.1 nanomoles of phosphate anionic charges, assuming a mean molecular weight of 325 for a nucleotide sodium salt. The transfer moiety of the present invention will not become effective in achieving transfer of the nucleic acid composition until the anionic charges of said nucleic acid are substantially neutralized by the cationic charges of the polyamine component of the transfer moiety.

It will be appreciated that in one embodiment of the present invention, a single cationic polyamine can be employed which, conceptually, balances the anionic charges of the nucleic acid in a more or less stoichiometric fashion, although it will be understood that, as a practical matter, it will be necessary to employ amounts of cationic polyamine which are significantly in excess of the stoichimetric amount, because of the presence of competing binding sites in target and other cells, whose existence is well known to the artisan and which competitively prevent or otherwise interfere with the binding of the polyamine to the nucleic acid as desired. It is also contemplated that more than one such cationic polyamine can be employed, in which case each polyamine chain or piece is smaller than the corresponding nucleic acid to which it will become bound. It will be understood, however, that the total size or length of these individual cationic polyamine components should together be substantially the same size or length as the nucleic acid component, in order for neutralization of the anionic charges of the nucleic acid to take place. Again, it will be understood that for practical reasons, a significant excess of cationic polyamine components, over the amount of nucleic acid component present, will be necessary. Using more than one cationic polyamine component permits flexibility with respect to the types of groups that are attached thereto. For example, one cationic polyamine component may carry a particular endosome membrane disruption promoting component, while another cationic polyamine component carries a receptor specific binding component, or perhaps a different endosome membrane disruption promoting component. The total number of such cationic polyamine components is variable, and will depend not only on the size or length of the nucleic acid component, but on the number and type of groups attached thereto as well.

Transfer efficiency, i.e., transfection, does not become optimum until the multifunctional molecular complex, the combination of the transfer moiety and the nucleic acid, bears a strong positive charge. Thus, the amount of transfer moiety must be selected with this in mind, and the actual amount chosen be depend on the charge density thereof, which can be calculated by means well known in the art.

The triamine, tetraamine, pentaamine and higher polyamine components of the transfer moiety must be cationic in order to be functional, as explained above. This can be accomplished by the simple expedient of making an acid addition salt, e.g., the hydrochloride salt, where ammonium chloride units are formed. It may also be the case that the cationic form of the polyamine is formed under conditions of physiologic pH, in which case it is not necessary to form the cation directly. Thus, the term "cationic polyamine" is intended to include both of these possibilities.

It is contemplated that the number of amine groups that it is desired to have present in the polyamine will depend to some extent on the mode of administration of the multifunctional molecular complex that is used. For example, it is contemplated that for intramuscular administration, it is preferred to have from 3 to 5 amine groups in the polyamine; whereas, for systemic injection, e.g., intravenous injection, it is preferred to have from 5 to 8 amine groups in the polyamine. For in vitro applications generally, it is preferred to have from 5 to 8 amine groups in the polyamine.

The next component of the transfer moiety is the endosome membrane disruption promoting component, which is required to be present. This can either comprise one or more lipophilic long chain alkyl groups attached through one or more of the nitrogen atoms of said polyamine, or can comprise a bridging group "B", e.g., a shorter alkyl linking moiety, optionally with a terminal amino, hydroxyl or sulfhydryl group, through which there is attached a fusogenic peptide, or cholic acid or cholesteryl or derivative compound.

The lipophilic long chain alkyl group is defined by the formula: —B—$(CR^1R^2)_j$—$C(R)_3$, where B is a bridging group as defined; R, $R^1$ and $R^2$ are each independently selected from the group consisting of hydrogen and $C_{1-6}$ alkyl; and j is an integer from 6 to 24 inclusive, preferably 8 to 18, more preferably 8 to 12 inclusive.

The group "—B—" may be absent, i.e., a single bond, where $R^3$ is the endosome membrane disruption promoting component comprising a lipophilic long chain alkyl group as defined under "a)" above. The group "—B—" may also be a bridging element which is a member independently selected from the group consisting of:

i) —$(CR^1R^2)_k$—C(=O)—N(R)—;

ii) —$(CR^1R^2)_k$—N(R)—C(=O)—O—;

iii) —$(CR^1R^2)_k$—N(R)—{—C(=O)—$CH_2$—O—[—$(CH_2)_2$—O—]$_l$—$(CH_2)_k$—N(R)}$_p$—C(=O)—z—;

iv) —$(CR^1R^2)_k$—C(=O)—{—N(R)—[—$(CH_2)_2$—O—]$_l$—$CH_2$—C(=O)}$_p$—N(R)—z—; or v) —$(CR^1R^2)_j$—X—, where the various substituents are as defined above.

Where the endosome membrane disruption promoting component, rather than being a lipophilic long chain alkyl group, is instead a fusogenic peptide or a cholic acid or cholesteryl or derivative compound, the bridging group "B" is required to be present, and will be a member independently selected from the group i) through v) above. This selection will be dependent upon the required or desired type of chemical linkage to be present. For example, members i) and iv) are carboxamide linkages, whereas members ii) and iii) are carbamate, thiocarbamate, or carbamoyl linkages, depending upon whether "Z" is O, S or absent, respectively. For member v), the linkages will be oxy, thio, amino, or alkylene, depending upon whether "X" is O, S, N(R), or absent, respectively. The endosome membrane disruption promoting component, on the other hand, may have a carbonyl, amino, or some other terminal group, which can determine the choice of bridging member to be used. All such choices, however, are well within the skill of the artisan in this field.

Most simply, the bridging group can be an alkylene linking moiety used primarily for steric considerations. However, the other bridging groups may also be desirable for imparting various physical and chemical, as well as configurational properties to the multifunctional molecular complex of the present invention. The polyethylene glycol group can be especially useful in this regard.

The term "$C_{1-6}$ alkyl", as used above, and throughout the description of the present invention, refers to straight and branched chain alkyl groups including, but not limited to methyl, ethyl, propyl, isopropyl, n-butyl, iso-butyl, sec-butyl, t-butyl, and n-pentyl.

In the formula for the lipophilic long chain alkyl group above, it is preferred that R, $R^1$ and $R^2$ are all hydrogen, and, as indicated that j be an integer from 8 to 18 inclusive. There must be at least one of these lipophilic long chain alkyl groups present, but preferably there are no more than three such groups present. It is preferred to have only one such group. Thus, examples of preferred transfer moieties of the present invention, where the endosome membrane disruption promoting component is a lipophilic long chain alkyl group as described above, are $N^4$-octylspermidine, $N^4$-dodecylspermidine, $N^4$-octadecylspermidine, $N^4$-octylspermine, $N^4$-dodecylspermine, and $N^4$-octadecylspermine.

The endosome membrane disruption promoting component can also comprise a shorter alkyl bridging group, optionally having a terminal amino, hydroxyl or sulfhydryl group through which there is attached a fusogenic peptide, or cholesterol or derivative compound. Such a component may be represented by the formula —B—$(R^4)$R, where the B group is —$(CR^1R^2)_{j'-x-}$, where R, $R^1$ and $R^2$ are each independently selected from the group consisting of hydrogen and $C_{1-6}$ alkyl; j' is an integer from 1 to 6 inclusive, preferably 2 to 4 inclusive; X is O, S, N(R), or absent.

It is, preferred that R, $R^1$ and $R^2$ each be hydrogen, and as indicated, that j' be 2 to 4, while X is defined as N. Thus, the shorter alkyl bridging group will preferably be ethyl, n-propyl, or n-butyl, and will have a terminal amino group to which is attached the fusogenic peptide, or cholic acid or cholesteryl or derivative compound, which comprises the endosome membrane disruption promoting component.

Alternatively, other of the members of the "B" bridging group can be chosen. For example, member i) provides an alkyl bridging moiety with a carboxamide linkage, the most simple representative of which would be the group —$(CH_2)$—C(=O)—NH—. Member ii) provides an alkylene bridging moiety with a carbamate type of linkage; and the most simple representative of this member would be the group —$(CH_2)$—NH—C(=O)—, which is a carbamoyl type of linkage. A carbamate linkage would be represented by the group —$(CH_2)$—NH—C(=O)—O—, while a simple variant of this group would provide a thiocarbamate linkage: —$(CH_2)$—NH—C(=O)—S—. Members iii) and iv) provide the same terminal linkage variants, while adding to the alkyl bridging moiety a polyethylene glycol bridging moiety of variable size, i.e., number of repeating ethylene oxide monomer units, depending upon the definitions of "l" and "p".

The fusogenic peptide which functions as an endosome membrane disruption promoting component, comprises the spike glycoproteins of enveloped animal viruses known in the art. Membrane fusion, whether planar or annular, comprises the stages of initial approach, coalescence, and separation. Fusion reactions are rapid, highly specific, and non-leaky. The membrane proteins of enveloped animal viruses comprise glycoproteins which span the bilayer of the virus membrane and have the bulk of their mass externally, and non-spanning, nonglycosylated proteins associated with the inner bilayer surface. The glycoproteins form radial projections on the surface of the virus membrane, and these spike glycoproteins play a key role in virus entry into host cells. Spike glycoproteins are among the best-characterized virus membrane proteins. In cell entry the spike glycoproteins are responsible for attachment of the virus particle to the cell surface, and for penetration of the nucleocapsid into the cytosol, where, after endocytosis of the virus particle, the spike glycoproteins play a role in fusion with the limiting membrane of the endosome, whereby the nucleocapsid reenters the cytosol. In some enveloped animal viruses, the spike glycoproteins take on a specialized character, e.g., in orthomyxoviruses, where one is a neuraminidase and another is a haemagglutinin. All of these fusogenic peptides, in terms of their amino acid sequences, gross morphology, role in the overall process of fusion, and requirements for activity, have been the subject of long term study and have been disclosed in detail in the technical literature. See, e.g., J. White, M. Kielian and A. Helenius, *Quarterly Reviews of Biophysics,* 16, 151–195 (1983), which is incorporated herein by reference in its entirety.

Examples of such fusogenic peptides and homologues derived from spike glycoproteins of enveloped viruses, include the following peptide sequences reading from N-terminus to C-terminus:

SEQ ID NO:1: KFTIVFPHNQKGNWKNVPSNYHYCP (R. Schlegel and M. Wade, J. Biol. Chem., 259, 4691–94 (1984))-VSV; poly(Glu-Aib-Leu-Aib) (K. Kono, H. Nishii and T.

Takagishi, Biochim. Biophys. Acta, 1164, 81–90 (1993));

SEQ ID NO:2: AVGIGALFLGFLGAAGSTM-GAASMTLTVQARQ HIV—1;

SEQ ID NO:3: EPVSLTLALLLGGLTMGGIAAGVGTGTTALVATQQ—MuLV (J. S. Jones and R. Risser, J. Virol., 67, 67–74 (1993));

SEQ ID NO:4: AVGIGALFLGFLGAAGSTMGARS—HIV-1 (J. L. Nieva, S. Nir, A. Muga, F. M. Goni and J. Wilschut, Biochem., 33, 3201–09 (1994)); SEQ ID NO:5: AVGAIGALFLGFLGAAG—HIV-1 (S. Soukchareun, G. W . Tregear and J. Haralambidis, Bioconj. Chem., 6, 43–53 (1995));

SEQ ID NO:6: GLFEAIAEFIEGGWEGLIEGCA—HA-2 (P. Midoux, C. Mendes, A. Legrand, J. Raimond, R. Mayer, M. Monsigny and A. C. Roche, Nucl. Acids Res., 21, 871–78 (1993));

SEQ ID NO:7: GLFGAIAGFIENGWEGMIDGWYGFR—HA-2;

SEQ ID NO:8: AVGIGALFLGFLGAAGSTMGAAS—HIV-1 gp41;

SEQ ID NO:9: FAGWIGLAALGVATAANVTA AVALVK—SVS F1;

SEQ ID NO:10: KVYTGVYPFMWGGAYCFCD—SFV E1;

SEQ ID NO:11: KLICTGISSIPPIRALFAAINIP—PH-30 α (J. M. White, Science, 258, 917–24 (1992));

SEQ ID NO:12: FFGAVIGTIALGVATATAAQIT—Sendai F1;

SEQ ID NO:13: FAGVVIGLAALGVATATAAQVT—SV5 F1;

SEQ ID NO:14: FIGAIIGGVALGVATATAAQIT—NDV F1;

SEQ ID NO:15: GLFGAIAGFIENGWEGMID GWYGFRHQN—HA-2 X:31;

SEQ ID NO:16: GLFGAIAGFIENGWEGLVD GWYGFRHQN—HA-2 FPV;

SEQ ID NO:17: GFFGAIAGFLEGGWEGMIA GWHGYTSHG—HA-2 B/Lee;

SEQ ID NO:18: FVAAIILGISALIAIITSFA VATTALVKEM—MMTV gp36;

SEQ ID NO:19: EPVSLTLALLLGGLTMGGIAA GIGTGTTALMATQQFQQLQAAVQDDLREVEKS—MOMLV p15E;

SEQ ID NO:20: EPVSLTLALLLGGLTMGGIAA GVGTGTTALVATQQFQQLHAAVQDDLKEVEKS—F-MULV p15E;

SEQ ID NO:21: EPVSLTLALLLGGLTMGGIAA GVGTGTTALVATQQFQQLQAAMHDDLKEVEKS—AKV p15E;

SEQ ID NO:22: DYQCKVYTGVYPFMWGGA YCFCDSENT—SFV E1;

SEQ ID NO:23: DYTCKVFGGVYPFMWGGA QCFCDSENS—Sindbis E1 (J. White, M Kielian and A. Helenius, Q. Rev. Biophys., 16, 151–95 (1983));

SEQ ID NO:24: FAGVVLAGAALGVAAAAQI—measles;

SEQ ID NO:25: FAGVVLAGAALGVATAAQI—measles (P. L. Yeagle, R. M. Epand, C. D. Richardson and T. D. Flanagan, Biochim. Biophys. Acta, 1065, 49–53 (1991));

SEQ ID NO:26: GLFGAIAGFIENGWEGMIDGGGC—HA-2 (E. Wagner, C. Plank, K. Zatloukal, M. Cotten and M. L. Birnstiel, Proc. Nat. Acad. Sci. USA, 89, 7934–38 (1992));

SEQ ID NO:27: GLFGAIAGFIENGWEGMIDG—X31F/68 HA-2;

SEQ ID NO:28: GIFGAIAGFIENGWEGMIDG—VIC/75 HA-2;

SEQ ID NO:29: GLFGAIAGFIEGGWTGMIDG—PR/8/34 HA-2;

SEQ ID NO:30: GLFGAIAGFIEGGWEGMVDG—Jap/57 HA-2;

SEQ ID NO:31: GLFGAIAGFIEGGWEGLVDG—PPV/34 HA-2; and

SEQ ID NO:32: GFFGAIAGFLEGGWEGMIAG—X31F/68 HA-2 (J. D. Lear and W. F. DeGrado, J. Biol. Chem., 262, 6500–05 (1987)).

One of ordinary skill in the art would readily recognize that other such fusogenic peptides could be used in the invention including peptides functionally equivalent to those described but having one or more amino acid additions, deletions, or substitutions, especially those having conserved amino acid substitutions.

The cholic acid and derivatives which function as endosome membrane disruption promoting components, comprise compounds of the formula (2):

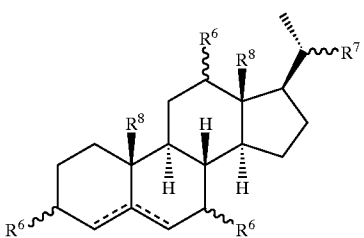

(2)

where:

∿∿∿represents a bond of unspecified stereochemistry;

represents a single or double bond, i.e., a saturated or unsaturated portion of the ring system, provided that they cannot both be unsaturated at the same time, i.e., the ring system must be either Δ4 or Δ5;

$R^6$ is H, OH, $CO_2H$, —C(=O)$NH_2$, —OC(=O)$NH_2$, —$NH_2$, or —O($CH_2CH_{2O}$)$_{n'}$H, where n' is an integer from 1 to 6 inclusive;

$R^7$ is a radical that forms the point of attachment of the cholic acid derivative, comprising —$C_{1-6}$alkyl- or —$C_{1-6}$alkylcarbonyl-; and $R^8$ is $C_{1-6}$alkyl, especially $CH_3$. It is preferred that the cholic acid and derivative compounds comprise one or more members selected from the group consisting of 3α, 7α, 12α-trihydroxy-5β-cholan-24-oic ester and amide.

The cholesteryl and derivatives which function as endosome membrane disruption promoting components, comprise compounds of the formula (3):

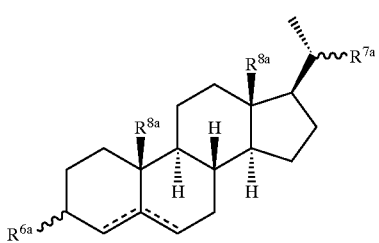

(3)

where:
  ⁓ represents a bond of unspecified stereochemistry;
  represents a single or double bond, i.e., a saturated or unsaturated portion of the ring system, provided that they cannot both be unsaturated at the same time, i.e., the ring system must be either Δ4 or Δ5;
  $R^{6a}$ is a radical that forms the point of attachment of the cholic acid derivative, comprising —$C_{1-6}$alkyl-, —OC(=O)—, or —$OCH_2C$(=O)—;
  $R^{7a}$ is $C_{1-6}$alkyl, especially $(CH_2)_3CH(CH_3)2$; and
  $R^{8a}$ is $C_{1-6}$alkyl, especially $CH_3$. It is preferred that the cholesteryl and derivative compounds comprise one or more members selected from the group consisting of cholest-5-en-3'-β-carbonate, -β-carbamate, and -β-methylene-carboxamide.

An optional embodiment of the present invention is to provide for a receptor specific binding component which helps effect transfer of nucleic acid compositions to target cells, especially eukaryotic cells, by taking advantage of the natural receptor-mediated endocytosis pathways which exist in those cells. The receptor specific binding component is thus a ligand for the natural receptor, and can thus assist in binding of the multifunctional molecular complex to the target cell. Endocytosis or pinocytosis will then take place whereby the entire complex is transferred into the target cell, enclosed in an endosome.

The receptor specific binding component serves the important function of allowing the multifunctional molecular complex of the present invention to be targeted to specific cell populations, e.g., hepatocytes. The binding component facilitates location of the desired target cells within the body of the animal to which the complex is being administered, with subsequent attachment of the complex to the target cells.

Where the receptor specific binding component is employed, there will also be present on the multifunctional molecular complex an endosome membrane disruption promoting component, as defined further above. Accordingly, once the binding component has located the desired target cell within the individual, and attached the complex to said cell by binding to said receptor, the complex will be transferred into said cell by endocytosis, whereupon it will be enclosed within an endosome. At this point, the endosome membrane disruption promoting component assumes its important role by disrupting said membrane, allowing escape of the complex into the cytoplasm of said cell.

During the normal course of events in the target cell, endosome formation is a prelude to targeting of any foreign protein to lysosomes where degradation of the foreign protein by hydrolytic enzymes will take place. Consequently, accumulation in lysosomal compartments can be a major obstacle to the effectiveness of nucleic acid delivery systems. The multifunctional molecular complex of the present invention would suffer the same fate, were it not for the presence of the endosome membrane disruption promoting component. This component permits the complex to escape from the endosome, whereupon it can migrate into the nucleus of the target cell, and release the nucleic acid composition, whose genetic information can then be transcribed within said nucleus. Although the precise mechanisms which make up these steps and pathways are not well understood, expression of the nucleic acid molecule contained in the multifunctional molecular complex does take place, as is demonstrated in the working examples further below.

The receptor specific binding component may be so represented by the formula: —B—$(R^5)$R, where R, $R^1$ and $R^2$ are each independently hydrogen or $C_{1-6}$ alkyl; B may be, inter alia, —$(CR^1R^2)_{j'}$—X—, where $R^1$ and $R^2$ are as defined above, X is N(R), and j' is an integer from 1 to 6 inclusive, preferably 2 to 4 inclusive; and $R^5$ is a receptor specific binding component independently selected from the group consisting of:
  i) D-biotin;
  ii) β-3'-propionyl galactosyl-β1-4-thioglucoside;
  iii) $N^2,N^6$-bis(β-3'-propionyl galactosyl-β1-4-thioglucoside)lysine;
  iv) $N^2,N^6$-bis(β-3'-propionyl galactosyl-β1-4-thioglucoside)lysyl-$N^6$-(β-3'-propionyl galactosyl-β1-4-thioglucoside)lysine;
  v) 5-methyltetrahydrofolate;
  vi) folic acid;
  vii) folinic acid;
  viii) α-3'-propionyl thiomannoside; and
  ix) α-3'-propionyl thiomannoside-6-phosphate.

It is preferred that R, $R^1$ and $R^2$ each be hydrogen, and as indicated, that j' be 2 to 6. Thus, the shorter alkyl bridging group will preferably be ethyl, n-propyl, or n-butyl, and the receptor specific binding component is attached to the terminal amino group.

Since the endosome membrane disruption promoting component must also be present, examples of preferred transfer moieties of the present invention, where the receptor specific binding component is a galactosyl group as described above, are
$N^2$-octyl-$N^4$-(5-(β-3'-propionyl galactosyl-β1"-4'-thioglucoside)amino)pentylspermidine;
$N^2$-dodecyl-$N^4$-(5-(β-3'-propionyl galactosyl-β1"-4'-thioglucoside)amino)pentylspermidine;
$N^6$-octadecyl-$N^4$-(5-(β-3'-propionyl galactosyl-β1"-4'-thioglucoside)amino)pentyl-spermidine;
$N^6$-octyl-$N^4$-(5-[$N^{2'},N^{6'}$-bis(β1-3'-propionyl galactosyl-β1-4-thioglucoside)lysyl-$N^{6'}$-(β-3'-propionyl galactosyl-β1-4-thioglucoside)lysyl]amino)pentyl-spermine;
$N^2$-dodecyl-$N^4$-(5-[$N^{2'},N^{6'}$-bis(β1-3'-propionyl galactosyl-β1-4-thioglucoside)lysyl-$N^{6'}$-(β3'-propionyl galactosyl-β1-4-thioglucoside)lysyl]amino)pentyl-spermine; and
$N^2$-octadecyl-$N^4$-(5-[$N^{2'},N^{6'}$-bis(β1-3'-propionyl galactosyl-β1-4-thioglucoside)lysyl-$N^{6'}$-(β-3'-propionyl galactosyl-β1-4-thioglucoside)lysyl]amino)pentyl-spermine.

Accordingly, there has been described in detail above the multifunctional molecular complex of the present invention for transfer of nucleic acid compositions to a target cell. This complex includes the transfer moiety as a separate, distinct embodiment of the present invention. Further aspects of the present invention relate to the methods of using the multifunctional molecular complex.

Thus, in accordance with the present invention there is provided a method for the transfer of a nucleic acid composition to target cells on an in vitro basis. In this method target cells are contacted with a multifunctional molecular complex which includes said nucleic acid composition. In one embodiment, the target cells have been isolated from an individual, and all of the cells are thus of the same type, and it is not necessary, therefore, for the complex to include a receptor specific binding component. An especially preferred embodiment is one in which a microorganism culture is maintained under fermentation conditions, and a protein product is expressed by the microorganism as a result of the transfer thereto of nucleic acid compositions using the multifunctional molecular complex of the present invention. The protein product is isolated and purified. Here again, a single type of target cell is involved, so that it is not necessary that a receptor specific binding component be present.

This method provides for transfer to target cells of a nucleic acid molecule that comprises a nucleotide sequence that either encodes a desired peptide or protein, or serves as a template for functional nucleic acid molecules. The desired protein or functional nucleic acid molecule may be any product of industrial, commercial or scientific interest, e.g., therapeutic agents including vaccines; foodstuffs and nutritional supplements; compounds of agricultural significance such as herbicides and.plant growth regulants, insecticides, miticides, rodenticides, and fungicides; compounds useful in animal health such as parasiticides including nematocides; and so forth. The target cells are typically cultures of host cells comprising microorganism cells such as bacteria and yeast, but may also include plant and mammalian cells. The cell cultures are maintained in accordance with fermentation techniques well known in the art, which maximize production of the desired protein or functional nucleic acid molecule, and the fermentation products are harvested and purified by known methods.

The present invention further relates to a method for the transfer of a nucleic acid composition to the cells of an individual in an in vivo manner. The method comprises the step of contacting cells of said individual with a multifunctional molecular complex of the present invention, which includes said nucleic acid composition. Here again, the nucleic. acid molecule comprises a nucleotide sequence that either encodes a desired peptide or protein, or serves as a template for functional nucleic acid molecules. The nucleic acid molecule is administered free from retroviral particles. The desired protein may either be a protein which functions within the individual or serves to initiate an immune response.

The nucleic acid molecule may be administered to the cells of said individual on either an in vivo or ex vivo basis, i.e., the contact with the cells of the individual may take place within the body of the individual in accordance with the procedures which are most typically employed, or the contact with the cells of the individual may take place outside the body of the individual by withdrawing cells which it is desired to treat from the body of the individual by various suitable means, followed by contacting of said cells with said nucleic acid molecule, followed in turn by return of said cells to the body of said individual.

The method of transferring a nucleic acid composition to the cells of an individual provided by the present invention, includes particularly a method of immunizing an individual against a pathogen. In this method, the nucleic acid composition administered to said cells, comprises a nucleotide sequence that encodes a peptide which comprises at least an epitope identical to, or substantially similar to an epitope displayed on said pathogen as antigen, and said nucleotide sequence is operatively linked to regulatory sequences. The nucleic acid molecule must, of course, be capable of being expressed in the cells of the individual.

The method of transferring a nucleic acid composition to the cells of an individual provided by the present invention, further includes methods of immunizing an individual against a hyperproliferative disease or an autoimmune disease. In such methods, the nucleic acid composition which is administered to the cells of the individual comprises a nucleotide sequence that encodes a peptide that comprises at least an epitope identical to or substantially similar to an epitope displayed on a hyperproliferative diseaseassociated protein or an autoimmune disease-associated protein, respectively, and is operatively linked to regulatory sequences. Here again, the nucleic acid molecule must be capable of being expressed in the cells of the individual.

In accordance with the present invention there is also provided methods of treating an individual suffering from an autoimmune disease, in which the cells of said individual are contacted with a multifunctional molecular complex including a nucleic acid composition, thereby administering a nucleic acid molecule that comprises a nucleotide sequence which restores the activity of an absent, defective or inhibited gene, or which encodes a protein that produces a therapeutic effect in said individual, and is operatively linked to regulatory sequences; the nucleic acid molecule being capable of being expressed in said cells.

In order to carry out the methods described above, the present invention provides pharmaceutical compositions which comprise the multifunctional molecular complex including a nucleic acid composition, as well as pharmaceutically acceptable salt and ester forms of said molecular complex, together with a pharmaceutically acceptable carrier. Also included are kits which comprise a container comprising a nucleic acid composition, and a container comprising a transfer moiety, as described herein. Optionally, there is included in such kits excipients, carriers, preservatives and vehicles such as solvents.

Accordingly the present invention provides compositions and methods which prophylactically and/or therapeutically immunize an individual against a pathogen or abnormal, disease-related cell. The genetic material encodes a peptide or protein that shares at least an epitope with an immunogenic protein found on the pathogen or cells to be targeted. The genetic material is expressed by the individual's cells and serves as an immunogenic target against which an immune response is elicited. The resulting immune response is broad based: in addition to a humoral immune response, both arms of the cellular immune response are elicited. The methods of the present invention are useful for conferring prophylactic and therapeutic immunity. Thus, a method of immunizing includes both methods of protecting an individual from pathogen challenge, or occurrence or proliferation of specific cells, as well as methods of treating an individual suffering from pathogen infection, hyperproliferative disease or autoimmune disease. Thus, the present invention is useful to elicit broad immune responses against a target protein, i.e. proteins specifically associated with pathogens or the individual's own "abnormal" cells.

The present invention is also useful in combating hyperproliferative diseases and disorders such as cancer, by eliciting an immune response against a target protein that is specifically associated with the hyperprolifertive cells. The present invention is further useful in combating autoimmune diseases and disorders by eliciting an immune response against a target protein that is specifically associated with cells involved in the autoimmune condition.

Other aspects of the present invention relate to gene therapy. This involves compositions and methods for introducing nucleic acid molecules into the cells of an individual which are exogenous copies of genes which either correspond to defective, missing, non-functioning or partially functioning genes in the individual, or which encode therapeutic proteins, i.e., proteins whose presence in the individual will eliminate a deficiency in the individual and/or whose presence will provide a therapeutic effect on the individual. There is thus provided a means of delivering such a protein which is a suitable, and even preferred alternative to direct administration of the protein to the individual.

As used herein the term "desired protein" is intended to refer to peptides and proteins encoded by gene constructs used in the present invention, which either act as target proteins for an immune response, or as a therapeutic or compensating protein in gene therapy regimens.

Using the methods and compositions of the present invention, DNA or RNA that encodes a desired protein is introduced into the cells of an individual where it is expressed, thus producing the desired protein. The nucleic acid composition, e.g., DNA or RNA encoding the desired protein is linked to regulatory elements necessary for expression in the cells of the individual. Regulatory elements for DNA expression include a promoter and a polyadenylation signal. In addition, other elements, such as a Kozak region, may also be included in the nucleic acid composition.

As used herein, the term "nucleic acid composition" refers to the DNA or RNA, or other nucleic acid molecule that comprises a nucleotide sequence which encodes the desired protein, and which includes initiation and termination signals operably linked to regulatory elements including a promoter and polyadenylation signal capable of directing expression in the cells of the individual to which the construct is administered.

As used herein, the term "expressible form" refers to gene constructs which contain the necessary regulatory elements operably linked to a coding sequence that encodes a target protein, such that when present in the cell of the individual, the coding sequence will be expressed.

As used herein, the term "genetic vaccine" refers to a pharmaceutical preparation that comprises a nucleic acid composition that comprises a nucleotide sequence that encodes a target protein, including pharmaceutical preparations useful to invoke a therapeutic immune response.

As used herein, the term "genetic therapeutic" refers to a pharmaceutical preparation that comprises a nucleic acid composition that comprises a nucleotide sequence that encodes a therapeutic or compensating protein. Alternatively, a genetic therapeutic may encode antisense sequences which inhibit undesired gene expression. Further, genetic therapeutics may encode ribozymes.

As used herein, the term "target protein" refers to a protein against which an immune response can be elicited. The target protein is an immunogenic protein which shares at least an epitope with a protein from the pathogen or undesirable cell-type, such as a cancer cell or a cell involved in autoimmune disease, against which immunization is required. The immune response directed against the target protein will protect the individual against, and treat the individual for, the specific infection or disease with which the target protein is associated.

As used herein, the term "sharing an epitope" refers to proteins which comprise at least one epitope that is identical to or substantially similar to an epitope of another protein.

And, the term "substantially similar epitope" is meant to refer to an epitope that has a structure which is not identical to an epitope of a protein, but nonetheless invokes a cellular or humoral immune response which cross reacts to that protein.

As used herein, the term "therapeutic protein" is meant to refer to proteins whose presence confers a therapeutic benefit to the individual.

As used herein, the term "compensating protein" is meant to refer to proteins whose presence compensates for the absence of a fully functioning endogenously produced protein, due to an absent, defective, non-functioning or partially functioning endogenous gene.

When taken up by a target cell, a nucleic acid composition used in the present invention, which includes the nucleotide sequence encoding the desired protein operably linked to regulatory elements, may remain present in the cell as a functioning extrachromosomal molecule, or it may integrate into the cell's chromosomal DNA. DNA may be introduced into cells where it remains as separate genetic material in the form of a plasmid. Alternatively, linear DNA which can integrate into the chromosome may be introduced into the target cell. When introducing DNA into the cell, reagents which promote DNA integration into chromosomes may be added. DNA sequences which are useful to promote integration may also be included in the DNA molecule. Alternatively, RNA may be administered to the cell. It is also contemplated to provide the nucleic acid composition as a linear minichromosome including a centromere, telomeres and an origin of replication. As used herein, the terms "DNA construct", "nucleic acid composition" and "nucleotide sequence" are meant to refer to both DNA and RNA molecules.

The regulatory elements necessary for gene expression of a DNA molecule include: a promoter, an initiation codon, a stop codon, and a polyadenylation signal. In addition, enhancers are often required for gene expression. It is necessary that these elements be operably linked to the sequence that encodes the desired proteins and that the regulatory elements are operable in the individual to whom they are administered.

Initiation codons and stop codon are generally considered to be part of a nucleotide sequence that encodes the desired protein. However, it is necessary that these elements be functional in the individual to whom the gene construct is administered. The initiation and termination codons must be in frame with the coding sequence. Promoters and polyadenylation signals used must also be functional within the cells of the individual.

Examples of promoters useful with the nucleic acid compositions used in the present invention, especially in the production of a genetic vaccine for humans, include but are not limited to, promoters from Simian Virus 40 (SV40), Mouse Mammary Tumor Virus (MMTV) promoter, Human Immunodeficiency Virus (HIV) such as the HIV Long Terminal Repeat (LTR) promoter, Moloney virus, ALV, Cytomegalovirus (CMV) such as the CMV immediate early promoter, Epstein Barr Virus (EBV), Rous Sarcoma Virus (RSV), as well as promoters from human genes such as human Actin, human Myosin, human Hemoglobin, human muscle creatine and human metalothionein.

Examples of polyadenylation signals useful with the nucleic acid compositions used in the present invention, especially in the production of a genetic vaccine for humans, include but are not limited to, SV40 polyadenylation signals and LTR polyadenylation signals. In particular, the SV40 polyadenylation signal which is in pCEP4 plasmid (Invitrogen, San Diego Calif.), referred to as the SV40 polyadenylation signal, may be used.

In addition to the regulatory elements required for nucleic acid molecule expression, other elements may also be included in the DNA molecule. Such additional elements include enhancers. The enhancer may be selected from the group including but not limited to: human Actin, human Myosin, human Hemoglobin, human muscle creatine, and viral enhancers such as those from CMV, RSV and EBV.

Nucleic acid compositions can be provided with mammalian origin of replication in order to maintain the construct extrachromosomally and produce multiple copies of the construct in the cell. Plasmids pCEP4 and pREP4 from Invitrogen (San Diego, Calif.) contain the Epstein Barr virus origin of replication and nuclear antigen EENA-1 coding region, which produces high copy episomal replication without integration. In aspects of the invention relating to gene therapy, constructs with origins of replication including the necessary antigen for activation are preferred.

In other embodiments of the present invention relating to immunization applications, the nucleic acid composition contains nucleotide sequences that encode a target protein and further include genes for proteins which enhance the immune response against such target proteins. Examples of such genes are those which encode cytokines and lymphokines such as α-interferon, γ-interferon, platelet derived growth factor (PDGF), GC-SF, GM-CSF, TNF, epidermal growth factor (EGF), IL-1, IL-2, IL-4, IL-6, IL-8, IL-10 and IL-12. In some embodiments, it will be preferred that the gene for GM-CSF be included in nucleic acid compositions used in immunizing compositions.

An additional element may be added to the nucleic acid composition which serves as a target for cell destruction, if it is desirable to eliminate the cells receiving the nucleic acid composition for any reason. A herpes thymidine kinase (tk) gene in an expressible form can be included in the nucleic acid composition. The drug gangcyclovir can then be administered to the individual and that drug will cause the selective killing of any cell producing tk, thus providing the means for the selective destruction of cells containing the nucleic acid composition.

In order to maximize protein production, regulatory sequences may be selected which are well suited for gene expression in cells into which the construct is transferred. Moreover, codons may be selected which are most efficiently transcribed in the target cell. One having ordinary skill in the art can readily produce DNA constructs which are functional in the target cells.

Nucleic acid compositions can be tested for expression levels in vitro by using tissue culture of cells of the same type as those to be treated. For example, if the genetic vaccine is to be administered to human muscle cells, muscle cells grown in culture, such as solid muscle tumors cells of rhabdomyosarcoma, may be used as an in vitro model to measure expression level.

The nucleic acid compositions used in the present invention are not incorporated within retroviral particles. The nucleic acid compositions are taken up by the cell without retroviral particle-mediated insertion, such as that which occurs when retrovirus particles with retroviral RNA, infects a cell. As used herein, the term "free from retroviral particles" is meant to refer to nucleic acid compositions that are not incorporated within retroviral particles. As used herein, "dissociated from an infectious agent" is meant to refer to genetic material which is not part of a viral, bacterial or eukaryotic vector, either active, inactivated, living or dead, that is capable of infecting a cell.

In some embodiments, the nucleic acid compositions constitute less than a complete, replicatable viral genome such that upon introduction into the cell, the nucleic acid composition possesses insufficient genetic information to direct production of infectious viral particles. As used herein, the term "incomplete viral genome" is meant to refer to a nucleic acid composition which contains less than a complete genome such that incorporation of such a nucleic acid composition into a cell does not constitute introduction of sufficient genetic information for the production of infectious virus.

In some embodiments, an attenuated viral vaccine may be delivered as a nucleic acid composition which contains enough genetic material to allow for production of viral particles. Delivery of the attenuated vaccine as a nucleic acid composition allows production of large quantities of safe, pure, and active immunizing product.

The present invention may be used to immunize an individual against all pathogens such as viruses, prokaryotic and pathogenic eukaryotic organisms such as unicellular pathogenic organisms and multicellular parasites. The present invention is particularly useful to immunize an individual against those pathogens which infect cells and which are not encapsulated, such as viruses, and prokaryotes such as Gonorrhoea, Listeria and Shigella. In addition, the present invention is also useful for immunizing an individual against protozoan pathogens, including any stage in their life cycle in which they are intracellular pathogens. As used herein, the term "intracellular pathogen" is meant to refer to a virus or pathogenic organism that, during at least part of its reproductive or life cycle, exists within a host cell and therein produces or causes to be produced, pathogenic proteins. Table 1 provides a listing of some of the viral families and genera for which vaccines according to the present invention can be made. DNA constructs that comprise DNA sequences which encode the peptides that comprise at least an epitope identical or substantially similar to an epitope displayed on a pathogen antigen, such as those antigens listed in said table, are useful in vaccines.

Moreover, the present invention is also useful to immunize an individual against other pathogens including prokaryotic and eukaryotic protozoan pathogens as well as multicellular parasites such as those listed in Table 2.

In order to produce a genetic vaccine to protect against pathogen infection, genetic material which encodes immunogenic proteins against which a protective immune response can be mounted, must be included in the nucleic acid composition. Whether the pathogen infects intracellularly, for which the present invention is particularly useful, or extracellularly, it is unlikely that all pathogen antigens will elicit a protective response. Because DNA and RNA are both relatively small and can be produced relatively easily, the present invention provides the additional advantage of allowing for vaccination with multiple pathogen antigens. The nucleic acid composition used in the genetic vaccine can include genetic material which encodes many pathogen antigens. For example, several viral genes may be included in a single construct, thereby providing multiple targets. In addition, multiple inoculants which can be delivered to different cells in an individual can be prepared to collectively include, in some cases, a complete or, more preferably, an incomplete, e.g., nearly complete set of genes in the vaccine. For example, a complete set of viral genes may be administered using two constructs which each contain a different half of the genome which are administered at different sites. Thus, an immune response may be invoked against each antigen without the risk of an infectious virus being assembled. This allows for the introduction of more than a single antigen target and can eliminate the requirement that protective antigens be identified.

The ease of handling and inexpensive nature of DNA and RNA further allow for more efficient means of screening for protective antigens. Genes can be sorted and systematically tested much more easily than proteins. Once the pathogenic agents and organism for which a protective vaccine will be sought is selected, an immunogenic protein is then identified. Tables 1 and 2 include lists of some of the pathogenic agents. and organisms for which genetic vaccines can be prepared to protect an individual from infection by them. The methods of immunizing an individual against a pathogen can be directed particularly against HIV, HTLV or HBV.

In accordance with the present invention there is also provided a method of conferring a broad based protective immune response against hyperproliferating cells that are characteristic of hyperproliferative diseases, as well as a method of treating individuals suffering from hyperproliferative diseases. As used herein, the term "hyperproliferative diseases" is meant to refer to those diseases and disorders characterized by hyperproliferation of cells. Examples of hyperproliferative diseases include all forms of cancer and psoriasis.

It has been discovered that introduction of a nucleic acid composition that includes a nucleotide sequence which encodes an immunogenic "hyperproliferating cell"-associated protein into the cells of an individual, results in the production of those proteins in the vaccinated cells of an individual. As used herein, the term "hyperproliferative-associated protein" is meant to refer to proteins that are associated with a hyperproliferative disease. To immunize against hyperproliferative diseases, a nucleic acid composition that includes a nucleotide sequence which encodes a protein that is associated with a hyperproliferative disease is administered to an individual.

In order for the hyperproliferative-associated protein to be an effective immunogenic target, it must be a protein that is produced exclusively or at higher levels in hyperproliferative cells as compared to normal cells. Target antigens include such proteins, fragments thereof and peptides which comprise at least an epitope found on such proteins. In some cases, a hyperproliferative-associated protein is the product of a mutation of a gene that encodes a protein. The mutated gene encodes a protein which is nearly identical to the normal protein except it has a slightly different amino acid sequence which results in a different epitope not found on the normal protein. Such target proteins include those which are proteins encoded by oncogenes such as myb, myc, fyn, and the translocation genes bcr/abl, ras, src, P53, neu, trk and EGRF. In addition to oncogene products as target antigens, target proteins for anti-cancer treatments and protective regimens include variable regions of antibodies made by B cell lymphomas, and variable regions of T cell receptors of T cell lymphomas which, in some embodiments, are also used as target antigens for autoimmune diseases. Other tumor-associated proteins can be used as target proteins, such as proteins which are found at higher levels in tumor cells, including the protein recognized by monoclonal antibody 17-1A and folate binding proteins.

While the present invention may be used to immunize an individual against one or more of several forms of cancer, the present invention is particularly useful to prophylactically immunize an individual who is predisposed to develop a particular cancer or who has had cancer and is therefore susceptible to a relapse. Developments in genetics and biotechnology, as well as epidemiology, allow for the determination of probability and risk assessment for the development of cancer in an individual. Using genetic screening and/or family health histories, it is possible to predict the probability that a particular individual has for developing any one of several types of cancer.

Similarly, those individuals who have already developed cancer and who have been treated to remove the cancer, or are otherwise in remission, are particularly susceptible to relapse and reoccurrence. As part of a treatment regimen, such individuals can be immunized against the cancer that they have been diagnosed as having had in order to combat such a recurrence. Thus, once it is known that individuals have had a type of cancer and are at risk of a relapse, they can be immunized in order to prepare their immune systems to combat any future appearance of the cancer.

The present invention also provides a method of treating individuals suffering from hyperproliferative diseases. In such methods, the introduction of nucleic acid compositions serves as an immunotherapeutic, directing and promoting the immune system of the individual to combat hyperproliferative cells that produce the target protein.

The present invention provides a method of treating individuals suffering from autoimmune diseases and disorders by conferring a broad based protective immune response against targets that are associated with autoimmunity, including cell receptors and cells which produce "self"-directed antibodies.

T cell mediated autoimmune diseases include Rheumatoid arthritis (RA), multiple sclerosis(MS), Sjogren's syndrome, sarcoidosis, insulin dependent diabetes mellitus (IDDM), autoimmune thyroiditis, reactive arthritis, ankylosing spondylitis, scleroderma, polymyositis, dermatomyositis, psoriasis, vasculitis, Wegener's granulomatosis, Crohn's disease and ulcerative colitis. Each of these diseases is characterized by T cell receptors that bind to endogenous antigens and initiate the inflammatory cascade associated with autoimmune diseases. Vaccination against the variable region of the T cells would elicit an immune response including CTLs to eliminate those T cells.

In RA, several specific variable regions of T cell receptors (TCRs) which are involved in the disease have been characterized. These TCRs include Vβ-3, Vβ-14, Vβ-17 and Vα-17. Thus, vaccination with a nucleic acid composition that encodes at least one of these proteins will elicit an immune response that will target T cells involved in RA. See: Howell, M. D., et al., 1991 *Proc. Natl. Acad. Sci. USA* 88:10921–10925; Paliard, X., et al., 1991 *Science* 253:325–329; Williams, W. V., et al.., 1992 *J. Clin. Invest.* 90:326–333; each of which is incorporated herein by reference.

In MS, several specific variable regions of TCRs which are involved in the disease have been characterized. These TCRs include Vβ-7 and Vα-10. Thus, vaccination with a nucleic acid composition that encodes at least one of these proteins will elicit an immune response that will target T cells involved in MS. See: Wucherpfennig, K. W., et al., 1990 *Science* 248:1016–1019; Oksenberg, J. R., et al., 1990 *Nature* 345:344–346; each of which is incorporated herein by reference.

In scleroderma, several specific variable regions of TCRs which are involved in the disease have been characterized. These TCRs include Vβ-6, Vβ-8, Vβ-14 and Vα-16, Vα-3C, Vα-7, Vα-14, Vα-15, Vα-16, Vα-28 and Vα-12. Thus, vaccination with a nucleic acid composition that encodes at least one of these proteins will elicit an immune response that will target T cells involved in scleroderma.

In order to treat patients suffering from a T cell mediated autoimmune disease, particularly those for which the variable region of the TCR has yet to be characterized, a synovial biopsy can be performed. Samples of the T cells present can be taken and the variable region of those TCRs identified using standard techniques. Genetic vaccines can be prepared using this information.

B cell mediated autoimmune diseases include Lupus (SLE), Grave's disease, myasthenia gravis, autoimmune hemolytic anemia, autoimmune thrombocytopenia, asthma, cryoglobulinemia, primary biliary sclerosis and pernicious anemia. Each of these diseases is characterized by antibodies which bind to endogenous antigens and initiate the inflammatory cascade associated with autoimmune diseases. Vaccination against the variable region of such antibodies would elicit an immune response including CTLs to eliminate those B cells that produce the antibody.

In order to treat patients suffering from a B cell mediated autoimmune disease, the variable region of the antibodies involved in the autoimmune activity must be identified. A biopsy can be performed and samples of the antibodies present at a site of inflammation can be taken. The variable region of those antibodies can be identified using standard techniques. Genetic vaccines can be prepared using this information.

In the case of SLE, one antigen is believed to be DNA. Thus, in patients to be immunized against SLE, their sera can be screened for anti-DNA antibodies and a vaccine can be prepared which includes nucleic acid compositions that encode the variable region of such anti-DNA antibodies found in the sera.

Common structural features among the variable regions of both TCRs and antibodies are well known. The DNA sequence encoding a particular TCR or antibody can generally be found following well known methods such as those described in Kabat, et al. 1987 *Sequence of Proteins of Immunological Interest* U.S. Department of Health and Human Services, Bethesda Md., which is incorporated herein by reference. In addition, a general method for cloning functional variable regions from antibodies can be found in Chaudhary, V. K., et al., 1990 *Proc. Natl. Acad. Sci. USA* 87:1066, which is incorporated herein by reference.

In aspects of the present invention that relate to gene therapy, the nucleic acid compositions contain either compensating genes or genes that encode therapeutic proteins. Examples of compensating genes include a gene which encodes dystrophin or a functional fragment, a gene to compensate for the defective gene in patients suffering from cystic fibrosis, a gene to compensate for the defective gene in patients suffering from ADA, and a gene encoding Factor VIII. Examples of genes encoding therapeutic proteins include genes which encodes erythropoietin, interferon, LDL receptor, GM-CSF, IL-2, IL-4 and TNF. Additionally, nucleic acid compositions which encode single chain antibody components which specifically bind to toxic substances can be administered. In some preferred embodiments, the dystrophin gene is provided as part of a mini-gene and used to treat individuals suffering from muscular dystrophy. In some preferred embodiments, a mini-gene which contains coding sequence for a partial dystrophin protein is provided. Dystrophin abnormalities are responsible for both the milder Becker's Muscular Dystrophy (BMD) and the severe Duchenne's Muscular Dystrophy (DMD). In BMD dystrophin is made, but it is abnormal in either size and/or amount. The patient is mild to moderately weak. In DMD no protein is made and the patient is wheelchair-bound by age 13 and usually dies by age 20. In some patients, particularly those suffering from BMD, partial dystrophin protein produced by expression of a mini-gene delivered according to the present invention can provide improved muscle function.

In some preferred embodiments, genes encoding IL-2, IL-4, interferon or TNF are delivered to tumor cells which are either present or removed and then reintroduced into an individual. In some embodiments, a gene encoding γ-interferon is administered to an individual suffering from multiple sclerosis.

Antisense molecules and ribozymes may also be delivered to the cells of an individual by introducing a nucleic acid composition which acts as a template for copies of such active agents. These agents inactivate or otherwise interfere with the expression of genes that encode proteins whose presence is undesirable. Nucleic acid compositions which contain sequences that encode antisense molecules can be used to inhibit or prevent production of proteins within cells. Thus, production of proteins such as oncogene products can be eliminated or reduced. Similarly, ribozymes can disrupt gene expression by selectively destroying messenger RNA before it is translated into protein. In some embodiments, cells are treated according to the invention using nucleic acid compositions that encode antisense or ribozymes as part of a therapeutic regimen which involves administration of other therapeutics and procedures. Nucleic acid compositions encoding antisense molecules and ribozymes use similar vectors as those which are used when protein production is desired except that the coding sequence does not contain a start codon to initiate translation of RNA into protein.

Ribozymes are catalytic RNAs which are capable of self-cleavage or cleavage of another RNA molecule. Several different types of ribozymes, such as hammerhead, hairpin, Tetrahymena group I intron, ahead, and RNase P are known in the art; see S. Edgington, *Biotechnology* (1992) 10, 256–262. Hammerhead ribozymes have a catalytic site which has been mapped to a core of less than 40 nucleotides. Several ribozymes in plant viroids and satellite RNAs share a common secondary structure and certain conserved nucleotides. Although these ribozymes naturally serve as their own substrate, the enzyme domain can be targeted to another RNA substrate through base-pairing with sequences flanking the conserved cleavage site. This ability to custom design ribozymes has allowed them to be used for sequence-specific RNA cleavage; see G. Paolella et al., *EMBO* (1992), 1913–1919.) It will therefore be within the skill of one in the art to use different catalytic sequences from various types of ribozymes, such as the hammerhead catalytic sequence, and design them in the manner disclosed herein. Ribozymes can be designed against a variety of targets including pathogen nucleotide sequences and oncogenic sequences. Preferred embodiments include sufficient complementarity to specifically target the abl-bcr fusion transcript while maintaining efficiency of the cleavage reaction.

In accordance with the present invention, the multifunctional molecular complex containing the desired nucleic acid composition, may be administered to an individual using a needleless injection device. In other embodiments, the multifunctional molecular complex containing the desired nucleic acid composition is simultaneously administered to an individual intradermally, subcutaneously and intramuscularly using a needleless injection device. Needleless injection devices are well known and widely available. One having ordinary skill in the art can, following the teachings herein, use needleless injection devices to deliver multifunctional molecular complexes containing the desired nucleic acid compositions to cells of an individual. Needleless injection devices are well suited to deliver these complexes to all of these tissues. They are particularly useful to deliver the complexes of the present invention to skin and muscle cells.

In some embodiments, a needleless injection device may be used to propel the complexes of the present invention in liquid form, that contains DNA molecules, toward the surface of the individual's skin. The liquid is propelled at a sufficient velocity such that upon impact with the skin, the liquid penetrates the surface of the skin, and permeates the skin and muscle tissue therebeneath. Thus, the nucleic acid composition is simultaneously administered intradermally, subcutaneously and intramuscularly. In some embodiments, a needleless injection device may he used to deliver nucleic acid compositions to the tissue of other organs in order to introduce a nucleic acid molecule to cells of that organ.

According to the present invention, the multifunctional molecular complexes containing nucleic acid compositions may be administered directly into the individual to be immunized or ex vivo into removed cells of the individual which are reimplanted after administration. By either route, the genetic material is introduced into cells which are present in the body of the individual. Routes of administration include, but are not limited to, intramuscular, intraperitoneal, intradermal, subcutaneous, intravenous, intraarterially, intraoccularly and oral as well as transdermally or by inhalation or suppository. Preferred routes of administration include intramuscular, intraperitoneal, intradermal and subcutaneous injection. Delivery of nucleic acid compositions which encode target proteins can confer mucosal immunity in individuals immunized by a mode of administration in which the material is presented to tissues associated with mucosal immunity. Thus, in some examples, the nucleic acid composition is delivered by administration to the buccal cavity within the mouth of an individual.

The multifunctional molecular complexes containing nucleic acid compositions according to the present invention comprise generally from about 1 nanogram to about 1000 micrograms of DNA. In some preferred embodiments, the complexes contain about 10 nanograms to about 800 micrograms of DNA. In more preferred embodiments, the complexes contain about 0.1 to about 500 micrograms of DNA. In still more preferred embodiments, the complexes contain about 1 to about 350 micrograms of DNA. In yet more preferred embodiments, the complexes contain about 25 to about 250 micrograms of DNA. In the most preferred embodiments, the complexes contain about 100 micrograms DNA.

The multifunctional molecular complexes containing nucleic acid compositions according to the present invention are formulated according to the mode of administration to be used. One having ordinary skill in the art can readily formulate a pharmaceutical composition that comprises a nucleic acid composition. In cases where intramuscular injection is the chosen mode of administration, an isotonic formulation is preferably used. Generally, additives for isotonicity can include sodium chloride, dextrose, mannitol, sorbitol and lactose. In some cases, isotonic solutions such as phosphate buffered saline are preferred. Stabilizers include gelatin and albumin. In some embodiments, a vasoconstriction agent is added to the formulation. The pharmaceutical preparations according to the present invention are prepared so as to be sterile and pyrogen free.

In addition to other agents which may function as transfecting agents and/or replicating agents, there may be co-administered with the complexes of the present invention growth factors, cytokines and lymphokines such as α-interferon, γ-interferon, platelet derived growth factor (PDGF), GC-SF, GM-CSF, TNF, epidermal growth factor (EGF), IL-1, IL-2, IL-4, IL-6, IL-8, IL-10 and IL-12, as well as fibroblast growth factor, surface active agents such as immune-stimulating complexes; (ISCOMS), Freund's incomplete adjuvant, LPS analog including monophosphoryl Lipid A (MPL), muramyl peptides, quinone analogs and vesicles such as squalene and hyaluronic acid may also be used, administered in conjunction with the complexes of the present invention. In some embodiments, combinations of these agents are administered in conjunction with the complexes of the present invention.

The complexes of the present invention may be combined with collagen as an emulsion and delivered parenterally. The collagen emulsion provides a means for sustained release of DNA; 50 $\mu$l to 2 ml of collagen may be used. About 100 $\mu$g of DNA are combined with 1 ml of collagen in a preferred embodiment using this formulation. Other sustained release formulations such as those described in *Remington's Pharmaceutical Sciences*, A. Osol, a standard reference text in this field, which is incorporated herein by reference. Such formulations include aqueous suspensions, oil solutions and suspensions, emulsions and implants as well as reservoirs, depots and transdermal devices. In some embodiments, time release formulations for the complexes are preferred; where it is desirable the complex be time released between 6–144 hours, preferably 12–96 hours, more preferably 18–72 hours.

In some embodiments of the invention, the individual is subject to a single vaccination to produce a full, broad immune response. In other embodiments of the invention, the individual is subject to a series of vaccinations to produce a full, broad immune response. According to still other embodiments of the invention, at least two and preferably four to five injections are given over a period of time. The period of time between injections may be from 24 hours part to two weeks or longer between injections, preferably one week apart. Alternatively, at least two and up to four separate injections are given simultaneously at different sites.

In some embodiments of the invention, a complete vaccination includes injection of a single inoculant which contains a nucleic acid composition including sequences encoding one or more targeted epitopes.

In other embodiments of the invention, a complete vaccination includes injection of two or more different inoculants into different sites. For example, an HIV vaccine may comprise two different inoculants in which each one comprises a nucleic acid composition encoding different viral proteins. This method of vaccination allows the introduction of as much as a complete set of viral genes into the individual without the risk of assembling an infectious viral particle. Thus, an immune response against most or all of the virus can be invoked in the vaccinated individual. Injection of each inoculant is performed at different sites, preferably at a distance to ensure that no cells receive the total combination of nucleic acid compositions. As a further safety precaution, some genes may be deleted or altered to further prevent the capability of infectious viral assembly.

In accordance with the present invention there are provided pharmaceutical compositions which facilitate delivery of the multifunctional molecular complex, which in turn functions to facilitate transfer of the nucleic acid composition which is contained therein, to the target cells. The pharmaceutical composition may be nothing more than an inert diluent and a pharmaceutically acceptable salt or ester form of said molecular complex. However, other pharmaceutically acceptable carriers well known to the artisan in this field, can also be suitably employed to provide desired properties. Thus, one or more agents may be selected from the following recognized pharmaceutical classes of excipients: solvents, solvent systems, and solubilizing and dispersing agents including surfactants and emulsifying agents; viscosity modifying agents; and stabilizing and preservative agents, including antioxidants, UV absorbing agents, antibacterial agents, and buffering agents.

The present invention also provides pharmaceutical kits which comprise a container comprising a nucleic acid composition, and a container comprising a transfer moiety. Optionally, there is included in such kits excipients, carriers, preservatives and vehicles of the type described above with respect to pharmaceutical compositions. The term pharmaceutical kit is also intended to include multiple inoculants used in the methods of the present invention. Such kits include separate containers comprising different inoculants and transfer moieties. The pharmaceutical kits in accordance with the present invention are also contemplated to include a set of inoculants used in immunizing methods and/or therapeutic methods, as described above.

The compositions and methods of the present invention are useful in the fields of both human and veterinary medicine. Accordingly, the present invention relates to genetic immunization and therapeutic treatment of mammals, birds and fish. The methods of the present invention can be particularly useful for genetic immunization and therapeutic treatment of mammalian species including human, bovine, ovine, porcine, equine, canine and feline species.

DESCRIPTION OF THE PREFERRED EMBODIMENTS

The Examples set out below include representative demonstrations of various aspects of the present invention. The Examples are not intended to limit the scope of the invention; but rather are merely intended to serve as illustrations thereof. Moreover, one having ordinary skill in this art will be able readily to appreciate additional aspects and embodiments of the present invention, based on the foregoing detailed description thereof. Unless otherwise indicated, all temperatures recited in the following Examples are Celsius scale temperatures.

EXAMPLE 1

Preparation of $N^4$-5'-Aminopentylspermidine Hydrochloride 8

$N^4$-(4-cyanobutyl)-$N^1$,$N^8$-Bis (tert-butyloxycarbonyl)Spermidine (6)

A solution of $N^1$,$N^8$-Bis(tert-butyloxycarbonyl) spermidine (2.92 g, 8.45 mmol, 1.0 eq) [S. Nagarajan and B. Ganem, *J. Org. Chem.*, 50, 5735–37 (1985)] in acetonitrile (125 mL) was treated with N,N-diisopropylethylamine (3.534 mL, 20.0 mmol, 2.4 eq), potassium iodide (2.81 g, 16.90 mmol, 2.0 eq), and 5-chlorovaleronitrile (1.902 mL, 16.90 mmol, 2.0 eq). The resulting homogeneous solution was heated to reflux for 2 hours. The mixture was treated with additional N,N-diisopropylethylamine (1.767 mL; 1.2 eq), potassium iodide (1.41 g, 1.0 eq) and 5-chlorovaleronitrile (0.951 mL, 1.0 eq), and refluxed an additional 18 hours. Thin layer chromatography (TLC) indicated no remaining starting material. The acetonitrile was removed under vacuum, and the residue taken up in chloroform (250 mL). This solution was washed with water (200 mL), dried ($Na_2SO_4$), and stripped of solvent to afford crude product as an oil. The material was purified on silica using a gradient of 2-propanol in chloroform plus 1% N,N-diisopropylethylamine to give an oil (3.40 g); $^1$H NMR (CDCl$_3$): δ1.44 (s, 20.8H; should be 18H), 1.58–1.80 (m, 9.8H), 2.38–2.44 (m, 9.4H; should be 8.0H), 3.16 (m, 4.1H), 4.80 (m, 0.8H), 5.38 (m, 0.8H).

$N^4$-(5-aminopentyl)-$N^1$, $N^8$-Bis(tert-butyloxycarbonyl)-Spermidine (7)

A solution of 6 (0.77 g, 1.81 mmol) in glacial acetic acid (100 mL) was treated with 5% palladium on carbon (0.08 g, 10% w/w) and placed on a Parr Hydrogenator (50 psi hydrogen gas pressure) for 2.75 hours. The mixture was filtered through Celite® brand diatomaceous earth filter aid (pre-rinsed with glacial acetic acid) and the Celite rinsed with chloroform. The filtrate and chloroform wash were combined and sovent removed to give an oil. The crude material was subjected to silica chromatography using a gradient of methanol in chloroform plus 0.4% diisopropylethylamine. The material consisted of a colorless oil (0.32 g). $^1$H NMR (CDCL$_3$): δ1.33 (m, 3.5H; should be 2.0H), 1.44 (s, 19.1H; should be 18.0H), 1.59 (m, 10.3H), 2.37–2.45 (m, 6.2H), 2.70 (t, 1.5H), 3.14 (m, 4.0H), 4.89 (m, 0.7H), 5.57 (m, 0.8H).

$N^4$-(5-Aminopentyl)spermidine Hydrochloride (8)

Compound 7 (0.200 g, 0.46 mmol) was stirred with trifluoroacetic acid (5 mL) at room temperature for 2 hours. The trifluoroacetic acid was removed under vacuum, followed by three chloroform additions and subsequent evaporations under vacuum. The resulting crude oil was twice taken up in 0.1 N HCl (30 mL) and lyophilized to give 8 as a hydroscopic solid (0.19 g).

EXAMPLE 2

Preparation of $N^4$-(5-(β-3'-propionyl galactosyl-β1"-4'-thioglucoside)aminopentyl)spermidine 9

S-(Succinimitdyl -β-3'-propionyl)hepta-O-acetyl galactosyl -β1'4-thioglucoside (10)

A solution of S-β-3'-propionyl hepta-O-acetyl galactosyl-β1-4-thioglucoside [M. Elofsson, S. Roy, B. Walse and J. Kihlberg, Carb. Res., 246, 89–103 (1993)] (4.60 g, 6.35 mmol) in 1:1 isopropanol/chloroform (100 mL) was treated with N-hydroxysuccinimide (0.73 g, 6.35 mmol) and N. N'-dicyclohexylcarbodiimide (1.31 g, 6.35 mmol). After stirring at room temperature for 19 hours, the mixture was cooled to 4° for 1 h and filtered. The solvent was removed from the filtrate under vacuum to give a white solid that was recrystallized from 2-propanol (3.43 g). The isolated product was 92% pure by high performance liquid chromatography (HPLC). $^1$H NMR (CDCL$_3$): δ2.0–2.16 (7s, 21.0H), 2.85 (s, 3.8H), 2.85–3.1 (m, 4.2H), 3.65 (m, 0.7H), 3.78 (t, 1.0H), 3.88 (t, 1.0H), 4.11 (m, 4.0H), 4.54 (m, 2.8H), 4.97 (m, 1.8H), 5.11 (m, 1.0H), 5.23 (t, 1.0H), 5.36 (d, 0.7H).

$N^4$ (5(S-β-3'-propionyl hepta-O-acetyl galactosyl-β1"-4'-thioglucoside)aminopentyl)-$N^1$,$N^6$-bis(tert-butyloxycarbonyl)-Spermidine (11)

A solution of 10 (0.300 g, 0.70 mmol) in methylene chloride (30 mL) was treated with a solution of 7 (0.57 g, 0.70 mmol) in methylene chloride (30 mL). The mixture was stirred at room temperature for 18 hours. The solvents were removed under vacuum. Silica chromatography using a gradient of 2-propanol in chloroform afforded purified product as a colorless glass (0.49 g); purity of 100% as determined by HPLC. $^1$H NMR (CDCl$_3$): δ1.33 (m, 3.0H; should be 2.0H), 1.44 (s, 20.0H; should be 18.0H), 1.54 (m, 10.7H; should be 6.0H), 1.68 (m, 2.0H), 1.97–2.16 (7s, 27.3H; should be 21.0H), 2.25 (m, 6.0H; should be 4H), 2.52 (m, 9.0H; should be 8.0H), 2.84 (m, 1.0H), 3.01 (m, 1.0H), 3.1–3.27 (m, 6.7H), 3.64 (m, 1.0H), 3.80 (t, 1.0H), 3.90 (t, 1.0H), 4.11 (m, 4.0H), 4.55 (d, 2.0H), 4.70 (d, 1.0H), 4.91–5.0 (m, 3.0H; should be 2.0H), 5.11 (m, 1.3H), 5.21 (t, 1.0H), 5.36 (d, 1.0H), 5.44 (m, 0.7H), 6.28 (m, 0.7H). FAB Mass Spec MH$^+$=1138.

$N^4$-(5-(S-β-3'-propionyl hepta-O-acetyl galactosyl-β1"-4'-thioglucoside)aminopentyl)spermidine trifluoroacetate (12)

Compound 11 (0.200 g, 0.18 mmol) was treated with trifluoroacetic acid (5 mL) and stirred at room temperature for 2 hrs. The trifluoroacetic acid (TFA) was largely removed under vacuum, and the residue subjected to three additions of chloroform, followed by removal of solvent under vacuum. The product was recovered as an oil (0.22 g) with trace TFA in evidence; purity of 100% as determined by HPLC $^1$H NMR (CDCL$_3$): δ1.25–1.53 (m, 5.5H), 1.6–2.0 (m, 5.5; should be 4H), 2.00–2.15 (7s, 23.0H; should be 21.0H), 2.56 (m, 1.0H), 2.68 (m, 1.3H), 2.80 (m, 1.0H), 3.0–3.4 (m, 11.0H; should be 10.0H), 3.64 (m, 1.0H), 3.79 (m, 1.0H), 3.94 (m, 1.0H), 4.11 (m, 2.5H), 4.55 (m, 1.5H), 4.70 (m, 1.3H), 4.90–5.20 (broad m, 16.0H; inflated by water; should be 2.0 or 4.0H), 5.36 (m, 1.0H), 7.12 (m, 0.5H), 7.86 (m, 2.3H), 8.07 (m, 2.3H), 9.8 (m. 0.5H).

$N^4$-(5-(β-3'-propionyl galactosyl-β1"-4'-thioglucoside)-aminopentyl)spermidine (9)

A solution of 12 (0.20 g; 0.18 mmol) in methanol (20 mL) was treated with sodium carbonate (0.38 g; 3.08 mmol; 18 eq) and water (35 mL) for a homogeneous solution. After 6 hrs at room temperature, the solvents were evaporated and the residue was desalted using Sephadex G-25 Medium gel filtration resin, and 1% glacial acetic acid as eluant. Fractions containing product were combined and lyophilized for pure product as the triacetate salt (0.10 g); purity of 100% as determined by HPLC. $^1$H NMR (DMSO-d$_6$ D$_2$O): δ1.15 (m or broad t, 1.5H), 1.3–1.5 (m, 8.0H), 1.65 (m, 2.0H), 1.66 (s, 14.0H; should be 9.0H), 2.34 (m, 6.5H), 2.60 (m, 3.0H; should be 2.0H), 2.74 (m, 6.0H), 3.00 (m, 3.0H), 3.27 (m, 3.5H), 3.40 (m, 1.5H), 3.47 (m, 2.0H), 3.50 (m, 1.0H), 3.60 (m, 1.0H), 3.71 (d, 1.0H), 4.14 (broad s, masked by water peak), 4.27 (m, 4.0H).

EXAMPLE 3

Preparation of $N^4$-(5-[$N^2$,$N^6$-bis(β-3'-propionyl galactosyl-β1-4-thioglucoside)lysyl-$N^6$(β-3'-propionyl galalactosyl-β1-4-thioglucoside)lysyl]-amino)pentylspermidine acetate salt 18

For comparative purposes, the CAS style name of the compound 18 set out above is as follows: 4-[($N^2$-[$N^2$,$N^6$-bis(3-[4-O(β-D-galactopyranosyl)-β-D-glucopyrylthio] propionyl)lysyl]$N^6$-(3-[4-O-(β-D-galactopyranosyl)-β-D-glucopyranosylthio]-propionyl)lysinamido)pentyl]-1,8-diamino-4-azaoctane, acetate salt.

$N^4$-(5-($N^2$,$N^6$-bis(β-3'-propionyl hepta-O-acetyl galactosyl-β1-4-thioglucoside)lysyl $N^6$-(β-3'-propionyl hepta-O-acetyl galactosyl-β1-4-thioglucoside) lysine (14)

To a solution of lysyl-lysine (0.25 g, 0.64 mmol) in 1:1 water/acetonitrile (100 mLs) was added N,N-diisopropylethylamine (0.336 mls, 1.95 mmol, 3.0 eq) and compound 10 (1.859, 2.25 mmol) and stirred at room temperature for a few minutes until homogeneity was achieved. The pH was closely monitored at regular intervals, and N,N-diisopropylethylamine added as needed to maintain the pH between 7 and 8. A total of 7 eq of base was added over 1 hour before the pH stabilized at 7–7.5. Reverse phase HPLC was used to follow the progress of the reaction. After 24 hrs at room temperature, the reaction appeared to have stopped with approximately 50% product formation. The acetonitrile was evaporated under vacuum, and the aqueous mixture treated with dilute HCl (pH 5). The solution was extracted into chloroform (2×200 mls). The combined organic layers were dried (Na$_2$SO$_4$), and the solvent removed under vacuum to afford crude product as a glass (2.17 g). The material was subjected to silica flash chromatography using a gradient of isopropanol in chloroform plus 1% glacial acetic acid as eluant (1.09 g). Purity was determined by HPLC to be approximately 96%. FAB Mass Spec: MH+=2394.

Succinimidyl $N^2$,$N^6$-bis(β-3'-propionyl hepta-O-acetyl galactosyl-β1-4-thioglucoside)lysyl-$N^6$-(β-3'-propionyl hepta-O-acetyl galactosyl-β1-4-thioglucoside)lysine (15)

A solution of $N^2$, $N^6$-bis(β-3'-propionyl hepta-O-acetyl galactosyl-β1-4-thioglucoside)lysyl-$N^6$-(β-3'-propionyl hepta-O-acetyl galactosyl-β1-4-thioglucoside)lysine (1.00 g, 0.42 mmol) in 1:1 isopropanol/chloroform (20 mL) was treated with N-hydroxysuccinimide (48.1 mg, 0.42 mmol) and N,N' dicyclohexylcarbodiimide (86.2 mg, 0.42 mmol). After stirring at room temperature for 19 hours, the mixture was cooled to 4° for 1 h and filtered. Solvent was removed from the filtrate under vacuum, and the crude product was recrystallized from 2-propanol. The product was collected by filtration and dried under vacuum to give a white powdery solid (0.76 g). This material was shown by HPLC to consist of a mixture of the starting free acid and the succinimidyl ester in a ratio of approximately 1:2 respectively. The mixture was not subjected to further purification, but was used as is in the next step. $^1$H NMR (CDCl$_3$): δ1.96–2.20 (multiple s, 86.4H; should be 63.0H), 2.28 (m, 3.6H), 2.53 (m, 6.6H), 2.88 (m, 6.6H), 3.02 (m, 3.6H), 3.18–3.40 (m, 4.2H), 3.62 (m, 3.6H), 3.85 (m, 3.6H), 3.95 (m, 3.6H), 4.10 (m, 12.0H), 4.57 (m, 6.0H), 4.70 (m, 4.2H), 5.02 (m, 7.2H), 5.10 (m, 3.6H), 5.20 (t, 3.6H), 5.36 (d, 3.0H), 6.31 (t, 0.6H), 6.58 (t, 0.6H), 6.90 (d, 0.6H), 7.47 (d, 0.6H).

$N^4$-(5-[$N^2$,$N^6$-bis(β-3'-propionyl hepta-O-acetyl galactosyl-β1-4-thioglucoside)lysyl-$N^6$-(β-3'-propionyl hepta-O-acetyl galactosyl-β1-4-thioglucoside)lysyl]-aminopentyl-$N^1$,$N^8$-Bis (tert-butoxycarbonyl)spermidine (16)

A solution of 7 (87 mg, 0.20 mmol) in methylene chloride (20 mL) was treated with a solution of 15 (0.76 g of the 66% mixture, corresponding to 0.50 g of the ester; 0.20 mmol) in methylene chloride (20 mL). The mixture was stirred at room temperature for 18 hrs, followed by removal of the solvent under vacuum. The crude product was purified by silica chromatography using a gradient of isopropanol in chloroform. The resulting impure product consisted of a 65:35 mixture of product to the free acid present as the contaminant in the starting ester. A second silica column using the same gradient plus 0.5% glacial acetic acid effectively isolated pure product (0.38 g); purity of 100% as determined by HPLC. $^1$H NMR (CDCl$_3$): δ1.30–1.39 (m, 4.0H), 1.44 (s, 13.5H; should be 18.0H), 1.53 (m, 8.6H), 1.60–1.90 (m, 6.1H), 1.97–2.16 (multiple s, 73.8H; should be 63.0H), 2.27 (m, 3.7H), 2.49–2.70 (m, 8.0H), 2.85 (m, 2.5H), 3.00 (m, 2.5H), 3.23 (m, 6.2H), 3.65 (m, 2.5H), 3.80–3.93 (m, 5.5H), 4.12 (m, 8.0H), 4.20–4.40 (m, 1.8H), 4.57–4.69 (m, 8.0H), 4.91–5.00 (m, 5.5H), 5.09 (m, 3.1H), 5.21 (t, 3.1H), 5.36 (d, 2.5H), 6.57 (m, 0.9H), 6.95 (m, 0.6H), 7.20 (m, 0.6H).

$N^4$-(5-[$N^2$, $N^6$-bis($\beta$-3'-propionyl hepta-O-acetyl galactosyl-$\beta$1-4-thioglucoside)lysyl-$N^6$-($\beta$-3'-propionyl hepta-O-acetyl galactosyl-$\beta$1-4-thioglucoside)lysyl]-aminopentyl)spermidine (17)

Compound 16 (0.170 g, 0.059 mmol) was treated with trifluoroacetic acid (5 mL) and stirred at room temperature for 2.5 hours. The trifluoroacetic acid was largely removed under vacuum (0.19 g). Purity was determined by HPLC to be approximately 100%. $^1$H NMR (CDCl$_3$): $\delta$1.20–1.80 (m, 4.8H), 1.96–2.15 (multiple s, 84.0H; should be 63.0H), 2.54 (m, 12.0H; possibly inflated by water peak), 3.65 (m, 3.0H), 3.81 (m, 3.0H), 3.93 (m, 4.0H), 4.12 (m, 12.0H), 4.29 (m, 2.0H), 4.55 (m, 6,0H), 4.69 (m, 4.0H), 4.89 (m, 3.0H), 5.09 (m, 6.0H), 5.19 (m, 4.0H), 5.38 (d, 3.0H), 6.99 (m, 1.0H), 7.60 (m, 0.5H), 7.91 (m, 1.0H), 8.09 (m, 1.0H).

$N^4$-(5-[$N^2$,$N^6$-bis($\beta$-3'-propionyl galactosyl-$\oplus$1-4-thioglucoside)lysyl-$N^6$-($\beta$-3'-propionyl galactosyl-$\oplus$1-4-thioglucoside)lysyl]-aminopentyl)spermidine acetate Salt (18)

To a solution of 17 (0.17 g, 0.059 mmol) in methanol (20 mL) was added sodium carbonate (0.37 g, 2.95 mol), followed by water (40 mL) until homogeneity was achieved. After stirring at room temperature for 4 hrs, the solvents were stripped off and the crude product eluted down a Sephadex G-25 Medium column using 1% glacial acetic acid as the eluant. Fractions containing product were combined and lyophilized to afford pure product as an extremely hygroscopic solid (0.07 g).

EXAMPLE 4

Preparation of $N^4$-(5-[$N^2$-$N^6$-bis($\beta$-3'-proplonyl galactosyl-$\beta$1-4-thioglucoside)lysyl]-aminopentyl) spermidine acetate Salt 23

Succinimidyl $N^2$, $N^6$-bis($\beta$-3'-propionyl hepta-O-acetyl galactosyl-$\oplus$1-4-thioglucoside)lysine (20)

A solution of $N^2$,$N^6$-bis($\beta$-3'-propionyl hepta-O-acetyl galactosyl-$\oplus$1-4-thioglucoside)lysine (1.00 g, 0.42 mmol) in 1:1 isopropanol/chloroform (20 mL) is treated with N-hydroxysuccinimide (48.1 mg, 0.42 mmol) and N,N'dicyclohexylcarbodiimide (86.2 mg, 0.42 mmol). After stirring at room temperature for 19 hours, the mixture is cooled to 4° for 1 h and filtered. Solvent is removed from the filtrate under vacuum, and the crude product recrystallized from 2-propanol. The product is collected by filtration and dried under vacuum to give a white powdery solid (0.76 g). This material is shown by HPLC to consist of a mixture of the starting free acid and the succinimidyl ester in a ratio of approximately 1:2 respectively. The mixture is not subjected to further purification, but is used as is in the next step.

$N^4$-(5-[$N^2$,$N^6$-bis($\beta$-3'-propionyl hepta-O-acetyl galactosyl-$\beta$1-4-thioglucoside)lysyl]aminopentyl)-$N^1$,$N^6$-Bis(tert-butoxycarbonyl)spermidine (21)

A solution of 7 (87 mg, 0.20 mmol) in methylene chloride (20 mL) is treated with a solution of 20 (0.769 of the 66% mixture, corresponding to 0.50 g of the ester; 0.20 mmol) in methylene chloride (20 mL). The mixture is stirred at room temperature for 18 hrs, followed by removal of the solvent under vacuum. The crude product is purified by silica chromatography using a gradient of isopropanol in chloroform. The resulting impure product consists of a 65:35 mixture of product to the free acid present as the contaminant in the starting ester. A second silica column using the same gradient plus 0.5% glacial acetic acid effectively isolates pure product (0.38 g); purity of 100% as determined by HPLC.

$N^4$-(5-[$N^2$,$N^6$-bis($\beta$-3'-propionyl hepta-O-acetyl galactosyl-$\beta$1-4-thioglucoside)lysyl]aminopentyl) spermidine (22)

Compound 21 (0.170 g, 0.059 mmol) is treated with trifluoroacetic acid (5 mL) and stirred at room temperature for 2.5 hours. The trifluoroacetic acid is largely removed under vacuum (0.19 g). Purity is determined by HPLC to be approximately 100%.

$N^4$-(5-[$N^2$,$N^6$-bis($\beta$-3'-propionyl galactosyl-$\oplus$1-4-thioglucoside)lysyl]aminopentyl)spermidine acetate Salt (23)

To a solution of 22 (0.17 g, 0.059 mmol) in methanol (20 mL) is added sodium carbonate (0.37 g, 2.95 mmol), followed by water (40 mL) until homogeneity is achieved. After stirring at room temperature for 4 hrs, the solvents are stripped off and the crude product is eluted down a Sephadex G-25 Medium column using 1% glacial acetic acid as the eluant. Fractions containing product are combined and lyophilized to afford pure product as an extremely hydroscopic solid (0.07 g).

EXAMPLE 5

Preparation of $N^4$-5-(D-biotinyl)aminopentyl spermidine hydrochloride Salt 24

To a solution of 7 (0.20 g, 0.47 mmol) in 20 mL of acetonitrile and 10 mL of water was added 160 mg of succinimidyl D-biotin. The solution was stirred for 18 h. The volume of the solution was reduced to 15 mL under vacuum and the remaining solution was purified on octadecylsilyl bonded silica using a water/acetonitrile gradient containing 0.1% trifluoroacetic acid. Fractions containing the product were combined and solvent removed under vacuum to give a waxy white solid (94% pure by HPLC). To the white solid was added 10 mL of 2-propanol and 10 mL of 4 N HCl in dioxane. The solvents were removed under vacuum. The resultant white solid was redissolved in water and dried under vacuum to give a hygroscopic foam (0.11 g). $^1$H NMR (DMSO-d$_6$) $\delta$1–31 (m, 4H), 1.44 (m, 6H), 1.64 (m, 8H), 2.09 (m, 4H), 2.63 (d, 2H), 2.91 (m, 4H), 3.06 (m, 8H), 4.18 (m, 1H), 4.36 (m, 1H).

EXAMPLE 6

Preparation of $N^4$-(5-cholestene-3'$\beta$-oxycarbonyl) aminopentyl spermidine hydrochloride Salt 25

To a solution of 7 (0.20 g, 0.47 mmol) in 20 ML of methylene chloride was added 210 mg of cholesteryl chloroformate and 200 $\mu$L of diisopropylethylamine. The solution was stirred for 24 h. The methylene chloride was removed under vacuum and the remaining oil was redissolved in chloroform and purified on silica using a methanol/chloroform gradient containing 0.1% diisopropylethylamine. Fractions containing the product were combined and solvent removed under vacuum to give a waxy white solid (0.29 g). To the white solid was added 10 mL of 2-propanol and 10 mL of 4 N HCl in dioxane. The solvents were removed under vacuum. The resultant white solid was redissolved in water and dried under vacuum to give a waxy white solid (0.15 g).

EXAMPLE 7

Preparation of $N^4$-octyl-$N^1,N^8$-Bis(tert-butyloxycarbonyl)spermidine 26

To a solution of $N^1,N^8$-Bis(tert-butyloxycarbonyl) spermidine (1.0 g, 2.89 mmol) in acetone (100 mls) was added N,N-diisopropylethylamine (0.605 mls, 3.47 mmol, 1.2 eq), potassium iodide (0.489, 2.89 mmol), and 1-bromooctane (0.500 mls, 2.89 mmol). The mixture was heated to reflux for one hour, followed by the addition of N,N-diisopropylethylamine (0.605 mls, 3.47 mmol) and potassium iodide (0.48 g, 2.89 mmol). After an additional 3 hrs reflux, 1-bromooctane (0.500 mls, 2.89 mmol) was added and refluxing continued for an additional hour. The acetone was evaporated under vacuum. The residue taken up in chloroform (125 mls) and washed with water (2×75 mls). The organic layer was dried (Na2 504), and solvent removed under vacuum to give a liquid. The liquid was purified by silica chromatography using a gradient of isopropanol in chloroform plus 1% N,N-diisopropylethylamine. The pure product was recovered as a pale orange oil (0.59 g). $^1H$ NMR (CDCl3): δ0.88 (t, 3.5H), 1.27 (m, 14.2H; should be 16.0H), 1.44 (s, 18.7H), 1.58 (m, 1.6H) 1.82 (m, 1.6H), 2.37 (m, 2.4H), 2.44 (m, 2.2H), 3.19 (m, 4.0H), 4.84 (m, 0.3H), 5.62 (m, 0.3H).

The $N^4$-octyl-$N^1,N^8$-Bis(tert-butyloxycarbonyl) spermidine (0.15 g) was dissolved in 6 mL of 4 N HCl in dioxane and stirred at room temperature for 1 h. The solvent was removed under vacuum and the yellow oil suspended in chloroform and the solvent removed under vacuum. The resultant oil was dissolved in 10 mL of absolute ethanol and precipitated by the addition of 30 mL of diethyl ether. The solid was isolated by decanting off the liquid and drying under vacuum (0.10 g). $^1H$ NMR (DMSO-$d_6$): δ0.86 (m, 3H), 1.28 (m, 10H), 1.58–1.80 (m, 6H), 2.00 (m, 2H), 2.80 (m, 2H), 2.89 (m, 2H), 3.03 (m, 4H), 3.15 (m, 2H), 8.01 and 8.13 (two m, 5H, should be 6H). Anal: Calcd for $C_{15}H_{38}Cl_3N_3C$ 49.11, H 10.44, N 11.45. Found C 48.57, H10.75, N 11.29.

EXAMPLE 8

Preparation of $N^4$-dodecylspermidine trihydrochloride 27

A solution of $N^1,N^8$-Bis(tert-butyloxycarbonyl) spermidine (0.50 g, 1.45 mmol) in acetone (50 mLs) was treated with N,N-diisopropylethylamine (0.604 mLs, 3.48 mmol), potassium iodide (0.48 g, 2.90 mmol), and 1-bromododecane (0.348 mLs, 2.90 mmol). The mixture was refluxed for 18 hrs and was treated with additional 1-bromododecane (0.348 mLs, 2.90 mmol). Refluxing was continued for 4 hours. The acetone was removed under reduced pressure, and the residue taken up in chloroform (250 mLs). The solution was washed with water (2×100 mLs). The organic layer was dried ($Na_2S)_4$), and the solvent removed for crude product. The material was purified by silica flash chromatography eluting with a gradient of isopropanol in chloroform plus 0.4% N,N-diisopropylethylamine. The pure product was recovered as an oil of mass 0.52 g. $^1H$ NMR (CDCl$_3$): δ0.88 (t, 3.0H), 1.26 (broad s, 21.0H; should be 20.0H), 1.44 (s, 20.5; should be 18.0H), 1.64 (m, 5.8H), 2.37 (m, 3.8H), 2.46(t, 2.5H), 3.15 (m, 4.0H), 4.84 (m, 0.5H), 5.62 (m, 0.8H).

The $N^1,N^8$-Bis(tert-butyloxycarbonyl)-$N^4$-dodecyl-spermidine (0.52 g, 1.01 mmol) was dissolved in 2-propanol (5 mLs) and treated with 4N HCl in dioxane (10 mLs). The homogeneous solution was stirred at room temperature for 20 hrs, and the solvents were evaporated under reduced pressure. The crude oil was taken up in ethanol (20 mLs) and treated with ether (10–15 mLs) with stirring. A solid precipitated out of solution and was collected by filtration (85 mgs). A second crop was recovered for an additional 79 mgs. Total yield was 164 mgs. $^1H$ NMR (DMSO-$d_6$): δ0.86 (t, 2.3H), 1.25 (m, 18.0H), 1.63 (m, 3.7H), 1.76 (m, 2.3H), 1.99 (m,1.3H), 2.79 (m, 2.0H), 2.90 (m, 2.0H), 3.02 (m, 3.7H), 3.16 (m, 2.3H), 8.03 (m, 1.7H), 8.14 (m, 2.7H).

EXAMPLE 9

Preparation of $N^4$-hexadecylspermidine trihydrochloride 28

A solution of $N^1,N^8$-Bis(tert-butyloxycarbonyl) spermidine (0.50 g, 1.45 mmol) in acetone (50 mLs) was treated with N,N-diisopropylethylamine (0.302 mLs, 1.74 mmol, 1.2 eq), potassium iodide (0.24 g, 1.45 mol) and 1-bromohexadecane (0.442 mLs, 1.45 mmol). The mixture refluxed for 20 hrs, and the solvents were removed under vacuum. The residue was taken up in chloroform (250 mLs) and washed with water (150 mLs). The organic layer was dried ($Na_2SO_4$), and the solvent evaporated under reduced pressure to afford crude product as an amber oil. The material was purified by silica flash chromatography using a gradient of isopropanol in chloroform plus 0.4% N,N-diisopropylethylamine. The pure product was recovered as a pale yellow oil, mass 0.42 g. $^1H$ NMR (CDCl$_3$) δ0.88 (t, 2.9H), 1.26 (broad s, 30.3H; should be 28.0H), 1.44 (s, 22.9H; should be 18.0H), 1.60 (m, 4.0H), 1.72 (m, 1.7H), 2.37 (m, 3.7H), 2.46 (m, 2.9H; should be 2.0H), 3.17 (m, 4.0H), 4.83 (m, 0.6H), 5.62 (m, 0.6H).

The $N^1,N^8$-Bis(tert-butyloxycarbonyl)-$N^4$-hexadecyl-spermidine (0.42 g, 0.74 mmol), was dissolved in 2-propanol (5 mLs) and was treated with 4N HCl in dioxane (10 mLs). The homogeneous solution was stirred at room temperature for 1.5 hrs, followed by evaporation of the solvents under reduced pressure. The residue was taken up in ethanol (12 mLs) and was treated with ether (10 mLs) with stirring. A precipitate fell out of solution and was collected by filtration; mass 125 mgs. A second crop was recovered of mass 75 mgs for a total yield of 0.200 g. $^1H$ NMR (DMSO-$d_6$+$D_2O$) δ0.83 (t, 2.1H; should be 3.0H), 1.22 (m, 26.6H), 1.54–1.70 (m, 6.0H), 1.96(m, 1.7H), 2.81 (m, 1.7H), 2.89 (m, 2.1H), 3.04–3.12 (m, 6.0H).

EXAMPLE 10

Transfection of Adherent Cells In Culture Using Receptor Bearing Cells

Human hepatocellular carcinoma HuH7 cells were grown and seeded into a 96 well plate with 1–2×10$^4$ cells in 100 μL of minimal essential media α, modification with 10% serum. The plates were incubated in a 37° $CO_2$ incubator until the cells were 60–80% confluent (approximately 24 hrs). The media was removed and the cells washed once with Optimem® (serum free media). Optimem® (100 μL) containing 0.5 μg of pCMVβ plasmid (from Clonetech, No. 6177-1), 0.5 μg of $N^4$-(5-[$N^2,N^6$-bis(β-3'-propionyl galactosyl-β1-4- thioglucoside)lysyl-N$^6$-(β-3'-propionyl galactosyl-β1-4-thioglucoside)lysyl]aminopentyl)-spermidine and 2.5 μg of N$^4$-(5-cholestene-3'β-oxycarbonyl)-aminopentyl) spermidine was added to the cells. The cells were incubated with the mixture for 4 hrs in a 37° $CO_2$ incubator; thereafter 100 μL of media containing 20% serum was added and the incubation continued for an additional 20 hrs. Cells lysed with 0.5% NP-40 in 140 mM NaCl, 10 mM tris, 1.5 mM $MgCl_2$ were assayed for β-galactosidase activity using o-nitrophenyl β-D-galactopyranoside, and gave $A_{405}$=1.35 after 30 min. Cells grown in 6 well plates (25 mm diameter) and treated similarly were fixed with 2% paraformaldehyde and assayed for β-galactosidase activity using 5-bromo-4-chloro-3-indolyl β-D-galactopyranoside (J. Sambrook, et al., Molecular Cloning: A Laboratory Manual, Cold Spring Harbor, 1989). Visual inspection showed 5–10% of the cells were transfected as evidenced by light microscopy. Similar results were obtained when the receptor specific binding component of the multifunctional molecular complex was omitted from the cell culture, while retaining the endosome membrane disruption promoting component of the multifunctional molecular complex.

Similar results were obtained with N$^4$-(5-(β-3'-propionyl galactosyl-β1-4-thioglucoside)aminopentyl)spermidine; and N$^4$-(5-(methyltetrahydrofolyl)aminopentyl)spermidine; with the endosome membrane disruption promoting components included therein. Similar results can also be obtained with N$^4$-octylspermidine; N$^4$-dodecylspermidine; fusogenic peptides acylated on the N-terminus by N$^4$-(5-carboxypentyl)spermidine; N$^4$-(5-(3α, 7α, 12α-trihydroxy-5β-cholan-24-oic)aminopentyl)spermidine amide, with the receptor specific binding components included therein.

EXAMPLE 11

Transfection of Muscle Cells In Vivo

Solutions were prepared containing 100 μg of pCMVβ plasmid and 100 μg of either N$^4$-octylspermidine, N$^4$-dodecylspermidine or N$^4$-(5-cholestene-3'β-oxycarbonyl)aminopentyl)spermidine, each in 100 μL of phosphate buffered saline. The plasmid solution (100 μL) was injected into the rear quadriceps of 6–12 week old BALB-C mice. The mice were sacrificed approximately 96 hrs later and the entire quadriceps muscle tissue was removed. The muscle was fixed with formalin for 2 hrs, and assayed for β-galactosidase activity using 5-bromo-4-chloro-3-indolyl-β-D-galactopyranoside (1 mg/mL in tris/EDTA pH 8.5). All three injections were scored as positive since the blue color was more intense than the control: injection of 100 μg of pCMVβ plasmid injected in 100 μL of 0.25% bupivicaine hydrochloride in citrate buffer pH 6.0. Similar results can also be obtained with fusogenic peptides acylated on the N-terminus by N$^4$-(5-carboxypentyl) spermidine; and N$^4$-(5-(3α, 7α, 12α-trihydroxy-5β-cholan-24-oic)aminopentyl)spermidine amide.

EXAMPLE 12

Transfection of Liver Cells In Vivo

A solution is prepared containing 10 μg of pHBVSA plasmid, 5 μg of N$^4$-(5-[N$^2$,N$^6$-bis(β-3'-propionyl galactosyl-⊕1-4-thioglucoside)lysyl-N$^6$-(β-3'-propionyl galactosyl-β1-4-thioglucoside)lysyl]aminopentyl) spermidine and 25 μg of N$^4$-(5-cholestene-3'β-oxycarbonyl) aminopentyl)spermidine in 100 μL of phosphate buffered saline. The plasmid solution (100 μL) is injected into the tail vein of 6–12 week old BALB-C mice. The mice are sacrificed 48–120 hrs later and the serum tested for hepatitis B surface antigen using a commercial enzyme-linked immunoassay. The production of surface antigen is greater than the positive control supplied with the kit at 48 hrs post-injection.

Similar results are obtained with N$^4$-(5-(β-3'-propionyl galactosyl-β1-4-thioglucoside)aminopentyl)spermidine; N$^2$,N$^6$-(5-[bis(β-3'-propionyl galactosyl-β1-4-thioglucoside)lysyl]aminopentyl)spermidine; N$^4$-(5-(methyltetrahydrofolyl)aminopentyl)spermidine; N$^4$-(5-(folinyl)aminopentyl)spermidine; N$^4$-(5-(α-3'-propionyl thiomannoside)aminopentyl)spermidine and N$^4$-(5-(α-3'-propionyl thiomannoside-6-phosphate)aminopentyl) spermidine, with the receptor specific binding components included therein.

Similar results can also be obtained with N$^4$-octylspermidine; N$^4$-dodecylspermidine, fusogenic peptides acylated on the N-terminus by N$^4$-(5-carboxypentyl) spermidine; N$^4$-(5-(cholest-5-en-3'-β-carbamoyl)-aminopentyl)spermidine; and N$^4$-(5-(3α, 7α, 12α-trihydroxy-5β-cholan-24-oic)aminopentyl)-spermidine amide, with the endosome membrane disruption promoting component included therein.

EXAMPLE 13

A Kit for Research and Manufacturing Use

A kit for using the multifunctional molecular complexes of the present invention in a research and manufacturing setting, where the individual users supply their own DNA, includes a vial containing the transfer. moiety of the present invention dissolved at 0.1 to 10 mg/mL and preferably at 1 mg/mL in a sterile buffer at pH 6–8 and preferably at pH 6.5 to 7.5. Acceptable buffers would include citrate, HEPES and phosphate. Use of the kit involves removing an aliquot of transfer moiety and adding the aliquot to the solution of DNA (at 0.05 to 2 mg/mL, and preferably 0.25 to 0.75 mg/mL), such that the final ratio of mg of transfer moiety to mg DNA is between 0.5 and 5.0 mg/mg. Optimal ratios can be readily determined. The DNA-transfer moiety mixture is mixed briefly and held at 37° for 15–60 minutes. The DNA-transfer moiety mixture, which has now formed the multifunctional molecular complex of the present invention, is then diluted with minimal essential media (serum free) to a concentration of 5 to 100 μg/mL and added to the cells in culture. Optimal concentrations can be readily determined.

EXAMPLE 14

A Kit for Clinical and Veterinary Use

A kit for using the transfer moieties of the present invention in a clinical or veterinary setting, where the individual users supply their own DNA, includes a vial containing the transfer moiety dissolved at 0.1 to 10 mg/mL and preferably at 1 mg/mL in a sterile buffer at pH 6–8 and preferably at pH 6.5 to 7.5. Acceptable buffers include citrate, HEPES and phosphate. Use of the kit involves removing an aliquot of transfer moiety and adding the aliquot to the solution of DNA (at 0.05 to 2 mg/mL, and preferably 0.25 to 0.75 mg/mL), such that the final ratio of mg of transfer moiety to mg DNA is between 0.5 and 5.0 mg/mg and is preferably 1 mg/mg. Optimal ratios can be readily determined. The DNA-compound mixture is mixed briefly and held at ambient temperature for 30–60 minutes. The DNA-transfer moiety mixture (10 to 500 μg of DNA), which has now formed the multifunctional molecular complex of the present invention, is then injected into the patient or subject, human or animal, as is consistent with the desired application, e.g., i.m. injection for immunization, i.v. injection for liver localization, etc.

EXAMPLE 15

A Kit for Clinical and Veterinary Use, Including DNA

A kit for using the multifunctional molecular complexes of the present invention in a clinical or veterinary setting, where the DNA is supplied as part of the kit, includes a vial containing the compound dissolved at 0.05 to 10 mg/mL and preferably at 0.5 to 1 mg/mL in a sterile buffer at pH 6–8, and preferably at pH 6.5 to 7.5. Acceptable buffers include citrate, HEPES and phosphate. The kit also contains DNA appropriate for the intended use (at 0.05 to 2 mg/$\mu$L, and preferably 0.25 to 0.75 mg/mL), such that the final ratio of mg of the transfer moiety component of the kit to mg of the DNA component of the kit, is between 0.5 and 5.0 mg/mg, and is preferably 1 mg/mg. Optimal ratios can be readily determined. The DNA-transfer moiety mixture is held at ambient temperature for 30–60 minutes. The DNA-transfer moiety mixture (10 to 500 $\mu$g of DNA), is then injected into the patient or subject, human or animal, as is consistent with the desired application, e.g., i.m. injection for immunization, i.v. injection for liver localization, etc.

EXAMPLE 16

Kit Containing Lyophilized Components

The kits described in Examples 13 through 15 above, can also have the components thereof supplied as lyophilized powders where the transfer moieties, buffer components and excipients are reconstituted at the site of use by the addition of sterile water. These lyophilized kits can also include the DNA as a lyophilized component.

EXAMPLE 17

Preparation of $N^4$-(benzyl 6'-hexanoyl)-spermidine trihydrochloride

Benzyl 6-bromohexanoate was prepared by dropwise addition of a solution of 6-bromohexanoyl chloride (20.0 mL) in 100 mL of methylene chloride to a solution of 66.22 mL of benzyl alcohol in 60 mL of pyridine. The mixture was cooled using an ice-water bath for 90 min, then stirred at room temperature for 18 h. The solution was extracted with 200 mL of 1 N HCl followed by 2×150 mL of sat. NaHCO$_3$. The extracts were discarded and the solution dried over Na$_2$SO$_4$. The solution was filtered and the solvent removed in vacuo to give an oil. This oil was purified on silica gel, eluting with a gradient of chloroform in hexanes. Fractions containing the product (TLC R$_f$ 0.52, CHCl$_3$/hexanes 6:4) were combined and the solvent removed to give 24.4 g.

$N^4$-(benzyl 6'-hexanoyl)-$N^1$,$N^8$-bis(tert-butyloxycarbonyl)spermidine was prepared by treating $N^1$,$N^8$-bis(tert-butyloxycarbonyl)spermidine (3.0 g) with three aliquots of benzyl 6-bromohexanoate (2.45 g each) and K$_2$CO$_3$ (1.19 g each) in one hour intervals in refluxing acetonitrile. The solvent was removed in vacuo and the residue partitioned between 200 mL of water and 2×150 mL of CHCl$_3$. The CHCl$_3$ layers were combined, dried over Na$_2$SO$_4$, filtered and the solvent removed in vacuo to give an oil. This oil was purified on silica gel, eluting with a gradient of methanol in chloroform. Fractions containing the product (TLC R$_f$ 0.50, CHCl$_3$/methanol 9:1) were combined and the solvent removed to give 3.82 g of $N^4$-(benzyl 6'-hexanoyl)-$N^1$,$N^8$-bis(tert-butyloxycarbonyl)spermidine as an oil.

$N^4$-(benzyl 6'-hexanoyl)-$N^1$,$N^8$-bis(tert-butyloxycarbonyl)spermidine (0.20 g) was dissolved in 10 mL of trifluoroacetic acid and stirred at room temperature for one hour. The trifluoroacetic acid was removed in vacuo, and the residue dissolved twice in chloroform (50 mL) and the solvent removed in vacuo. The oily residue was lyophilized from 10 mL of 0.1 N HCl to give 126 mg of $N^4$-(benzyl 6'-hexanoyl)-spermidine trihydrochloride as an oil. NMR (DMSO-d$_6$) $\delta$1.37 (2H), 1.77 (9.4H), 2.05 (2H), 2.42 (1.8H), 2.9 (1.7H), 3.00 (4.4H), 3.20 (1.7H), 5.12 (1.7H), 7.37 (5H), 8.19 (5H), 10.77 (1H).

EXAMPLE 18

Preparation of $N^4$-(6'-hexanoyl)-spermidine-HA-2 Peptide $N^4$-(6'-hexanoic acid)-$N^1$,$N^8$-bis (tert-butyloxycarbonyl) spermidine (1.46 g) was treated with 0.37 g of N-hydroxysuccinimide and 0.66 g of N,N'-dicyclohexylcarbodiimide in 100 mL of tetrahydrofuran for 20 h. The precipitate was removed by filtration and the solvent removed in vacuo to give 1.99 g of $N^4$-(succinimidyl 6'-hexanoyl)-$N^1$,$N^8$-bis(tert-butyloxycarbonyl)spermidine. The peptide SGSGGLFEAIAENGWEGMIDGGG was prepared using an ABI Model 431A peptide synthesizer, pre-loaded FMOC-amino acid cartridges and pre-loaded FMOC-Gly-p-alkoxy-benzyl alcohol resin. The FMOC protecting group was removed from the N-terminal serine and the resin dried. The peptide-resin was treated with 1.99 g of $N^4$-(succinimidyl 6'-hexanoyl)-$N^1$,$N^8$-bis(tert-butyloxycarbonyl)spermidine and 1.24 mL of diisopropyl-ethylamine in 50 mL of dimethylformamide for 24 h. The resin was isolated by filtration and rinsed with dichloromethane. The $N^4$-(6'-hexanoyl)-spermidine-SGSGGLFEAIAENGWEGMIDGGG-OH was cleaved from the resin using a mixture of water (0.25 mL), ethanedithiol (0.25 mL), thioanisole (0.50 mL) and trifluoroacetic acid (9.5 mL). The spent resin was removed by filtration and the crude $N^4$-(6'-hexanoyl)-spermidine-SGSGGLFEAIAENGWEGMIDGGG-OH precipitated by addition of diethyl ether and isolated by filtration. A sample of the crude $N^4$-(6'-hexanoyl)-spermidine-SGSGGLFEAIAENGWEGMIDGGG-OH (100 mg) was purified by HPLC on a 25×250 mm C-18 column eluting with a gradient of 0.05 M ammonium bicarbonate and 0.05 M ammonium bicarbonate in 80% acetonitrile. FAB mass spectra MH$^+$=2775.

EXAMPLE 19

Preparation of $N^4$-(5'-N-(3"$\alpha$, 7"$\alpha$, 12"$\alpha$-trihydroxy-5"$\beta$-cholanamido)pentyl)-spermidine trihydrochloride Cholic acid (95 mg) was dissolved in 10 mL of tetrahydrofuran and N-hydroxysuccinimide (27 mg) and dicyclohexylcarbodiimide (48 mg) added. The mixture was stirred to dissolve and $N^4$-(5'-aminopentyl)-$N^1$,$N^8$-bis(tert-butyloxycarbonyl)-spermidine (100 mg) added. The mixture was stirred at room temperature 48 h. The solvent was removed in vacuo. The crude wax was purified on silica gel, eluting with a gradient of methanol in chloroform. Fractions containing the product (TLC $R_f$ 0.39, CHCl$_3$/methanol 85:15) were combined and the solvent removed to give 0.15 g of $N^4$-(5'-(3"α, 7"α, 12"α-trihydroxy-5"β-cholanamido) pentyl)-$N^1,N^8$-bis(tert-butyloxycarbonyl)spermidine as a white solid. This solid was dissolved in 10 mL of 2-propanol and to this solution was added 10 mL of 4 N HCl in dioxane. The mixture was stirred for 18 h at room temperature, during this time $N^4$-(5'-(3"α, 7|α, 12"α-trihydroxy-5"βcholanamido)pentyl)spermidine trihydrochloride precipitated as a fine white powder. This was isolated by filtration to give 67 mg. NMR (DMSO-d$_6$) δ0.58 (s, 3H), 0.81 (s, 3H), 0.92 (m, 5.5H), 1.28 (m, 20.8H), 1.62 (m, 16.2H), 2.05 (m, 8.8H), 2.8 (q, 2.8H), 2.9 (q, 2.8H), 3.02 (q, 8.3H), 3.18 (m, 4.4H), 7.87 (m, 1.1H), 8.13 (br s, 4H), 8.23 (br s, 4H), 10.78 (br s, 1.1H).

EXAMPLE 20

Preparation of $N^4$-(5-N-(α-3'-propionamido thiomannoside)pentyl)-spermidine trihydrochloride A solution of S-α-3'-propionyl tetra-O-acetyl-thiomannoside (prepared similarly to S-β-3'-propionyl hepta-O-acetyl-galactosyl-β1-4-thioglucoside, M. Elofsson, S. Roy, B. Walse and J. Kihlberg, Carb. Res., 246, 89–103 (1993)) (0.90 g) was prepared in 50 mL of CHCl$_3$. To the solution was added 5 mL of 2-propanol, 0.43 g of dicyclohexylcarbodiimide and 0.24 g of N-hydroxysuccinimide. The solution was stirred at room temperature for 1 h, then stored at 4° overnight. A precipitate was filtered off and solvent removed from the filtrate in vacuo to give an oil. The oil was dissolved in 30 mL of tetrahydrofuran. To this solution was added a solution of $N^4$-(5'-aminopentyl)-$N^1$,$N^8$-bis(tert-butyloxycarbonyl)-spermidine (0.86 g) (in 50 mL tetrahydrofuran and 30 mL of water) and 0.55 mL of diisopropylethylamine. The solution was stirred at room temperature for 2 h, the resultant solids were filtered off and the solvent removed in vacuo to give an oil. The oil was suspended in 100 mL of sat NaHCO$_3$ and extracted with 2×75 mL of CHCl$_3$. The solution was dried over Na$_2$SO$_4$ filtered and the solvent removed to give an oil. The oil was purified on silica gel, eluting with a gradient of methanol in chloroform. Fractions containing the product (TLC $R_f$ 0.30, CHCl$_3$/methanol 9:1) were combined and the solvent removed to give 0.10 g of $N^4$-(5'-N-(S-α-3'-propionamido tetra-O-acetyl-thiomannoside)pentyl)-$N^1,N^8$-bis(tert-butyloxycarbonyl)spermidine as a glass. This glass was dissolved in 10 mL of trifluoroacetic acid and the mixture was stirred for 1 h at room temperature. Solvent was removed in vacuo and the residue redissolved and solvent removed using chloroform (3×20 mL). The solid was treated with 15% NH$_4$OH in 55% ethanol for two hours. The product was then lyophilized (3×) from 0.05 N HCL to give $N^4$-(5-(α-3'-propionyl thiomannoside)aminopentyl)-spermidine trihydrochloride as a white solid (64 mg).

EXAMPLE 21

Preparation of $N^4$-(N-CBZ-5-aminopentyl)-spermidine trihydrochloride $N^4$-(N-CBZ-5'-aminopentyl)-$N^1,N^8$-bis(tert-butyloxycarbonyl)spermidine was prepared similarly to $N^4$-(benzyl 6'-hexanoyl)-$N^1,N^8$-bis(tert-butyloxycarbonyl) spermidine by treating $N^1,N^8$-bis(tert-butyloxycarbonyl) spermidine (0.5 g) with four aliquots of N-CBZ-5-amino-1-bromopentane (1.74 g each) and five aliquots of K$_2$CO$_3$ (1.00 g each). The resultant oil was purified on silica gel, eluting with a gradient of methanol in chloroform (TLC $R_f$ 0.47, CHCl$_3$/methanol 9:1+0.4% diisopropylethylamine) to give 0.72 g of $N^4$-(N-CBZ-5'-aminopentyl)-$N^1,N^8$-bis(tert-butyloxycarbonyl)spermidine as an oil.

$N^4$-(N-CBZ-5'-aminopentyl)-$N^1,N^8$-bis(tert-butyloxycarbonyl)spermidine (0.24 g) was dissolved in 10 mL of trifluoroacetic acid and stirred in an ice-water bath under nitrogen for 2 hours. Cold ether was added to precipitate the product as an oil. The solvents were removed by decantation and the oil dissolved in 25 mL of 0.1 N HCL and lyophilized to give 0.16 g of $N^4$-(N-CBZ-5-aminopentyl)-spermidine trihydrochloride as a glass. NMR (DMSO-d$_6$) δ1.28 (m, 2H), 1.47 (m, 2H), 1.61 (m, 8H), 2.01 (m, 2H), 2.82, 2.90 (m, 4H), 3.02 (m, 8H), 3.15 (m, 2.7H), 5.01 (s, 2H), 7.35 (s+m, 6.7H), 8.00, 8.11 (overlapping br m, 7.3H).

EXAMPLE 22

Preparation of $N^4,N^9$-bis(N-CBZ-5-aminopentyl)-spermine tetrahydrochloride $N^1,N^{12}$-bis(tert-butyloxycarbonyl)spermine was prepared similarly to $N^1,N^8$-bis(tert-butyloxycarbonyl)spermidine using the same sequence of reactions. $N^4,N^9$-bis(N-CBZ-5'-aminopentyl)-$N^1,N^{12}$-bis(tert-butyloxycarbonyl)spermine was prepared similarly to $N^4$-(N-CBZ-5'-aminopentyl)-$N^1$, $N^8$-bis(tert-butyloxycarbonyl)spermidine using a single addition of N-CBZ-5-amino-1-bromopentane (5.10 g) and K$_2$CO$_3$ (4.70 g) to 3.42 g of $N^1,N^{12}$-bis(tert-butyloxycarbonyl)spermine in refluxing acetonitrile (100 mL). Workup as before gave the product as an oil which was purified on silica gel, eluting with a gradient of methanol in chloroform containing diisopropylethylamine (0.2%). Fractions containing the product (TLC $R_f$ 0.43, CHCl$_3$/methanol 9:1+0.4% diisopropylethylamine) were combined and the solvent removed to give 6.0 g of $N^4,N^9$-bis(N-CBZ-5'-aminopentyl)-$N^1,N^{12}$-bis(tert-butyloxycarbonyl)spermine as an oil. An aliquot (0.25 g) of this material was deprotected an converted to the hydrochloride as described above for $N^4$-(N-CBZ-5-aminopentyl)-spermidine trihydrochloride to give 0.13 g of $N^4,N^9$-bis(N-CBZ-5-aminopentyl)-spermine tetrahydrochloride.

NMR (DMSO-d$_6$) δ1.28 (m, 4H), 1.43 (m, 4H), 1.76 (m, 8.8H), 2.01 (m, 4H), 2.90, 3.00 (overlapping m, 18.4H), 3.17 (m, 4.4H), 5.03 (s, 4H), 7.35 (s, 12H), 8.11 (br m, 5.6H).

EXAMPLE 23

Preparation of $N^4,N^9$-bis(octyl)-spermine tetrahydrochloride $N^4,N^9$-bis(octyl)-$N^1,N^{12}$-bis (tert-butyloxycarbonyl) spermine was prepared using a single addition of 1-bromooctane (0.53 g), potassium iodide (0.45 g) and diisopropylethylamine (0.54 mL) to 0.50 g of $N^1,N^{12}$-bis (tert-butyloxycarbonyl)spermine in acetone (30 mL) and refluxing overnight. The acetone was removed in vacuo and the mixture taken up in 200 mL of chloroform and washed with 100 mL of water. The chloroform solution was dried over Na$_2$SO$_4$, filtered and solvent removed in vacuo to give the product as an oil. This oil was purified on silica gel, eluting with a gradient of methanol in chloroform. Fractions containing the product (TLC $R_f$ 0.54, CHCl$_3$/methanol 9:1) were combined and the solvent removed to give 0.26 g of $N^4,N^9$-bis(octyl)-$N^1,N^{12}$-bis(tert-butyloxycarbonyl) spermine as a wax. This material (0.26 g) was treated with 10 mL of 4 N HCl in dioxane for two hours at room temperature. The solvent was removed in vacuo to give 0.21 g of $N^4,N^9$-bis(octyl)-spermine tetrahydrochloride as a wax.

NMR (DMSO-d$_6$) δ0.94 (t, 6H), 1.35 (m, 22H), 1.74, 1.83 (overlapping m, 8.2H), 2.10 (m, 4H), 2.97, 3.12, 3.26 (overlapping m, 18H), 8.27 (br m, 5.6H).

EXAMPLE 24

Preparation of 1,12-bis-N-guanidino-N$^4$,N$^9$-bis(octyl)-4,9-diaza-dodecane tetrahydrochloride To 0.68 g of N$^4$,N$^9$-bis(octyl)-spermine tetratrifluoroacetate in 50 mL of tetrahydrofuran and 1 mL of water was added 0.77 g of N,N'-bis(tert-butyloxycarbonyl)-S-methylisothiourea and 0.85 mL of diisopropylethylamine. The solution was refluxed for 1 h then stirred at room temperature for 18 h. The solvent was removed under a stream of nitrogen at 60°. the resultant solid was suspended in 100 mL of sat. NaHCO$_3$ and extracted with 2×100 mL of chloroform. The chloroform solution was dried over Na$_2$SO$_4$, filtered and solvent removed in vacuo to give an oil. This oil was purified on silica gel, eluting with a gradient of methanol in chloroform. Fractions containing the product (TLC R$_f$ 0.39, CHCl$_3$/methanol 9:1) were combined and the solvent removed to give 0.18 g of 1,12-bis-N-(N',N''-bis-(tert-butyloxycarbonyl-guanidino))-N$^4$,N$^9$-bis(octyl)-4,9-diazadodecane as a wax. This wax was dissolved in 10 mL of trifluoroacetic acid and stirred at room temperature for 1 hour. The solvent was removed in vacuo and the residue dissolved in chloroform and the solvent removed (2×20 mL) to give an oil. This oil was dissolved in 30 mL of 0.1 N HCl and lyophilized to give 1,12-bis-N-guanidino-N$^4$,N$^9$-bis(octyl)-4,9-diaza-dodecane tetrahydrochloride (86 mg) as oil. NMR (MeOH-d$_4$) δ0.82 (m, 3H), 1.23, 1.30 (overlapping m, 10H), 1.64, 1.71 (overlapping m, 4H), 1.90 (m, 2H), 3.14 (m, 6H).

EXAMPLE 25

Preparation of N$^4$-(5-N-(cholestene-3'β, carbamoyl) pentyl)-spermine tetrahydrochloride N$^4$-(N-CBZ-5'-aminopentyl)-N$^1$,N$^{12}$-bis(tert-butyloxycarbonyl)spermine was isolated as a minor component during the preparation of N$^4$,N$^9$-bis(N-CBZ-5'-aminopentyl)-N$^1$,N$^{12}$-bis(tert-butyloxycarbonyl)spermine. Fractions containing the N$^4$-(N-CBZ-5'-aminopentyl)-N$^1$,N$^{12}$-bis(tert-butyloxycarbonyl)spermine (TLC R$_f$ 0.26, CHCl$_3$/methanol 9:1+0.4% diisopropylethylamine) were combined and the solvent removed to give 0.84 g of an oil. To this oil was added 50 mL of acetonitrile, 0.47 mL of diisopropylethylamine and 0.35 g of di-tert-butyl dicarbonate. The mixture was stirred at room temperature for 4 h. The solvent was removed in vacuo and the residue taken up in 100 mL of chloroform and washed with 100 mL of water. The chloroform solution was dried over Na$_2$SO$_4$, filtered and the solvent removed in vacuo to give 0.83 g of N$^4$-(N-CBZ-5'-aminopentyl)-N$^1$,N$^9$,N$^{12}$-tris(tert-butyloxycarbonyl)spermine an oil, single spot by TLC (R$_f$0.56, CHCl$_3$/methanol 9:1+0.4w diisopropylethylamine). The N$^4$-(N-CBZ-5'-aminopentyl)-N$^1$,N$^9$,N$^{12}$-tris(tert-butyloxycarbonyl)spermine (0.22 g) in 20 mL of methanol was treated with 0.04 g of 10%Pd/C and 50 PSIG H$_2$ for 2 h at room temperature. The Pd/C was removed by filtration through diatomaceous earth and the solvent removed in vacuo to give N$^4$-(5'-aminopentyl)-N$^1$,N$^9$,N$^{12}$-tris(tert-butyloxycarbonyl)spermine as an oil (0.14 g). This oil was dissolved in methylene chloride and to the solution was added diisopropylethylamine (0.146 mL) and cholesteryl chloroformate (0.094 g). The solution was stirred at room temperature for 24 h. The solvent was removed in vacuo and the resultant oil was purified on silica gel, eluting with a gradient of methanol in chloroform containing diisopropylethylamine. Fractions containing the product (TLC R$_f$ 0.29, CHCl$_3$/methanol 9:1+0.4% diisopropylethylamine) were combined and the solvent removed to give 0.19 g of N$^4$-(5-N-(cholestene-3'β carbamoyl)pentyl)-N$^1$,N$^9$,N$^{12}$-tris(tert-butyloxycarbonyl)spermine as an oil. This oil was dissolved in 5 mL of trifluoroacetic acid and stirred under nitrogen in an ice-water bath for 2 h. The solvent was removed in vacuo and the residue dissolved in chloroform and the solvent removed (2×20 mL) to give an oil. This oil was dissolved in 10 mL of 0.1 N HCl and lyophilized to give a light brown oil (0.077 g). NMR (DMSO-d$_6$) δ0.58 (s, 3H), 0.78 (two s, 6H), 0.90 (overlapping m, 18H), 1.43 (overlapping m, 15H), 1.64 (overlapping m, 8H), 1.96 (m, 6H), 2.85 (overlapping m, 16H), 3.12 (m, 4H), 5.25 (m, 1H), 7.0 (br t, 1H), 8.06 (br m, 8H), 9.19 (br m, 2H).

EXAMPLE 26

Preparation of N$^4$, N$^9$-bis(N,N-dimethyl 12'-dodecanamide)-spermine tetrahydrochloride To a suspension of 7.8 g of 12-bromododecanoic acid in 100 mL of water was added 14 mL of 2 M dimethylamine in tetrahydrofuran resulting in a clear solution. The pH was adjusted to 7 with 1 N HCl and 5.36 g of 1-(3-dimethylaminopropyl)-3-ethylcarbodiimide was added. The solution was stirred at room temperature for 18 h. The resultant N,N-dimethyl 12-bromododecanamide precipitated out of solution as a white solid during this time. This solid was filtered off and wash with water, then dried in vacuo. N$^4$,N$^9$-bis(N,N-dimethyl 12'-dodecanamide)-N$^1$, N$^{12}$-bis(tert-butyloxycarbonyl)spermine was prepared similarly to N$^4$-(N-CBZ-5'-aminopentyl)-N$^1$,N$^8$-bis (tert-butyloxycarbonyl)spermidine using a single addition of N,N-dimethyl 12-bromododecanamide (2.34 g) and K$_2$CO$_3$ (1.70 g) to 0.50 g of N$^1$,N$^{12}$-bis(tert-butyloxycarbonyl) spermine in refluxing acetonitrile (50 mL). Workup as before gave the product as an oil which was purified on silica gel, eluting with a gradient of methanol in chloroform containing diisopropylethylamine (0.2%). Fractions containing the product (TLC R$_f$ 0.53, CHCl$_3$/methanol 8:2+ 0.2% diisopropylethylamine) were combined and the solvent removed to give 0.49 g of N$^4$,N$^9$-bis(N,N-dimethyl 12'-dodecanamide)-N$^1$,N$^{12}$-bis(tert-butyloxycarbonyl) spermine as an oil. An aliquot (0.20 g) of this material was deprotected and converted to the hydrochloride as described above for N$^4$-(N-CBZ-5-aminopentyl)-spermidine trihydrochloride to give 0.19 g of N$^4$,N$^9$-bis(N,N-dimethyl 12'-dodecanamide)-spermine tetrahydrochloride. NMR (DMSO-d$_6$) δ1.26 (m, 25.6H), 1.46 (m, 3H), 1.70, 1.80 (overlapping m, 6H), 2.04 (m, 3H), 2.79 (s, 6H), 2.94 (s, 6H), 3.0–3.2 (overlapping m, 18H), 8.15 (br m, 5H).

EXAMPLE 27

Preparation of N$^4$,N$^9$-bis(benzyl 12'-dodecanoyl)-spermine tetrahydrochloride To a solution of 12-brmododecanoic acid (1.0 g) and benzyl alcohol (0.74 mL) in 200 mL of toluene was added p-toluenesulfonic acid (0.10 g). Most (ca. 180 mL) of the toluene was removed by simple distillation at atmospheric pressure, and the remaining solvent removed in vacuo. The residue was taken up in ethyl acetate (200 mL) and washed with sat. NaHCO$_3$. The ethyl acetate solution was dried over Na$_2$SO$_4$, filtered and the solvent removed in vacuo to give crude benzyl 12-bromododecanoate (1.75 g) as a crude liquid. TLC (chloroform/hexane 85:15) showed only product ($R_f$ 0.78) and benzyl alcohol ($R_f$ 0.08). $N^4,N^9$-bis(benzyl 12'-dodecanoyl)-$N^1,N^{12}$-bis(tert-butyloxycarbonyl) spermine was prepared similarly to $N^4$-(N-CBZ-5'-aminopentyl)-$N^1,N^8$-bis(tert-butyloxycarbonyl)spermidine using a single addition of crude benzyl 12-bromododecanoate (4.6 g) and $K_2CO_3$ (1.70 g) to 1.0 g of $N^1,N^{12}$-bis(tert-butyloxycarbonyl)spermine in refluxing acetonitrile (100 mL). Workup as before gave the product as an oil which was purified on silica gel, eluting with a gradient of methanol in chloroform. Fractions containing the product (TLC $R_f$ 0.35, $CHCl_3$/methanol 9:1) were combined and the solvent removed to give 0.36 g of $N^4,N^9$-bis(benzyl 12'-dodecanoyl)-$N^1,N^{12}$-bis(tert-butyloxycarbonyl) spermine as an oil. An aliquot (0.27 g) of this material was deprotected and converted to the hydrochloride as described above for $N^4$-(N-CBZ-5-aminopentyl)-spermidine trihydrochloride to give 0.17 g of $N^4,N^9$-bis(benzyl 12'-dodecanoyl)-spermine tetrahydrochloride. NMR (DMSO-$d_6$) δ1.24 (m, 31.4H), 1.55 (m, 4.2H), 1.70, 1.80 (overlapping m, 8.6H), 2.02 (m, 4.2H), 2.9–3.2 (overlapping m, 21.4H), 5.08 (s, 4.2H), 7.36 (s, 10H) 8.13 (br m, 5.8H).

EXAMPLE 28

Preparation of $N^4,N^9$-bis(12'-dodecanoic acid)-spermine tetrahydrochloride $N^4,N^9$-bis (benzyl 12'-dodenanoyl)-$N^1,N^{12}$-bis(tert-butyloxycarbonyl)spermine (0.51 g) was dissolved in 50 mL of methanol and treated with 0.05 g of 10%Pd/C and 50 PSIG $H_2$ for 3 h at room temperature. The Pd/C was removed by filtration through diatomaceous earth. The solvent was removed from the filtrate in vacuo to give $N^4,N^9$-bis(12'-dodecanoic acid)-$N^1,N^{12}$-bis(tert-butyloxycarbonyl) spermine as an oil. An aliquot (0.22 g) of this material was deprotected and converted to the hydrochloride as described above for $N^4$-(N-CBZ-5-aminopentyl)-spermidine trihydrochloride to give 0.17 g of $N^4,N^9$-bis(12'-dodecanoic acid)-spermine tetrahydrochloride. NMR (DMSO-$d_6$) δ1.25 (m, 28H), 1.47 (m, 5H), 1.66, 1.76 (overlapping m, 8H), 2.02 (m, 3.6H), 2.91–3.17 (overlapping m, 19H), 8.11 (br m, 5H).

EXAMPLE 29

Preparation of $N^4$-(benzyl 12'-dodenanoyl)-spermine tetrahydrochloride $N^4$-(benzyl 12'-dodenanoyl)-$N^1,N^{12}$-bis(tert-butyloxycarbonyl)spermine was prepared similarly to $N^4$-(N-CBZ-5'-aminopentyl)-$N^1,N^8$-bis (tert-butyloxycarbonyl) spermidine using a single addition of benzyl 12-bromododecanoate (6.58 g) to 1.43 g of $N^1,N^{12}$-bis(tert-butyloxycarbonyl)spermine in refluxing acetonitrile (100 mL). Workup as before gave the product as an oil which was purified on silica gel, eluting with a gradient of methanol in chloroform containing diisopropylethylamine (0.2%). Fractions containing the product (TLC $R_f$ 0.08, $CHCl_3$/methanol 8:2+0.2% diisopropylethylamine) were combined and the solvent removed to give 0.36 g of $N^4$-(benzyl 12'-dodenanoyl)-$N^1,N^{12}$-bis(tert-butyloxycarbonyl)spermine as an oil. An aliquot (0.29 g) of this material was deprotected and converted to the hydrochloride as described above for $N^4$-(N-CBZ-5-aminopentyl)-spermidine trihydrochloride to give 0.19 g of $N^4$-(benzyl 12'-dodenanoyl)-spermine tetrahydrochloride. NMR (DMSO-$d_6$) δ1.24 (m, 12H), 1.53 (m, 1.5H), 1.69, 1.80 (overlapping m, 4H), 2.01 (m, 4H), 2.9–3.2 (overlapping m, 14H), 5.08 (s, 2H), 7.36 (s, 5H) 7.47 (m, 1H), 8.09 (br m, 5.5H), 9.20 (br m, 2H).

EXAMPLE 30

Preparation of $N^4$-(12'-dodecanoic acid)-spermine tetrahydrochloride $N^4$-(benzyl 12'-dodenanoyl)-$N^1,N^{12}$-bis(tert-butyloxycarbonyl)spermine (0.29 g) was dissolved in 30 mL of methanol and treated with 0.03 g of 10%Pd/C and 50 PSIG $H_2$ for 1.5 h at room temperature. The Pd/C was removed by filtration through diatomaceous earth. The solvent was removed from the filtrate in vacuo to give $N^4$-(12'-dodecanoic acid)-$N^1,N^{12}$-bis(tert-butyloxycarbonyl) spermine as an oil (0.19 g). This material (0.19 g) was deprotected and converted to the hydrochloride as described above for $N^4$-(N-CBZ-5-aminopentyl)-spermidine trihydrochloride to give 0.18 g of $N^4$-(12'-dodecanoic acid)-spermine tetrahydrochloride. NMR (DMSO-$d_6$) δ1.26 (m, 16.7H), 1.48 (m, 2.7H), 1.70, 1.78 (overlapping m, 6H), 2.01 (m, 4H), 2.91–3.17 (overlapping m, 12H), 8.17 (br m, 5.3H), 9.30 (br m, 2H).

EXAMPLE 31

Preparation of $N^4,N^9$-bis(5-(α-3'-propionyl thiomannoside)aminopentyl)-spermine tetraacetate $N^4,N^9$-bis(N-CBZ-5'-aminopentyl)-$N^1,N^{12}$-bis(tert-butyloxycarbonyl)spermine (2.04 g) was dissolved in 50 mL of methanol and treated with 0.84 g of 10%Pd/C and 50 PSIG $H_2$ for 2.5 h at room temperature. The Pd/C was removed by filtration through diatomaceous earth and solvent removed from the filtrate in vacuo to give $N^4,N^9$-bis (5'-aminopentyl)-$N^1,N^{12}$-bis(tert-butyloxycarbonyl) spermine (0.79 g) as an oil. A solution of S-α-3'-propionyl tetra-O-acetyl-thiomannoside (2.94 g) was prepared in 100 mL of tetrahydrofuran. To the thiomannoside solution was added 1.39 g of dicyclohexylcarbodiimide and 0.78 g of N-hydroxysuccinimide. The solution was stirred at room temperature for 20 h, then stored at 4° for 0.5 h. A precipitate was filtered off and solvent removed from the filtrate in vacuo to give succinimidyl S-α-3'-propionyl tetra-O-acetyl-thiomannoside (3.80 g) as a white solid. The $N^4,N^9$-bis(5'-aminopentyl)-$N^1,N^{12}$-bis(tert-butyloxycarbonyl)spermine (0.79 g) was dissolved in tetrahydrofurax (75 mL) and to the solution was added 0.64 mL of diisopropylethylamine and 1.32 g of succinimidyl S-α-3'-propionyl tetra-O-acetyl-thiomannoside, and the solution stirred at room temperature for 24 h. The solvent was removed in vacuo to give a glass. This glass was purified on silica gel, eluting with a gradient of methanol in chloroform containing diisopropylethylamine (0.2%). Fractions containing the product (TLC $R_f$ 0.30, $CHCl_3$/methanol 9:1) were combined and the solvent removed to give 0.69 g of $N^4,N^9$-bis(5-(α-3'-propionyl tetra-O-acetyl thiomannoside)aminopentyl)-$N^1,N^{12}$-bis(tert-butyloxycarbonyl)spermine as a glass. This glass was dissolved in 20 mL of trifluoroacetic acid and stirred at room temperature for 1 h. The solvent was removed in vacuo and the residue dissolved in chloroform and the solvent removed (2×20 mL) to give 0.78 g of $N^4,N^9$-bis(5-N-(α-3'-propionamido tetra-O-acetyl thiomannoside)pentyl)-spermine as an oil. This oil was dissolved in 25 mL of methanol and to the solution was added 25 mL of water and 1.56 g of $Na_2CO_3$, and the solution stirred at room temperature for 5 h. The solvents were removed in vacuo and the residue taken up in 6 mL of 1% acetic acid and purified in three 2 mL aliquots on three Sephadex™ G-25 medium columns (12 mL each), eluting with 1% acetic acid. Fractions containing the product were combined and lyophilized to give 0.31 g of $N^4,N^9$-bis(5-N-(α-3'-propionamido thiomannoside)pentyl)-spermine tetraacetate as a white solid. NMR (D$_2$O) δ1.42 (m, 4H), 1.59 (m, 4H), 1.79 (m, 9.5H), 1.95 (s, 38.5H), 2.14 (m, 5H), 2.62 (t, 4H), 2.94 (m, 4H), 3.10 (m, 4.5H), 3.24 (m, 18H), 3.72 (m, 6H), 4.05 (m, 6.5H), 5.34 (s, 2H).

EXAMPLE 32

Preparation of N$^4$-(5-N-(23'-N-(α-3"-propionamido thiomannoside)-3',6',9',12'-15'-18'-hexa-oxa-tricosanamido)aminopentyl)-spermine tetraacetate A solution of pentaethylene glycol (5.0 g) in 50 mL of tetrahydrofuran was added to a rapidly stirred suspension of NaH (0.42 g of 60%) in 40 mL of tetrahydrofuran. The reaction mixture was kept under nitrogen and suspended in an ice-water bath and stirred for 0.5 h. A solution of N-CBZ-5-amino-1-bromopentane (3.78 g) in 30 mL of tetrahydrofuran was added and the mixture stirred in the ice-water bath for 1 h, then at room temperature for 18 h. The solvent was removed in vacuo and the residue was purified on silica gel, eluting with a gradient of 2-propanol in chloroform. Fractions containing the product (TLC R$_f$ 0.30, CHCl$_3$/2-propanol 95:5) were combined and the solvent removed to give 3.25 g of N-CBZ-20-amino-3,6,9,12,15-penta-oxa-1-eicosanol as an oil. A solution of N-CBZ-20-amino-3,6,9,12,15-penta-oxa-1-eicosanol (3.25 g) in 50 mL of tetrahydrofuran was added to a rapidly stirred suspension of NaH (0.28 g of 60%) in 25 mL of tetrahydrofuran. The reaction mixture was kept under nitrogen and suspended in an ice-water bath and stirred for 0.5 h. To the solution was added tert-butyl 1-bromoacetate (1.15 mL) and the mixture stirred in the ice-water bath for 1 h, then at room temperature for four days. The solvent was removed in vacuo and the residue suspended in 100 mL of chloroform and washed with water (50 mL). The chloroform solution was dried over Na$_2$SO$_4$, filtered and the solvent removed in vacuo to give an oil. This oil was purified on silica gel, eluting with a gradient of 2-propanol in chloroform. Fractions containing the product (TLC R$_f$ 0.45, CHCl$_3$/2-propanol 95:5) were combined and the solvent removed to give 3.24 g of tert-butyl N-CBZ-23-amino-3,6,9,12,15,18-hexa-oxa-1-tricosanoate as a colorless oil. An aliquot of the tert-butyl N-CBZ-23-amino-3,6,9,12,15,18-hexa-oxa-1-tricosanoate (0.49 g) was dissolved in 10 mL of 4 N HCl in dioxane and stirred at room temperature for 3 h. The solvents were removed in vacuo. The resultant crude N-CBZ-23-amino-3,6,9,12,15,18-hexa-oxa-1-tricosanoic acid was dissolved in 15 mL of dimethylformamide. To this solution was added N-hydroxysuccinimide (0.10 g), 1-(3-dimethylaminopropyl)-3-ethyl carbodiimide (0.16 g) and N$^4$-(5'-aminopentyl)-N$^1$,N$^9$,N$^{12}$-tris(tert-butyloxycarbonyl) spermine (0.50 g). The solution was stirred at room temperature for 2.5 days. The dimethylformamide was removed in vacuo and the residue taken up in chloroform (100 mL). The chloroform solution was washed sequentially with 0.1 N HCL (75 mL) and sat. NaHCO$_3$. The chloroform solution was dried over Na$_2$SO$_4$, filtered and the solvent removed in vacuo to give an oil. This oil was purified on silica gel, eluting with a gradient of 2-propanol in chloroform. Fractions containing the product (TLC R$_f$ 0.33, CHCl$_3$/methanol 9:1) were combined and the solvent removed to give 0.19 g of N$^4$-(5-N-(N-CBZ-23'-amino-3',6',9',12'-15'-18'-hexa-oxa-tricosanamido)aminopentyl)-N$^1$,N$^9$,N$^{12}$-tris(tert-butyloxycarbonyl)spermine as a colorless oil. This oil was dissolved in 50 mL of ethyl acetate and treated with 0.19 g of 10%Pd/C and 50 PSIG H$_2$ for 2.5 h at room temperature. The Pd/C was removed by filtration through diatomaceous earth and solvent removed from the filtrate in vacuo to give N$^4$-(5-N-(23'-amino-3',6',9',12'-15'-18'-hexa-oxa-tricosanamido)aminopentyl)-N$^1$,N$^9$,N$^{12}$-tris(tert-butyloxycarbonyl)spermine as a colorless oil (0.13 g). N$^4$-(5-N-(23'-amino-3',6',9',12'-15'-18'-hexa-oxa-tricosanamido)aminopentyl)-N$^1$,N$^9$,N$^{12}$-tris(tert-butyloxycarbonyl)spermine (0.13 g) was dissolved in tetrahydrofuran (20 mL) and to the solution was added 0.048 mL of diisopropylethylamine and 0.073 g of succinimidyl S-α-3'-propionyl tetra-O-acetyl-thiomannoside, and the solution stirred at room temperature for 20 h. The solvent was removed in vacuo to give a glass. This glass was purified on silica gel, eluting with a gradient of methanol in chloroform. Fractions containing the product (TLC R$_f$ 0.36, CHCl$_3$/methanol 9:1) were combined and the solvent removed to give 0.10 g of N$^4$-(5-N-(23'-N-(S-α-3'-propionamido tetra-O-acetyl-thiomannoside)-3',6',9',12'-15'-18'-hexa-oxa-tricosanamido)aminopentyl)-N$^1$,N$^9$,N$^{12}$-tris (tert-butyloxycarbonyl)spermine as an oil. FAB mass spectra, MH$^+$=3328. The N$^4$-(5-N-(23'-N-(S-α-3'-propionamido tetra-O-acetyl-thiomannoside)-3',6',9',12'-15'-18'-hexa-oxa-tricosanamido)aminopentyl)-N$^1$,N$^9$,N$^{12}$-tris (tert-butyloxycarbonyl)spermine (0.55 g) was dissolved in 10 mL of trifluoroacetic acid and stirred at room temperature for 2 h. The solvent was removed in vacuo and the residue dissolved in chloroform and the solvent removed (2×20 mL) to give 0.76 g of N$^4$-(5-N-(23'-N-(S-α-3'-propionamido tetra-O-acetyl-thiomannoside)-3',6',9',12'-15'-18'-hexa-oxa-tricosanamido)aminopentyl)-spermine as an oil. This oil was dissolved in 20 mL of methanol and to the solution was added 20 mL of water and 0.85 g of Na$_2$CO$_3$, and the solution stirred at room temperature for 6.5 h. The solvents were removed in vacuo and the residue taken up in 6 mL of 1% acetic acid and purified in four 1.5 mL aliquots on three Sephadex™ G-25 medium columns (12 mL each), eluting with 1% acetic acid. Fractions containing the product were combined and lyophilized to give 0.22 g of N$^4$-(5-N-(23'-N-(S-α-3'-propionamido thiomannoside)-3',6', 9',12'-15'-18'-hexa-oxa-tricosanamido)aminopentyl)-spermine tetraacetate as an oil. NMR (D$_2$O) δ1.35 (m, 4H), 1.55 (m, 6H), 1.75 (m, 6.4H), 1.91 (s, 14H), 2.09 (m, 4.2H), 2.58 (t, 1.7H), 2.90 (m, 1.7H), 3.09, 3.19 (overlapping m, 18.1H), 3.53 (t, 2.5H), 3.69 (m, 22H), 3.88 (m, 3.8H), 4.06 (s, 1.7H), 5.30 (s, 1H).

EXAMPLE 33

Preparation of N$^4$-(5-N-(O-(5-N-(α-3"-propionamido thiomannoside)pentyl)-O-(2-acetamido)nonadecaethylene glycol)pentyl)-spermine tetraacetate N$^4$-(5-N-(O-(5-N-(α-3"-propionamido thiomannoside) pentyl)-O-(2-acetamido)nonadecaethylene glycol)pentyl)-spermine tetraacetate could be prepared similarly to N$^4$-(5-N-(23'-N-(S-α-3'-propionamido thiomannoside)-3',6',9',12'-15'-18'-hexa-oxa-tricosanamido)aminopentyl)-spermine tetraacetate by substituting 18.9 g of poly(ethylene glycol) of average molecular weight 900 for the pentaethyleneglycol in the procedure described in Example 32.

EXAMPLE 34

Preparation of N$^4$-(((23- [N$^2$,N$^6$-bis(β-3'-propionyl galactosyl-β1-4-thioglucoside)lysyl-N$^6$-(β-3'-propionyl galactosyl-β1-4-thioglucoside)lysyl]-amino)-3',6',9',12'-15'-18'-hexa-oxa-tricosanamido) aminopentyl)-spermine tetraacetate N$^4$-(((23-[N$^2$,N$^6$-bis(β-3'-propionyl galactosyl-β1-4-thioglucoside)lysyl-N$^6$-(β-3'-propionyl galactosyl-β1-4- thioglucoside)lysyl]-amino)-3',6',9',12', -15'-18'-hexa-oxa-tricosanamido)aminopentyl)-spermine tetraacetate was prepared similarly to $N^4$-(5-N-(23'-N-(S-α-3'-propionamido thiomannoside)-3',6',9',12'-15'-18'-hexa-oxa-tricosanamido) aminopentyl)-spermine tetraacetate and the procedure described in Example 32. $N^4$-(5-N-(23'-amino-3',6',9',12'-15'-18'-hexa-oxa-tricosanamido)aminopentyl)-$N^1$,$N^9$,$N^{12}$-tris(tert-butyloxycarbonyl)spermine (0.14 g) was dissolved in tetrahydrofuran (25 mL) and to the solution was added 0.052 mL of diisopropylethylamine and 0.37 g of succinimidyl $N^2$,$N^6$-bis(β-3'-propionyl hepta-O-acetyl galactosyl-β1-4-thioglucoside)lysyl-$N^6$-(β-3'-propionyl hepta-O-acetyl galactosyl-β1-4-thioglucoside)lysinate, and the solution stirred at room temperature for 72 h. The solvent was removed in vacuo to give a glass. This glass was purified on silica gel, eluting with a gradient of methanol in chloroform. Fractions containing the product (TLC $R_f$ 0.46, $CHCl_3$/methanol 9:1) were combined and the solvent removed to give 0.15 g of $N^4$-(((5-N-(23'-N-($N^2$,$N^6$-bis(β-3'-propionyl hepta-O-acetyl galactosyl-β1-4-thioglucoside)lysyl-$N^6$-(β-3'-propionyl hepta-O-acetyl galactosyl-β1-4-thioglucoside) lysinamido)-3',6', 19',12'-15'-18'-hexa-oxa-tricosanamido) aminopentyl)-$N^1$,$N^9$,$N^{12}$-tris(tert-butyloxycarbonyl) spermine as a white solid. FAB mass spectra, $MH^+$=3328. The $N^4$-(((5-N-(23'-N-($N^2$,$N^6$-bis(β-3'-propionyl hepta-O-acetyl galactosyl-β1-4-thioglucoside)lysyl-$N^6$-(β-3'-propionyl hepta-O-acetyl galactosyl-β1-4-thioglucoside) lysinamido)-3',6',9',12'-15'-18'-hexa-oxa-tricosanamido) aminopentyl)-$N^1$,$N^9$,$N^{12}$-tris(tert-butyloxycarbonyl) spermine (0.28 g) was dissolved in 10 mL of trifluoroacetic acid and stirred at room temperature for 1 h. The solvent was removed in vacuo and the residue dissolved in chloroform and the solvent removed (2×20 mL) to give 0.36 g of $^4$-(((5-N-(23'-N-($N^2$,$N^6$-bis(β-3'-propionyl hepta-O-acetyl galactosyl-β1-4-thioglucoside)lysyl-$N^6$-(β-3'-propionyl hepta-O-acetyl galactosyl-β1-4-thioglucoside)lysinamido)-3',6',9',12'-15'-18'-hexa-oxa-tricosanamido)aminopentyl)-spermine as an oil. This oil was dissolved in 10 mL of methanol and to the solution was added 10 mL of water and 0.44 g of $Na_2CO_3$, and the solution stirred at room temperature for 24 h. The solvents were removed in vacuo and the residue taken up in 5 mL of 1% acetic acid and 1 mL of ethanol and purified in four 1.5 mL aliquots on two Sephadex™ G-25 medium columns (15 mL and 20 mL), eluting with 10% ethanol in 1% acetic acid. Fractions containing the product were combined and lyophilized to give 0.095 g of $N^4$-(((23-[$N^2$,$N^6$-bis(β-3'-propionyl galactosyl-β1-4-thioglucoside)lysyl-$N^6$-(β-3'-propionyl galactosyl-β1-4-thioglucoside)lysyl]-amino)-3',6',9',12'-15'-18'-hexa-oxa-tricosanamido)aminopentyl)-spermine tetraacetate.

TABLE 1

Picornavirus Family
    Genera: Rhinoviruses: (Medical) responsible for ~50%
        cases of the common cold.
        Etheroviruses: (Medical) includes
        polioviruses, coxsackieviruses, echoviruses,
        and human enteroviruses such as hepatitis A virus.
        Apthoviruses: (Veterinary) these are the foot
        and mouth disease viruses.
    Target antigens: VP1, VP2, VP3, VP4, VPG
Calcivirus Family
    Genera: Norwalk Group of Viruses: (Medical) these
        viruses are an important causative agent of
        epidemic gastroenteritis.
Togavirus Family
    Genera: Alphaviruses: (Medical and Veterinary)
        examples include Senilis viruses, RossRiver
        virus and Eastern & Western Equine encephalitis.
        Reovirus: (Medical) Rubella virus.

TABLE 1-continued

Flariviridue Family
    Examples include: (Medical) dengue, yellow
    fever, Japanese encephalitis, St. Louis
    encephalitis and tick borne encephalitis viruses.
Hepatitis C Virus: (Medical) these viruses are not placed in
a family yet but are believed to be either a togavirus or a
flavivirus. Most similarity is with togavirus family.
Coronavirus Family: (Medical and Veterinary)
    Infectious bronchitis virus (poultry)
    Porcine transmissible gastroenteric virus (pig)
    Porcine hemagglutinating encephalomyelitis virus (pig)
    Feline infectious peritonitis virus (cats)
    Feline enteric coronavirus (cat)
    Canine coronavirus (dog)
    The human respiratory coronaviruses cause ~40
    cases of common cold. EX. 224E, 0C43
    Note - coronaviruses may cause non-A, B or C
    hepatitis
Target antigens:
    E1 - also called M or matrix protein
    E2 - also called S or Spike protein
    E3 - also called HE or hemagglutin-
    elterose glycoprotein (not present in all coronaviruses)
    N - nucleocapsid
Rhabdovirus Family
    Genera: Vesiliovirus
        Lyssavirus: (medical and veterinary) rabies
    Target antigen: G protein
        N protein
Filoviridue Family: (Medical)
    Hemorrhagic fever viruses such as Marburg and
    Ebola virus
Paramyxovirus Family:
    Genera: Paramyxovirus: (Medical and Veterinary)
        Mumps virus, New Castle disease virus
        (important pathogen in chickens)
        Morbillivirus: (Medical and Veterinary)
        Measles, canine distemper
        Pneuminvirus: (Medical and Veterinary)
        Respiratory syncytial virus
Orthomyxovirus Family (Medical)
    The Influenza virus
Bungavirus Family
    Genera: Bungavirus: (Medical) California encephalitis,
        LA Crosse
        Phlebovirus: (Medical) Rift Valley Fever
        Hantavirus: Puremala is a hemahagin fever virus
        Nairvirus (Veterinary) Nairobi sheep disease
        Also many unassigned bungaviruses
Arenavirus Family (Medical)
    LCM, Lassa fever virus
Reovirus Family
    Genera: Reovirus: a possible human pathogen
        Rotavirus: acute gastroenteritis in children
        Orbiviruses: (Medical and Veterinary)
        Colorado Tick fever, Lebombo (humans) equine
        encephalosis, blue tongue
Retrovirus Family
    Sub-Family:
        Oncorivirinal: (Veterinary) (Medical) feline
        leukemia virus, HTLVI and HTLVII
        Lentivirinal: (Medical and Veterinary) HIV,
        feline immunodeficiency virus, equine
        infections, anemia virus
        Spumavirinal
Papovavirus Family
    Sub-Family:
        Polyomaviruses: (Medical) BKU and JCU viruses
    Sub-Family:
        Papillomavirus: (Medical) many viral types
        associated with cancers or malignant
        progression of papilloma
Adenovirus (Medical)
    EX AD7, ARD., O.B. - cause respiratory disease -
    some adenoviruses such as 275 cause enteritis

TABLE 1-continued

Parvovirus Family (Veterinary)
    Feline parvovirus: causes feline enteritis
    Feline panleucopeniavirus
    Canine parvovirus
    Porcine parvovirus
Herpesvirus Family
    Sub-Family: alphaherpesviridue
        Genera: Simplexvirus (Medical)
            HSVI, HSVII
            Varicellovirus: (Medical - Veterinary)
            pseudorabies - varicella zoster
    Sub-Family - betaherpesviridue
        Genera: Cytomegalovirus (Medical)
            HCMV
            Muromegalovirus
    Sub-Family: Gammaherpesviridue
        Genera: Lymphocryptovirus (Medical)
            EBV - (Burkitts lympho)
            Rhadinovirus
Poxvirus Family
    Sub-Family: Chordopoxviridue (Medical - Veterinary)
        Genera: Variola (Smallpox)
            Vaccinia (Cowpox)
            Parapoxvirus - Veterinary
            Auipoxvirus - Veterinary
            Capripoxvirus
            Leporipoxvirus
            Suipoxvirus
    Sub-Family: Entemopoxviridue
Hepadnavirus Family
        Hepatitis B virus
Unclassified
        Hepatitis delta virus

TABLE 2

Bacterial pathogens

Pathogenic gram-positive cocci include: pneumococcal; staphylococcal; and streptococcal.
Pathogenic gram-negative cocci include: meningococcal; and gonococcal.
Pathogenic enteric gram-negative bacilli include: enterobacteriaceae; pseudomonas, acinetobacteria and eikenella; melioidosis; salmonella; shigellosis; hemophilus; chancroid; brucellosis; tularemia; yersinia (pasteurella); streptobacillus moniliformis and spirillum; listeria monocytogenes; erysipelothrix rhusiopathiae; diphtheria; cholera; anthrax; donovanosis (granuloma inguinale); and bartonellosis.
Pathogenic anaerobic bacteria include: tetanus; botulism; other clostridia; tuberculosis; leprosy; and other mycobacteria.
Pathogenic spirochetal diseases include: syphilis; treponematoses: yaws, pinta and endemic syphilis; and leptospirosis.
Other infections caused by higher pathogen bacteria and pathogenic fungi include: actinomycosis; nocardiosis; cryptococcosis, blastomycosis, histoplasmosis and coccidioidomycosis; candidiasis, aspergillosis, and mucormycosis; sporotrichosis; paracoccidiodomycosis, petriellidiosis, torulopsosis, mycetoma and chromomycosis; and dermatophytosis.
Rickettsial infections include rickettsial and rickettsioses.
Examples of mycoplasma and chlamydial infections include: mycoplasma pneumoniae; lymphogranuloma venereum; psittacosis; and perinatal chlamydial infections.

Pathogenic eukaryotes

Pathogenic protozoans and helminths and infections thereby include: amebiasis; malaria; leishmaniasis; trypanosomiasis; toxoplasmosis; pneumocystis carinii; babesiosis; giardiasis; trichinosis; filariasis; schistosomiasis; nematodes; trematodes or flukes; and cestode (tapeworm) infections.

---

What is claimed is:

1. A multifunctional molecular complex useful for transfer of a nucleic acid composition to cells, wherein said multifunctional molecular complex comprises:
   A) a nucleic acid composition; and
   B) a transfer moiety comprising
      (i) one or more cationic polyamine components, wherein each cationic polyamine is non-covalently bound to said nucleic acid composition and comprises from three to twelve nitrogen atoms; and
      (ii) one or more endosome membrane disruption promoting components attached to at least one nitrogen atom of at least one of said polyamine components through an alkyl, carboxamide, carbamate, thiocarbamate, or carbamoyl bridging group, said one or more endosome membrane disruption promoting components independently selected from (a) at least one lipophilic long chain alkyl group or (b) a fusogenic peptide, cholic acid or cholesteryl or a derivative thereof.

2. The multifunctional molecular complex according to claim 1 wherein said nucleic acid composition is a nucleic acid molecule that comprises a nucleotide sequence that encodes a peptide or protein, or serves as a template for a nucleic acid molecule.

3. The multifunctional molecular complex according to claim 1, wherein the transfer moiety of said multifunctional molecular complex further comprises at least one receptor specific binding component which is a ligand for a receptor on a target cell.

4. The multifunctional molecular complex according to claim 3, wherein the receptor specific binding component is attached through a bridging group to either (i) to a further nitrogen atom of at least one of said cationic polyamine components to which said one or more endosome membrane disruption promoting components is attached, or (ii) to a nitrogen atom of at least one further polyamine component which does not have attached thereto any endosome membrane disruption promoting component.

5. The multifunctional molecular complex according to claim 4, wherein the bridging group through which the receptor specific binding component is attached is selected from the group consisting of an alkyl, carboxamide, carbamate, thiocarbamate, and carbamoyl bridging group.

6. The multifunctional molecular complex according to claim 5, wherein the nucleic acid composition is a plasmid.

7. A transfer moiety comprising:
   (a) one or more cationic polyamine components, wherein each cationic polyamine is non-covalently bound to said nucleic acid composition and comprises from three to twelve nitrogen atoms; and
   (b) one or more endosome membrane disruption promoting components attached to at least one nitrogen atom of at least one of said polyamine components through an alkyl, carboxamide, carbamate, thiocarbamate, or carbamoyl bridging group, said one or more endosome membrane disruption promoting components independently selected from (i) at least one lipophilic long chain alkyl group or (ii) a fusogenic peptide, cholic acid or cholesteryl or a derivative thereof.

8. The transfer moiety according to claim 7, wherein said transfer moiety further comprises at least one receptor specific binding component which is a ligand for a receptor on a target cell.

9. The transfer moiety according to claim 7, wherein the receptor specific binding component is attached through a bridging group to either (i) to a further nitrogen atom of at least one of said cationic polyamine components to which said one or more endosome membrane disruption promoting components is attached, or (ii) to a nitrogen atom of at least one further polyamine component which does not have attached thereto any endosome membrane disruption promoting component.

10. The transfer moiety according to claim 9, wherein the bridging group through which the receptor specific binding component is attached is selected from the group consisting of an alkyl, carboxamide, carbamate, thiocarbamate, and carbamoyl bridging group. peptide, cholic acid or cholesteryl or a derivative thereof attached to a nitrogen atom of said polyamine through a shorter alkyl bridging group having a terminal carboxyl, amino, hydroxyl or sulfhydryl group.

* * * * *

UNITED STATES PATENT AND TRADEMARK OFFICE
CERTIFICATE OF CORRECTION

PATENT NO. : 6,379,965 B1
DATED : April 30, 2002
INVENTOR(S) : Raymond Boutin et al.

It is certified that error appears in the above-identified patent and that said Letters Patent is hereby corrected as shown below:

Title page,
Item [60], Related U.S. Application Data, replace "Division of application No. 08/809,397, filed as application No. PCT/US95/12502 on Sep. 28, 1995, now Pat. No. 6,127,170, which is a continuation-in-part of application No. 08/314,060, filed on Sep. 28, 1994, now Pat. No. 5,837,533." with -- Division of application No. 08/809,397, filed March 21, 1997, now US Patent No. 6,127,170, which is a 371 of PCT/US95/12502, filed Sept. 28, 1995, which is a continuation-in-part of US Pat. Application No. 08/314, 060, filed Sept. 28, 1994, now US Pat. No. 5,837,533, issued Nov. 17, 1998. --.

Column 4,
Line 61, replace "facilitated.." with -- facilitated --.

Column 5,
Line 48, replace "Sca." with -- Sci. --.

Column 9,
Line 16, replace "calls" with -- cells --.

Column 10,
Line 48, replace "1 1" with -- 1 --.

Column 17,
Line 34, replace "W" with -- VV --.
Line 56, replace "MOMLV" with -- MoMLV --.
Line 59, replace "F-MULV" with -- F-MuLV --.

Column 18,
Line 50, replace "represents a single or double bond, i.e., a saturated or" with -- - - - represents a single or double bond, i.e., a saturated or --.
Line 55, replace "$(CH_2CH_{2o})_{n'}H$," with -- $(CH_2CH_2O)_{n'}H$, --.

Column 19,
Line 15, replace "represents a single or double bond, i.e., a saturated or" with -- - - - represents a single or double bond, i.e., a saturated or --.
Line 23, replace "$(CH_3)2;and$" with -- $(CH_3)2;$ and --.

Column 20,
Line 12, delete "so".

Column 25,
Line 15, replace "EENA-1" with -- EBNA-1 --.

UNITED STATES PATENT AND TRADEMARK OFFICE
CERTIFICATE OF CORRECTION

PATENT NO.     : 6,379,965 B1
DATED          : April 30, 2002
INVENTOR(S)    : Raymond Boutin et al.

It is certified that error appears in the above-identified patent and that said Letters Patent is hereby corrected as shown below:

<u>Column 37,</u>
Line 25, replace "-⊕1-4-" with -- -β1-4- --.
Lines 27, 46 and 48, replace "⊕1-4-" with -- β1-4- --.

<u>Column 38,</u>
Line 21, replace "⊕1-4-" with -- β1-4- --.

<u>Column 41,</u>
Line 62, replace "⊕1-4-" with -- β1-4- --.

<u>Column 45,</u>
Line 8, replace "7|α," with -- 7″α, --.

<u>Column 47,</u>
Line 56, replace "9:1+04w" with -- 9:1+0.4% --.

<u>Column 50,</u>
Line 42, replace "tetrahydrofurax" with -- tetrahydrofuran --.

<u>Column 51,</u>
Line 63, replace "N $^{12}$" with -- $N^{12}$ --.

<u>Column 53,</u>
Line 22, replace "19′," with -- 9′, --.

<u>Column 67,</u>
Line 52, add after the word "group": -- attached to a nitrogen atom of said polyamine, --.

UNITED STATES PATENT AND TRADEMARK OFFICE
CERTIFICATE OF CORRECTION

PATENT NO.    : 6,379,965 B1
DATED         : April 30, 2002
INVENTOR(S)   : Raymond Boutin et al.

It is certified that error appears in the above-identified patent and that said Letters Patent is hereby corrected as shown below:

<u>Column 70,</u>
Lines 3, 4, 5, 6 and 7, delete "peptide, cholic acid or cholesteryl or a derivative thereof attached to a nitrogen atom of said polyamine through a shorter alkyl bridging group having a terminal carboxyl, amino, hydroxyl or sulfhydryl group".

Signed and Sealed this

Tenth Day of September, 2002

*Attest:*

JAMES E. ROGAN
*Attesting Officer*   *Director of the United States Patent and Trademark Office*